US012173307B2

(12) United States Patent
Mayani et al.

(10) Patent No.: US 12,173,307 B2
(45) Date of Patent: Dec. 24, 2024

(54) METHODS FOR THE PURIFICATION OF VIRAL VECTORS

(71) Applicants: BIOVERATIV THERAPEUTICS INC., Waltham, MA (US); FONDAZIONE TELETHON, Rome (IT); OSPEDALE SAN RAFFAELE S.R.L., Milan (IT)

(72) Inventors: Mukesh Mayani, Waltham, MA (US); Tongyao Liu, Waltham, MA (US); Ayman Ismail, Waltham, MA (US)

(73) Assignees: BIOVERATIV THERAPEUTICS INC., Waltham, MA (US); FONDAZIONE TELETHON, Rome (IT); OSPEDALE SAN RAFFAELE S.R.L., Milan (IT)

( * ) Notice: Subject to any disclaimer, the term of this patent is extended or adjusted under 35 U.S.C. 154(b) by 565 days.

(21) Appl. No.: 17/356,980

(22) Filed: Jun. 24, 2021

(65) Prior Publication Data
US 2022/0033849 A1    Feb. 3, 2022

Related U.S. Application Data

(60) Provisional application No. 63/062,120, filed on Aug. 6, 2020, provisional application No. 63/043,697, filed on Jun. 24, 2020.

(51) Int. Cl.
C12N 15/86    (2006.01)

(52) U.S. Cl.
CPC .... *C12N 15/86* (2013.01); *C12N 2740/15041* (2013.01); *C12N 2740/15051* (2013.01)

(58) Field of Classification Search
CPC .............. C12N 15/86; C12N 2740/15041
See application file for complete search history.

(56) References Cited

U.S. PATENT DOCUMENTS

| 4,683,195 | A | 7/1987 | Mullis et al. |
| 4,683,202 | A | 7/1987 | Mullis et al. |
| 4,704,362 | A | 11/1987 | Itakura et al. |
| 4,800,159 | A | 1/1989 | Mullis et al. |
| 4,868,112 | A | 9/1989 | Toole, Jr. |
| 4,965,188 | A | 10/1990 | Mullis et al. |
| 5,112,950 | A | 5/1992 | Meulien et al. |
| 5,171,844 | A | 12/1992 | van Ooyen et al. |
| 5,304,489 | A | 4/1994 | Rosen |

(Continued)

FOREIGN PATENT DOCUMENTS

| CN | 104427995 A | 3/2015 |
| EP | 0295597 A2 | 12/1988 |

(Continued)

OTHER PUBLICATIONS

Koza et al. Exclusion Chromatography for the Impurity Analysis of Adeno-Associated Virus Serotypes. The Application Notebook 38 : 367-368. Jun. 1, 2020. (Year: 2020).*

(Continued)

*Primary Examiner* — Arthur S Leonard
*Assistant Examiner* — Keenan A Bates
(74) *Attorney, Agent, or Firm* — LATHROP GPM LLP; James H. Velema; James V. DeGiulio

(57) ABSTRACT

Viral vector production processes and methods of purifying a viral vector from a host cell are provided herein.

14 Claims, 11 Drawing Sheets

Specification includes a Sequence Listing.

(56) References Cited

U.S. PATENT DOCUMENTS

| | | |
|---|---|---|
| 5,543,502 A | 8/1996 | Nordfang et al. |
| 5,595,886 A | 1/1997 | Chapman et al. |
| 5,610,278 A | 3/1997 | Nordfang et al. |
| 5,648,260 A | 7/1997 | Winter et al. |
| 5,658,570 A | 8/1997 | Newman et al. |
| 5,712,122 A | 1/1998 | Boime et al. |
| 5,736,137 A | 4/1998 | Anderson et al. |
| 5,739,277 A | 4/1998 | Presta et al. |
| 5,741,957 A | 4/1998 | Deboer et al. |
| 5,789,203 A | 8/1998 | Chapman et al. |
| 5,834,250 A | 11/1998 | Wells et al. |
| 5,849,992 A | 12/1998 | Meade et al. |
| 5,869,046 A | 2/1999 | Presta et al. |
| 5,972,885 A | 10/1999 | Spira et al. |
| 6,030,613 A | 2/2000 | Blumberg et al. |
| 6,048,720 A | 4/2000 | Dalborg et al. |
| 6,060,447 A | 5/2000 | Chapman et al. |
| 6,086,875 A | 7/2000 | Blumberg et al. |
| 6,096,871 A | 8/2000 | Presta et al. |
| 6,121,022 A | 9/2000 | Presta et al. |
| 6,159,730 A | 12/2000 | Reff |
| 6,193,980 B1 | 2/2001 | Efstathiou et al. |
| 6,194,551 B1 | 2/2001 | Idusogie et al. |
| 6,207,455 B1 | 3/2001 | Chang |
| 6,228,620 B1 | 5/2001 | Chapman et al. |
| 6,242,195 B1 | 6/2001 | Idusogie et al. |
| 6,251,632 B1 | 6/2001 | Lillicrap et al. |
| 6,277,375 B1 | 8/2001 | Ward |
| 6,316,226 B1 | 11/2001 | Van Ooyen et al. |
| 6,346,513 B1 | 2/2002 | Van Ooyen et al. |
| 6,413,777 B1 | 7/2002 | Reff et al. |
| 6,458,563 B1 | 10/2002 | Lollar |
| 6,485,726 B1 | 11/2002 | Blumberg et al. |
| 6,528,624 B1 | 3/2003 | Idusogie et al. |
| 6,531,298 B2 | 3/2003 | Stafford et al. |
| 6,538,124 B1 | 3/2003 | Idusogie et al. |
| 6,615,782 B1 | 9/2003 | Hendriksma et al. |
| 6,696,245 B2 | 2/2004 | Winter et al. |
| 6,737,056 B1 | 5/2004 | Presta et al. |
| 6,808,905 B2 | 10/2004 | McArthur et al. |
| 6,818,439 B1 | 11/2004 | Jolly et al. |
| 6,821,505 B2 | 11/2004 | Ward |
| 6,924,365 B1 | 8/2005 | Miller et al. |
| 6,998,253 B1 | 2/2006 | Presta et al. |
| 7,041,635 B2 | 5/2006 | Kim et al. |
| 7,083,784 B2 | 8/2006 | Dall'Acqua et al. |
| 7,179,903 B2 | 2/2007 | McArthur et al. |
| 7,317,091 B2 | 1/2008 | Lazar et al. |
| 7,404,956 B2 | 7/2008 | Peters et al. |
| 7,745,179 B2 | 6/2010 | McArthur et al. |
| 8,326,547 B2 | 12/2012 | Liu et al. |
| 8,734,809 B2 | 5/2014 | Gao et al. |
| 9,050,269 B2 | 6/2015 | Discher et al. |
| 9,050,318 B2 | 6/2015 | Dumont et al. |
| 9,061,059 B2 | 6/2015 | Chakraborty et al. |
| 9,169,491 B2 | 10/2015 | Truran et al. |
| 10,000,748 B2 | 6/2018 | Schüttrumpf et al. |
| 10,058,624 B2 | 8/2018 | Doering et al. |
| 10,125,357 B2 | 11/2018 | Seifried et al. |
| 10,370,431 B2 | 8/2019 | Tan et al. |
| 11,008,561 B2 | 5/2021 | Tan et al. |
| 11,753,461 B2 | 9/2023 | Tan et al. |
| 2003/0069395 A1 | 4/2003 | Sato et al. |
| 2003/0077812 A1 | 4/2003 | McArthur et al. |
| 2003/0109478 A1 | 6/2003 | Fewel et al. |
| 2003/0235536 A1 | 12/2003 | Blumberg et al. |
| 2004/0147436 A1 | 7/2004 | Kim et al. |
| 2006/0003452 A1 | 1/2006 | Humeau et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0243188 A1 | 10/2007 | Lazar et al. |
| 2007/0248603 A1 | 10/2007 | Lazar et al. |
| 2007/0286859 A1 | 12/2007 | Lazar et al. |
| 2008/0004206 A1 | 1/2008 | Rosen et al. |
| 2008/0057056 A1 | 3/2008 | Lazar et al. |
| 2008/0076174 A1 | 3/2008 | Selden et al. |
| 2008/0153156 A1 | 6/2008 | Gray |
| 2008/0153751 A1 | 6/2008 | Rosen et al. |
| 2008/0161243 A1 | 7/2008 | Rosen et al. |
| 2008/0194481 A1 | 8/2008 | Rosen et al. |
| 2008/0260738 A1 | 10/2008 | Moore et al. |
| 2008/0261877 A1 | 10/2008 | Balance et al. |
| 2009/0017533 A1 | 1/2009 | Selden et al. |
| 2009/0042283 A1 | 2/2009 | Selden et al. |
| 2009/0087411 A1 | 4/2009 | Fares et al. |
| 2010/0239554 A1 | 9/2010 | Schellenberger et al. |
| 2010/0284971 A1 | 11/2010 | Samulski |
| 2010/0292130 A1 | 11/2010 | Skerra et al. |
| 2010/0323956 A1 | 12/2010 | Schellenberger et al. |
| 2011/0046060 A1 | 2/2011 | Schellenberger et al. |
| 2011/0046061 A1 | 2/2011 | Schellenberger et al. |
| 2011/0077199 A1 | 3/2011 | Schellenberger et al. |
| 2011/0172146 A1 | 7/2011 | Schellenberger et al. |
| 2011/0244550 A1 | 10/2011 | Simioni |
| 2012/0178691 A1 | 7/2012 | Schellenberger et al. |
| 2013/0024960 A1 | 1/2013 | Nathwani et al. |
| 2013/0052191 A1 | 2/2013 | Blein et al. |
| 2013/0195801 A1 | 8/2013 | Gao et al. |
| 2014/0010861 A1 | 1/2014 | Bancel et al. |
| 2015/0023959 A1 | 1/2015 | Chhabra et al. |
| 2015/0056696 A1 | 2/2015 | Fan et al. |
| 2015/0158929 A1 | 6/2015 | Schellenberger et al. |
| 2015/0361158 A1 | 12/2015 | Tan et al. |
| 2016/0304851 A1 | 10/2016 | Schüttrumpf et al. |
| 2017/0073702 A1 | 3/2017 | Truran et al. |
| 2017/0260516 A1 | 9/2017 | Tan et al. |
| 2017/0326256 A1 | 11/2017 | Doering et al. |
| 2019/0048362 A1 | 2/2019 | Kyostio-Moore et al. |
| 2019/0185543 A1 | 6/2019 | Tan et al. |
| 2019/0314291 A1 | 10/2019 | Besin et al. |
| 2020/0024327 A1 | 1/2020 | Tan et al. |
| 2020/0199626 A1 | 6/2020 | Liu et al. |
| 2021/0038744 A1 | 2/2021 | Annoni et al. |
| 2021/0113634 A1 | 4/2021 | Kroetsch et al. |
| 2021/0115425 A1 | 4/2021 | Tan et al. |
| 2022/0033849 A1 | 2/2022 | Mayani et al. |
| 2022/0090130 A1 | 3/2022 | Maghodia et al. |

FOREIGN PATENT DOCUMENTS

| | | |
|---|---|---|
| EP | 1395293 A1 | 3/2004 |
| EP | 2173890 B1 | 3/2011 |
| EP | 2829285 A1 | 1/2015 |
| EP | 2881463 A1 | 6/2015 |
| EP | 3160478 A1 | 5/2017 |
| EP | 3377618 A1 | 9/2018 |
| EP | 3411478 A1 | 12/2018 |
| EP | 2956477 B1 | 11/2020 |
| EP | 3746136 A1 | 12/2020 |
| EP | 3891289 A2 | 10/2021 |
| RU | 2500816 C1 | 12/2013 |
| RU | 2577979 C2 | 3/2016 |
| WO | WO 1987/004187 A1 | 7/1987 |
| WO | WO 1988/000831 A1 | 2/1988 |
| WO | WO 1988/007089 A1 | 9/1988 |
| WO | WO 1991/009122 A1 | 6/1991 |
| WO | WO 1996/014339 A1 | 5/1996 |
| WO | WO 1997/012622 A1 | 4/1997 |
| WO | WO 1998/005787 A1 | 2/1998 |
| WO | WO 1998/009657 A2 | 3/1998 |
| WO | WO 1998/017815 A1 | 4/1998 |
| WO | WO 1998/017816 A1 | 4/1998 |
| WO | WO 1998/018934 A1 | 5/1998 |
| WO | WO 1998/023289 A1 | 6/1998 |
| WO | WO 1999/031251 A1 | 6/1999 |
| WO | WO 1999/051642 A1 | 10/1999 |
| WO | WO 1999/058572 A1 | 11/1999 |
| WO | WO 2000/009560 A2 | 2/2000 |
| WO | WO 2000/020561 A1 | 4/2000 |
| WO | WO 2000/032767 A1 | 6/2000 |
| WO | WO 2000/042072 A2 | 7/2000 |
| WO | WO 2000/066759 A1 | 11/2000 |

(56) References Cited

FOREIGN PATENT DOCUMENTS

| | | |
|---|---|---|
| WO | WO 2002/044215 A2 | 6/2002 |
| WO | WO 2002/060919 A2 | 8/2002 |
| WO | WO 2002/063025 A2 | 8/2002 |
| WO | WO 2002/040544 A3 | 10/2002 |
| WO | WO 2002/092134 A1 | 11/2002 |
| WO | WO 2003/020764 A2 | 3/2003 |
| WO | WO 2003/042361 A2 | 5/2003 |
| WO | WO 2003/042397 A2 | 5/2003 |
| WO | WO 2003/052051 A2 | 6/2003 |
| WO | WO 2003/057780 A1 | 7/2003 |
| WO | WO 2003/074569 A2 | 9/2003 |
| WO | WO 2003/077834 A2 | 9/2003 |
| WO | WO 2003/100053 A1 | 12/2003 |
| WO | WO 2004/016750 A2 | 4/2004 |
| WO | WO 2004/029207 A2 | 4/2004 |
| WO | WO 2004/035752 A2 | 4/2004 |
| WO | WO 2004/044859 A1 | 5/2004 |
| WO | WO 2004/063351 A2 | 7/2004 |
| WO | WO 2004/074455 A2 | 9/2004 |
| WO | WO 2004/094642 A2 | 11/2004 |
| WO | WO 2004/099249 A2 | 11/2004 |
| WO | WO 2005/013901 A2 | 2/2005 |
| WO | WO 2005/040217 A2 | 5/2005 |
| WO | WO 2005/052171 A2 | 6/2005 |
| WO | WO 2005/070963 A1 | 8/2005 |
| WO | WO 2005/077981 A2 | 8/2005 |
| WO | WO 2005/092925 A2 | 10/2005 |
| WO | WO 2005/123780 A2 | 12/2005 |
| WO | WO 2006/019447 A1 | 2/2006 |
| WO | WO 2006/047350 A2 | 5/2006 |
| WO | WO 2006/085967 A2 | 8/2006 |
| WO | WO 2007/000668 A2 | 1/2007 |
| WO | WO 2007/004670 A1 | 1/2007 |
| WO | WO 2007/021494 A2 | 2/2007 |
| WO | WO 2007/046703 A2 | 4/2007 |
| WO | WO 2007/148971 A2 | 12/2007 |
| WO | WO 2007/149406 A2 | 12/2007 |
| WO | WO 2007/149852 A2 | 12/2007 |
| WO | WO 2008/012543 A1 | 1/2008 |
| WO | WO 2008/118507 A2 | 10/2008 |
| WO | WO 2008/143954 A2 | 11/2008 |
| WO | WO 2008/155134 A1 | 12/2008 |
| WO | WO 2009/051717 A2 | 4/2009 |
| WO | WO 2009/058322 A1 | 5/2009 |
| WO | WO 2009/075772 A1 | 6/2009 |
| WO | WO 2009/130198 A2 | 10/2009 |
| WO | WO 2009/137254 A2 | 11/2009 |
| WO | WO 2009/140015 A2 | 11/2009 |
| WO | WO 2010/029178 A1 | 3/2010 |
| WO | WO 2010/055413 A1 | 5/2010 |
| WO | WO 2010/091122 A1 | 8/2010 |
| WO | WO 2010/115866 A1 | 10/2010 |
| WO | WO 2010/125471 A2 | 11/2010 |
| WO | WO 2010/140148 A1 | 12/2010 |
| WO | WO 2010/144502 A2 | 12/2010 |
| WO | WO 2010/144508 A1 | 12/2010 |
| WO | WO 2011/004361 A2 | 1/2011 |
| WO | WO 2011/005968 A1 | 1/2011 |
| WO | WO 2011/028228 A1 | 3/2011 |
| WO | WO 2011/028229 A1 | 3/2011 |
| WO | WO 2011/028344 A2 | 3/2011 |
| WO | WO 2011/033105 A1 | 3/2011 |
| WO | WO 2011/069164 A2 | 6/2011 |
| WO | WO 2012/006615 A1 | 1/2012 |
| WO | WO 2012/006624 A2 | 1/2012 |
| WO | WO 2012/006633 A1 | 1/2012 |
| WO | WO 2012/006635 A1 | 1/2012 |
| WO | WO 2012/170289 A1 | 12/2012 |
| WO | WO 2013/009627 A2 | 1/2013 |
| WO | WO 2013/093760 A2 | 6/2013 |
| WO | WO 2013/122617 A1 | 8/2013 |
| WO | WO 2013/123457 A1 | 8/2013 |
| WO | WO 2014/011819 A2 | 1/2014 |
| WO | WO 2014/127215 A1 | 8/2014 |
| WO | WO 2015/023891 A2 | 2/2015 |
| WO | WO 2015/038625 A1 | 3/2015 |
| WO | WO 2015/086406 A2 | 6/2015 |
| WO | WO 2015/106052 A1 | 7/2015 |
| WO | WO 2016/004113 A1 | 1/2016 |
| WO | WO 2016/009326 A1 | 1/2016 |
| WO | WO 2016/168728 A2 | 10/2016 |
| WO | WO 2017/024060 A1 | 2/2017 |
| WO | WO 2017/087861 A1 | 5/2017 |
| WO | WO 2017/136358 A1 | 8/2017 |
| WO | WO 2017/139576 A1 | 8/2017 |
| WO | WO-2019006390 A1 * | 1/2019 | ............ B01D 15/34 |
| WO | WO-2019152692 A1 * | 8/2019 | ............ A61K 38/37 |
| WO | WO 2020/113197 A1 | 6/2020 |
| WO | WO 2020/118069 A2 | 6/2020 |
| WO | WO 2021/067389 A1 | 4/2021 |

OTHER PUBLICATIONS

Human proteome project (Human Proteome Organization). https://hupo.org/hpp-progress-to-date. Accessed Oct. 25, 2023. (Year: 2023).*

Mazurkiewicz-Pisarek et al. The factor VIII protein and its function. Acta Biochemica Polonica 63: 11-16. (Year: 2016).*

GE Healthcare Life Sciences Size Exclusion Chromatography Principles and Methods. (Year: 2014).*

Gelderblom. Medical Microbiology 4: Chapter 41 Structure and Classification of Viruses. (Year: 1996).*

Shestapol et al. Expression and characterization of a codon-optimized blood coagulation factor VIII. Journal of Thrombosis and Haemostasis 15: 709-720. (Year: 2017).*

Cytiva (HisTrap Excel). https://www.cytivalifesciences.com/en/us/shop/chromatography/prepacked-columns/affinity-tagged-protein/histrap-excel-p-00310 (Year: 2024).*

Seop et al. Removal and Inactivation of Viruses during Manufacture of a High Purity Antihemophilic Factor VIII Concentrate from Human Plasma. J Microbiol Biotechnol 11: 497-503. (Year: 2001).*

Cytiva (VIIISelect) (Year: 2020).*

Weigel et al. A flow-through chromatography process for influenza A and B virus purification. Journal of Virological Methods 207: 45-53. (Year: 2014).*

Yamada et al. Lentivirus Vector Purification Using Anion Exchange HPLC Leads to Improved Gene Transfer. BioTechniques 34: 1074-1080. (Year: 2003).*

Kutner et al. Simplified production and concentration of HIV-1-based lentiviral vectors using HYPERFlask vessels and anion exchange membrane chromatography. BMC Biotechnology 9: 1-7. (Year: 2009).*

Baekelandt et al., "Optimized lentiviral vector production and purification procedure prevents immune response after transduction of mouse brain Laboratory for Experimental", Jun. 2003, 10: 1933-1940.

International Search Report & Written Opinion for PCT International Patent Application No. PCT/US2021/038871, mailed Nov. 24, 2021.

Johnston et al., "Generation of an optimized lentiviral vector encoding a high-expression factor VIII transgene for gene therapy of hemophilia A", Gene Therapy, Jun. 2013, 20(6):607-615.

Maunder et al., "Enhancing titres of therapeutic viral vectors using the transgene repression in vector production (TRIP) system", Nature Communications, Mar. 2017, 8(1).

McCue et al., "Application of a novel affinity adsorbent for the capture and purification of recombinant Factor VIII compounds", J. Chroma., Nov. 6, 2009, 1216(45): 7824-7830.

Otto-Wilhelm Merten et al., "Production of lentiviral vectors", Molecular Therapy—Methods & Clinical Development, Jan. 2016, 3: 1-14.

Amendola et al. (2005) "Coordinate dual-gene transgenesis by lentiviral vector carrying synthetic bidriectional promoters," Nature Biotechnology, 23(1):108-116.

Andersson, et al., "Purification and Characterization of Human Factor IX", Thrombosis Research, vol. 7, Issue 3, pp. 451-459. (Sep. 1975).

(56) References Cited

OTHER PUBLICATIONS

Armour et al. (1999) "Recombinant human IgG molecules lacking Fcγ receptor I binding and monocyte triggering activities," Eur. J. Immunol., 29: 2613-2624.

Baldassarre, et al., "Production of Transgenic Goats by Pronuclear Microinjection Of In Vitro Produced Zygotes Derived From Oocytes Recovered by Laparoscopy", Theriogenology, vol. 59, Issues 3-4, pp. 831-839, Feb. 2003.

Benhar, et al., "Cloning, Expression and Characterization of the Fv Fragments of the Anti-Carbohydrate mAbs B1 and B5 as Single-Chain Immunotoxins", Protein Engineering, Design and Selection, vol. 7, No. 12, pp. 1509-1515, Dec. 1994.

Biochemistry, 1990, Section 6-3 Chemical Evolution, pp. 126-129, John Wiley and Sons.

Bril et al. (2006) "Tolerance to factor VIII in a transgenic mouse expressing human factor VIII cDNA carrying an Arg$^{593}$ to Cys substitution", Thromb. Haemost. 95(2):341-347.

Brinster, et al., "Expression of a Microinjected Immunoglobulin Gene in the Spleen of Transgenic Mice", Nature, vol. 306, No. 5941, pp. 332-336, 1983.

Brinster, et al., "Factors Affecting the Efficiency of Introducing Foreign DNA Into Mice by Microinjecting Eggs", Proceedings of the National Academy of Sciences of the United States of America, vol. 82, No. 13, pp. 4438-4442, Jul. 1, 1985.

Brown et al., "Endogenous microRNA can be broadly exploited to regulate transgene expression according to tissue, lineage and differentiation state", Nat. Biotechnol., Dec. 2007, 25(12): 1457-1467.

Brown, et al., "A microRNA-Regulated Lentiviral Vector Mediates Stable Correction of Hemophilia B Mice", Blood, vol. 110, No. 13, pp. 4144-4152, Dec. 15, 2007.

Brown, et al., "Production of Recombinant H1 Parvovirus Stocks Devoid of Replication-Competent Viruses", Human Gene Therapy, vol. 13, No. 18, pp. 2135-2145, Dec. 10, 2002.

Burgess-Brown et al., "Codon Optimization Can Improve Expression of Human Genes in *Escherichia coli*: A Multi-Gene Study", Protein Expression and Purification, 2008, vol. 59, No. 1, pp. 94-102.

Burmeister, et al., "Crystal Structure of the Complex of Rat Neonatal Fc Receptor with Fc", Nature, vol. 372, No. 6504, pp. 379-383, Nov. 24, 1994.

Cameron, C., et al., "The Canine Factor VIII cDNA and 5' Flanking Sequence," Thrombosis and Haemostasis 79(2):317-322, Schattauer, Germany (1998).

Cantore et al., "Hyperfunctional Coagulation Factor IX Improves The Efficacy of Gene Therapy in Hemophilic Mice", Blood, 2012, vol. 120, No. 23, pp. 4517-4520.

Cantore et al., "Liver-Directed Gene Therapy for Hemophilia B with Immune Stealth Lentiviral Vectors", Gene Therapy and Transfer: Gene Therapy for Hemophilia and Improving Lentiviral Vectors, Dec. 7, 2017 Blood, 130(Suppl. 1): 605.

Cao et al., "Factor VIII Accelerates Proteolytic Cleavage of Von Willebrand Factor by ADAMTS13", PNAS May 27, 2008, 105(21): 7416-7421.

Capon et al. (1989) "Designing CD4 immunoadhesins for AIDS therapy," Nature, 337, 525-531.

Chiorini et al. (1997) "Cloning of Adeno-Associated Virus Type 4 (AAV4) and Generation of Recombinant AAV4 Particles," Journal of Virology, 71(9):6823-6833.

Chiorini et al. (1999) "Cloning and Characterization of Adeno-Associated Virus Type5," Journal of Virology, 73(2):1309-1319.

Cleland et al., "A novel long-acting human growth hormone fusion protein (vrs-317): enhanced in vivo potency and half-life", Journal of Pharmaceutical Sciences, 2012, 101(8): 2744-2754.

Codon Optimization for Increased Protein Expression, downloaded Mar. 26, 2018 from GenScript, OptimumGene—Codon Optimization.

Codon Usage Database, Retrieved from http://www.kazusa.or.jp/codon/, 2013, 1 page.

Comparison of codon usage frequency in Seq ID No. 1 and Seq ID: 3 of the Patent and Seq ID: 5 of D2 (WO 2011/005968 A1, submitted with IDS dated Sep. 7, 2021)., Defensive Opposition regarding European Patent No. EP2956477 filed by Bioverative Therapeutics Inc., dated Mar. 11, 2022.

Comparison of in vivo FVIII activity after expression with codon optimised FVIII (Seq ID: 1) and non-optimised FVIII (Seq ID: 3), Defensive Opposition regarding European Patent No. EP2956477 filed by Bioverative Therapeutics Inc., dated Mar. 11, 2022.

Cutler et al., "The Identification and Classification of 41 Novel Mutations in the Factor VIII Gene (F8c)", Human Mutation, Mar. 2002, vol. 19, No. 3, pp. 274-278.

Dalkara et al. (2013) "In vivo-directed evolution of a new adeno-associated virus for therapeutic outer retinal gene delivery from the vitreous," Sci. Transl. Med., 5(189):189ra76, 12 pages.

Database Geneseq, "Human Codon-Optimized Clotting Factor IX (hFIX) Gene, Seq ID No. 2", XP002776590, retrieved from EBI accession No. GSN: BBB41169 Database accession No. BBB41169, Feb. 27, 2014.

Defensive Opposition regarding European Patent No. EP2956477 filed by Bioverative Therapeutics Inc., dated Mar. 11, 2022, including Main Request and Auxiliary Requests 1, 1a, 2a, 3a, 3, 4, 5, 5a, 6a, 6, 7, 7a, 8, 9a, 9, 10a, 10, 11a, 11, 12, 13a, 13, 14, 14a, 15a, and 15.

Dellgren, et al., "Cell Surface Expression Level Variation between Two Common Human Leukocyte Antigen Alleles, HLA-A2 and HLA-B8, Is Dependent on the Structure of the C Terminal Part of the Alpha 2 and the Alpha 3 Domains", PLoS One, vol. 10, No. 8, e0135385, pp. 1-15, Aug. 25, 2010.

Dennis et al. (2002) "Albumin binding as a general strategy for improving the pharmacokinetics of proteins," The Journal of Biological Chemistry, 277(38):35035-35043.

Ding et al., "Multivalent Antiviral XTEN-Peptide Conjugates with Long in Vivo Half-Life and Enhanced Solubility", Bioconjugate Chemistry, 2014, 25(7): 1351-1359.

Eaton, D.L., et al., "Construction and Characterization of an Active Factor VIII Variant Lacking the Central One-Third of the Molecule," Biochemistry 25(26):8343-8347, American Chemical Society, United States (1986).

Ellman et al. (1991) "Biosynthetic Method for Introducing Unnatural Amino Acids Site-Specifically into Proteins," Methods in Enzymology, 202 (15): 301-336.

Ensembl, Gene: B2M ENSG00000166710, Beta-2-Microglobulin, obtained from url: http://uswest.ensembl.org/Homo_sapiens/Gene/Summary?g=ENSG00000166710;r=15:44711477-44718877;mobileredirect=no.

Europapress (www.europapress.es), "European Commission Approves ReFacto AF(TM) as a Variation to the Refacto(R) Marketing Authorisation", Mar. 11, 2009, 2 pages.

Extended European Search Report for European Patent Application No. 20204866.6, mailed Aug. 9, 2021.

Extended European Search Report for European Patent Application No. 22176817.9, mailed Jan. 20, 2023.

Fallaux, F.J., et al., "The Human Clotting Factor VIII cDNA Contains an Autonomously Replicating Sequence Consensus- and Matrix Attachment Region-like Sequence That Binds a Nuclear Factor, Represses Heterologous Gene Expression, and Mediates the Transcriptional Effects of Sodium Butyrate," Molecular and Cellular Biology 16(8):4264-4272, American Society for Microbiology, United States (1996).

Fathallah, et al., Effects of Hypertonic Buffer Composition on Lymph Node Uptake and Bioavailability of Rituximab, After Subcutaneous Administration, Biopharmaceutics & Drug Disposition, vol. 36, No. 2, pp. 115-125, Mar. 2015.

FDA Orphan Drug Designation and Approval for ReFacto, Feb. 8, 1996, 2 pages, Retrieved from www.accessdata.fda.gov.

Friend et al. (1999) "Phase I Study of an Engineered Aglycosylated Humanized CD3 Antibody in Renal Transplant Rejection," Transplantation, 68 (11): 1632-1637.

Gaspar et al. (2012) "EuGene: maximizing synthetic gene design for heterologous expression," Bioinformatics, 28(20):2683-2684.

(56) References Cited

OTHER PUBLICATIONS

GenBank Database, "Adeno-associated virus 2, complete genome", GenBank Accession No. AF043303.1, May 20, 2010, Retrieved from: <<https://www.ncbi.nlm.nih.gov/nuccore/AF043303.1>>.
GenBank Database, "Adeno-associated virus 2, complete genome", GenBank Accession No. J01901.1, Apr. 27, 1993, Retrieved from: <<https://www.ncbi.nlm.nih.gov/nuccore/J01901.1>>.
GenBank Database, "Adeno-associated virus 4, complete genome", GenBank Accession No. U89790.1, Aug. 21, 1997, Retrieved from: <<https://www.ncbi.nlm.nih.gov/nuccore/U89790.1>>.
GenBank Database, "Adeno-associated virus 5 DNA binding trs helicase (Rep22) and capsid protein (VP1) genes, complete cds", GenBank Accession No. AF085716.1, Feb. 9, 1999, Retrieved from: <<https://www.ncbi.nlm.nih.gov/nuccore/AF085716.1>>.
GenBank Database, "Transferrin Precursor [*Homo sapiens*]", GenBank Accession No. AAA61140.1, Jan. 14, 1995, 1 page, Retrieved from: <<http://www.ncbi.nlm.nih.gov/protein/AAA61140.1>>.
GenBank, "*Homo sapiens* von Willebrand factor (VWF), mRNA," Accession No. NM_000552.3, Accessed at http://www.ncbi.nlm.nih.gov/nuccore/NM_000552.
Genbank, "Von Willebrand Factor Preproprotein [*Homo sapiens*]," Accession No. NP000543 .2, Accessed at http://www.ncbi.nlm.nih.gov/protein/NP_000543.
GenBank, "*Homo sapiens* Transferrin (TF), mRNA", GenBank Accession No. XM002793, May 13, 2002, 2 pages, Retrieved from: <<https://www.ncbi.nlm.nih.gov/nuccore/XM_002793.7?report=genbank>>.
GenBank, "*Homo sapiens* Transferrin (TF), mRNA", GenBank Accession No. XM039845, Jul. 16, 2001, 2 pages, Retrieved From: <<https://www.ncbi.nlm.nih.gov/nuccore/XM_039845.1?report=genbank>>.
GenBank, "*Homo sapiens* Transferrin (TF), mRNA", GenBank Accession No. XM039847, Jul. 16, 2001, 2 pages, Retrieved From <<https://www.ncbi.nlm.nih.gov/nuccore/XM_039847.1?report=genbank>>.
GenBank, "*Homo sapiens* Transferrin (TF), Transcript Variant 1, mRNA", GenBank Accession No. NM001063, Sep. 3, 2009, 5 pages, Retrieved from: <<http://www.ncbi.nlm.nih.gov/nuccore/NM_001063>>.
GenBank, "Human Transferrin mRNA, Complete cds", GenBank Accession No. M12530, Jan. 14, 1995, 2 pages, Retrieved From: <<http://www.ncbi.nlm.nih.gov/nuccore/M12530>>.
GenBank, "Transferrin [Human, Liver, mRNA, 2347 nt]", GenBank Accession No. S95936, May 7, 1993, 2 pages, Retrieved From: <<http://www.ncbi.nlm.nih.gov/nuccore/S95936>>.
GenBank, *Homo sapiens* von Willebrand Factor (VWF), mRNA, NCBI Reference Sequence: NM_000552.4, Retrieved from: <<https://www.ncbi.nlm.nih.gov/nuccore/NM_000552.4>>, 15 Pages, Apr. 28, 2016.
Generation Bio, "Generation Bio Announces Two Non-Viral Gene Therapy Milestone Achievements: Target Levels of Factor VIII Expression in Hemophilia a Mice and Translation of Expression from Mice to Non-Human Primates", Jan. 4, 2021, obtained from url: <https://www.globenewswire.com/en/news-release/2021/01/04/2152472/0/en/Generation-Bio-Announces-Two-Non-Viral-Gene-Therapy-Milestone-Achievements-Target-Levels-of-Factor-VIII-Expression-in-Hemophilia-A-Mice-and-Translation-of-Expression-from-Mice-to-N.html>.
Giangrande, Paul, "Haemophilia B: Christmas Disease", Expert Opinion on Pharmacotherapy, vol. 6, No. 9, pp. 1517-1524. (2005).
Graf, M., et al., "Concerted Action of Multiple Cis-acting Sequences Is Required for Rev Dependence of Late Human Immunodeficiency Vims Type 1 Gene Expression," Journal of Virology 74(22):10822-10826, American Society for Microbiology, United States (2000).
Higashikawa, et al., Kinetic Analyses of Stability of Simple and Complex Retroviral Vectors, Virology, vol. 280, No. 1, pp. 124-131, 2001.
Ho et al. (1989) "Site-directed mutagenesis by overlap extension using the polymerase chain reaction," Elsevier Science Pub. B.V. (Biomed. Div.), Gene, 77: 51-59.

Hoeben, R.C., et al., "Expression of Functional Factor VIII in Primary Human Skin Fibroblasts after Retrovirus-mediated Gene Transfer," The Journal of Biological Chemistry 265(13): 7318-7323, The American Society for Biochemistry and Molecular Biology, United States (1990).
Hoeben, R.C., et al., "Expression of the Blood-clotting Factor-VIII cDNA Is Repressed by a Transcriptional Silencer Located in Its Coding Region," Blood 85(9):2447-2454, American Society of Hematology, United States (1995).
Holt et al. (2008) "Anti-serum albumin domain antibodies for extending the half-lives of short lived drugs," Protein Engineering, Design and Selection, 21(5):283-288.
Holt, et al., "Domain Antibodies: Proteins for therapy", Trends in Biotechnology, vol. 21, Issue 11, pp. 484-490, Nov. 2003.
Horton et al. (1993) "Gene Splicing by Overlap Extension," Methods in Enzymology, 217 (17): 270-279.
International Preliminary Report on Patentability for PCT International Patent Application No. PCT/US2017/015879, mailed Aug. 7, 2018.
International Preliminary Report on Patentability for PCT International Patent Application No. PCT/US2019/016122, mailed Aug. 4, 2020.
International Search Report & Written Opinion for PCT International Patent Application No. PCT/US2019/016122, mailed Mar. 21, 2019.
International Search Report & Written Opinion for PCT International Patent Application No. PCT/US2020/053463, mailed Feb. 4, 2021.
International Search Report and Written Opinion for PCT International Application No. PCT/US2015/038678, mailed Dec. 8, 2015.
International Search Report and Written Opinion for PCT International Patent Application No. PCT/US2014/016441, mailed May 23, 2014.
International Search Report and Written Opinion for PCT International Patent Application No. PCT/US2017/015879, mailed Apr. 5, 2017.
International Search Report and Written Opinion for PCT International Patent Application No. PCT/US2019/064711, mailed Jun. 23, 2020.
Israel et al. (1997) "Expression of the neonatal Fc receptor, FcRn, on human intestinal epithelial cells," Immunology 92: 69-74.
Kasuda et al., "Establishment of Embryonic Stem Cells Secreting Human Factor VIII for Cell-Based Treatment of Hemophilia A", Journal of Thrombosis and Haemostasis, Aug. 2008, vol. 6, No. 8, pp. 1352-1359.
Kimchi-Sarfaty et al., "A" Silent"Polymorphism in the Mdr1 Gene Changes Substrate Specificity", Science, 2007, vol. 315, No. 5811, pp. 525-528.
Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (2002).
Koeberl, D.D., et al., "Sequences within the Coding Regions of Clotting Factor VIII and CFTR Block Transcriptional Elongation," Human Gene Therapy 6(4):469-479, M.A. Liebert, United States (1995).
Konig et al. (1998) "Use of an albumin-binding domain for the selective immobilisation of recombinant capture antibody fragments on ELISA plates," Journal of Immunological Methods, 218:73-83.
Kotterman et al. (2014) "Engineering adeno-associated viruses for clinical gene therapy," Nat. Rev. Genet., 15(7):445-451.
Kraulis et al. (1996) "The serum albumin-binding domain of streptococcal protein G is a three-helical bundle: a heteronuclear NMR study," FEBS Letters, 378:190-194.
Kudla et al. (2006) "High Guanine and Cytosine Content Increases mRNA Levels in Mammalian Cells," PloS Biol, e180.
Lange, et al., "Overexpression of Factor VIII After AAV Delivery Is Transiently Associated With Cellular Stress in Hemophilia A Mice", Molecular Therapy-Methods & Clinical Development, vol. 3, No. 16064, pp. 1-8, 2016.

(56) References Cited

OTHER PUBLICATIONS

Langner, K-D., et al., "Synthesis of Biologically Active Deletion Mutants of Human Factor VIII:C," Behring Institute Mitteilungen 82:16-25, Behringwerke AG, Germany (1988).
Larrick et al. (1989) "Rapid Cloning of Rearranged Immunoglobulin Genes From Human Hybridoma Cells Using Mixed Primers and the Polymerase Chain Reaction," Biochem. and Biophys. Res. Comm. 160 (3): 1250-1256.
Le Bras et al., "Shielded vectors improve liver gene therapy", Lab Animal, 2019, 48: 238.
Lenting, P.J., et al., "Clearance Mechanisms of Von Willebrand Factor and Factor VIII," Journal of Thrombosis and Haemostasis 5(7):1353-1360, International Society on Thrombosis and Haemostasis, England (2007).
Lenting, P.J., et al., "The Life Cycle of Coagulation Factor VIII in View of its Structure and Function," Blood, 92(11):3983-3996, American Society of Hematology, United States (1998).
Lind et al., "Novel Forms of B-domain-deleted Recombinant Factor VIII molecules Construction and Biochemical Characterization", Eur Journ Biochem., Aug. 15, 1995, 232: 19-27.
Linhult et al. (2002) "Mutational analysis of the interaction between albumin-binding domain from streptococcal protein G and human serum albumin," Protein Science, 11:206-213.
Liu et al., "Codon Optimization Improves Factor IX Expression in Hemophilia B Mice by More Than 15-Fold", Human Gene Therapy, Oct. 2015, vol. 26, No. 10, p. A2.
Lynch, C.M., et al., "Sequences in the Coding Region of Clotting Factor VIII Act as Dominant Inhibitors of RNA Accumulation and Protein Production," Human Gene Therapy 4(3):259-272, M.A. Liebert, United States (1993).
Malassagne, et al. (Apr. 14, 2003) "Hypodermin A, A New Inhibitor of Human Complement for the Prevention of Xenogeneic Hyperacute Rejection", Xenotransplantation, vol. 10, Issue 3, pp. 267-277.
Manco-Johnson, M.J., et al., "Prophylaxis Versus Episodic Treatment to Prevent Joint Disease in Boys with Severe Hemophilia," The New England Journal of Medicine 357(6):535-544, Massachusetts Medical Society, United States (2007).
Mannucci, P.M. and Tuddenham, E.G.D., "The Hemophilias—fromRoyal Genes to Gene Therapy," New England Journal of Medicine 344(23):1773-1779, Massachusetts Medical Society, United States (2001).
McKnight, et al. (Sep. 1983) "Expression of The Chicken Transferrin Gene in Transgenic Mice", Cell, vol. 34, Issue 2, pp. 335-341.
Meulien, P., et al., "A New Recombinant Procoagulant Protein Derived from the cDNA Encoding Human Factor VIII," Protein Engineering 2(4):301-306, IRL Press Ltd., England (1988).
Miao et al., "Bioengineering of Coagulation Factor VIII for Improved Secretion", Blood, May 1, 2004, vol. 103, No. 9, pp. 3412-3419.
Milani et al., "Phagocytosis-shielded lentiviral vectors improve liver gene therapy in nonhuman primates", Sci Transl Med., May 22, 2019, 11(493): eaav7325.
Milani, et al., "Genome Editing for Scalable Production of Alloantigen-Free Lentiviral Vectors for In Vivo Gene Therapy", EMBO Molecular Medicine, Aug. 23, 2017, 9(11): 1558-1573.
Morfini, M., "Pharmacokinetics of Factor VIII and Factor IX," Haemophilia 9(Suppl. 1):94-100, Blackwell Publishing Ltd., England (2003).
Muller, et al. (Aug. 2007) "Recombinant Bispecific Antibodies for Cellular Cancer Immunotherapy", Current opinion in molecular therapeutics, vol. 9, No. 4, pp. 319-326.
Nair et al., "Computationally Designed Liver-Specific Transcriptional Modules and Hyperactive Factor IX Improve Hepatic Gene Therapy", Blood, 2014, vol. 123, No. 20, pp. 3195-3199.
Nair et al., "Computationaly Designed Liver-Specific Transcriptional Modules and Hyperactive Factor IX Improve Hepatic Gene Therapy ERRATA 2007", Blood, Mar. 19, 2015, vol. 125, No. 12.
Nakamura et al. (2000) "Codon usage tabulated from international DNA sequence databases: status for the year 2000," Nucleic Acids Research, 28 (1): 292.

Narita et al. (1998) "The low-density lipoprotein receptor-related protein (LRP) mediates clearance of coagulation factor Xa in Vivo," Blood, 91(2):555-560.
Nayak, et al., "Progress and Prospects: Immune Responses to Viral Vectors", Gene Therapy, Nov. 12, 2009, 17: 295-304.
NCBI, "Beta-2-Microglobin [*Homo sapiens*]", GenBank Accession No. ABB01003.1, 2 Pages, 2005.
NCBI, "Codon Usage Database", Retrieved from <<http://www.kazusa.or.jp/codon/>>, 2013, pp. 1-2.
Neumann, et al., "Gene Transfer Into Mouse Lyoma Cells by Electroporation in High Electric Fields", The EMBO Journal, vol. 1, No. 7, pp. 841-845. (Jul. 1, 1982).
Noren et al. (1989) "A General Method for Site-Specific Incorporation of Unnatural Amino Acids into Proteins," Science, 244: 182-188.
Notice of Opposition for European Patent Application No. 14751254.5, mailed Aug. 23, 2021, 40 pages.
Partial European Search Report for European Patent Application No. 15814881.7, mailed on Jan. 12, 2018, 6 pages.
Peyvandi, F., et al., "Genetic Diagnosis of Gaemophilia and Other Inherited Bleeding Disorders," Haemophilia 12(Suppl 3):82-89, Blackwell Publishing Ltd., England (2006).
Pipe et al., "Functional Factor VIII Made With Von Willebrand Factor at High Levels in Transgenic Milk", Journal of Thrombosis and Haemostasis, Nov. 2011, vol. 9, No. 11, pp. 2235-2242.
Podust, "Extension of In Vivo Half-Life of Biologically Active Molecules by XTEN Protein Polymers", Journal of Controlled Release, Oct. 28, 2016, 240(6): 52-66.
Ritchie, et al. (Dec. 6, 1984) "Allelic Exclusion and Control of Endogenous Immunoglobulin Gene Rearrangement in κ Transgenic Mice", Nature, vol. 312, No. 5994, pp. 517-520.
Robl, et al. (Jan. 1, 2003) "Artificial Chromosome Vectors and Expression of Complex Proteins in Transgenic Animals", Theriogenology, vol. 59, Issue 1, pp. 107-113.
Rodriguez-Merchan, E.C. "Management of Musculoskeletal Complications of Hemophilia," Seminars in Thrombosis and Hemostasis 29(1):87-96, Thieme, United States (2003).
Roovers et al. (2007) "Efficient inhibition of EGFR signalling and of tumour growth by antagonistic anti-EGFR Nanobodies," Cacer Immunol Immunother, 56:303-317.
Routledge et al. (1995) "The Effect of Aglycosylation on the Immunogenicity of a Humanized Therapeutic CD3 Monoclonal Antibody," Transplantation, 60 (8): 847-853.
Ruberti et al. (1994) "The use of the RACE method to clone hybridoma cDNA when V region primers fail," Journal of Immunological Methods, 173: 33-39.
Ruther et al., "Easy Identification of cDNA Clones," The EMBO Journal 2(10): 1791-1794, IRL Press Ltd, England (1983).
Rutledge et al. (1998) "Infectious Clones and Vectors Derived from Adeno-Associated Virus (AAV) Serotypes Other Than AAV Type 2," Journal of Virology, 72(1):309-319.
Sandberg et al., "Structural and Functional Characterization of B-Domain Deleted Recombinant Factor VIII", Seminars in Hematology, Apr. 2001, 38(2), Suppl 4: 4-12.
Sarver, N., et al., "Stable Expression of Recombinant Factor VIII Molecules Using a Bovine Papillomavirus Vector," DNA 6(6):553-564, Mary Ann Liebert, Inc., United States (1987).
Schlapschy, et al., "Fusion of a Recombinant Antibody Fragment with a Homo-Amino-Acid Polymer: Effects on Biophysical Properties and Prolonged Plasma Half-Life", Protein Engineering, Design and Selection, vol. 20, No. 6, pp. 273-284, Jun. 1, 2007.
Sebastian et al., "Treatment of malignant pleural effusion with the trifunctional antibody catumaxomab (Removab) (anti-EpCAM x Anti-CD3): results of a phase 1/2 study", Journal of Immunotherapy, 2009, 32(2): 195-202.
Sequence alignment of Seq ID No. 1 of the opposed patent and Seq ID Nos. 5, 6, and 4 of D2, Retrieved Aug. 2, 2021.
Sequence alignment of Seq ID Nos. 3 and 1 of the opposed patent original file name, Retrieved Aug. 2, 2021.
Sharp et al. (1987) "The codon adaptation index—a measure of directional synonymous codon usage bias, and its potential applications," Nucleic Acids Research, 15 (3): 1281-1295.

(56) References Cited

OTHER PUBLICATIONS

Shields et al. (2001) "High Resolution Mapping of the Binding Site on Human IgG1 for FcγRI, FcγRII, FcγRIII, and FcRn and Design of IgG1 Variants with Improved Binding to the FcγR," J. Biol. Chem., 276 (9) 6591-6604.
Simioni, et al. (Oct. 22, 2009) "X-Linked Thrombophilia with a Mutant Factor IX (Factor IX Padua)", The New England Journal of Medicine, vol. 361, No. 17, pp. 1671-1675.
Sosale, et al., "Marker of Self CD47 on Lentiviral Vectors Decreases Macrophage-Mediated Clearance and Increases Delivery to SIRPA-Expressing Lung Carcinoma Tumors", Molecular Therapy-Methods & Clinical Development, vol. 3, No. 16080, 13 Pages, Jan. 1, 2016.
Srivastava et al. (1983) "Nucleotide Sequence and Organization of the Adeno-Associated Virus 2 Genome," Journal of Virology, 45(2):555-564.
Story et al. (1994) "A Major Histocompatibility Complex Class I-like Fc Receptor Cloned from Human Placenta: Possible Role in Transfer of Immunoglobulin G from Mother to Fetus," J. Exp. Med., Brief Definitive Report, 180: 2377-2381.
Strohl, "Fusion Proteins for Half-Life Extension of Biologics as a Strategy to Make Biobetters", BioDrugs, 2015, 29: 215-239.
Summons to Attend Oral Proceedings for European Patent Application No. 14751254.5, mailed Nov. 9, 2022.
Supplementary European Search Report for European Patent Application No. 15814881.7, mailed on Apr. 13, 2015, 7 pages.
Suwanmanee et al., "Integration-Deficient Lentiviral Vectors Expressing Codon-Optimized R338L Human FIX Restore Normal Hemostasis in Hemophilia B Mice", Molecular Therapy, 2014, vol. 22, No. 3, pp. 567-574.
Swystun, et al., "Gene Therapy for Coagulation Disorders", Circulation Research, vol. 118, No. 9, pp. 1443-1452, Apr. 29, 2016.
Third party observations against European Application No. 15814881.7, dated Oct. 2, 2020, 107 pages.
Toole, et al., "A Large Region (Approximately Equal to 95 kDa) of Human Factor VIII Is Dispensable for In Vitro Procoagulant Activity", Proceedings of the National Academy of Sciences, vol. 83, No. 16, pp. 5939-5942, Aug. 1, 1986.
Torres-Torronteras et al. (2014) "Gene Therapy Using a Liver-targeted AAV Vector Restores Nucleoside and Nucleotide Homeostasis in a Murine Model of MNGIE," Molecular Therapy, 22(5):901-907.
Trüssel et al. (2009) "New Strategy for the Extension of the Serum Half-Life of Antibody Fragments," Bioconjugate Chem., 20:2286-2292.
Vehar et al., "Structure of Human Factor VIII", Nature, Nov. 22, 1984; 312(5992): 337-342.
Wagner, et al. (Oct. 1, 1981) "Microinjection of a Rabbit Beta-Globin Gene into Zygotes and Its Subsequent Expression in Adult Mice and Their Offspring", Proceedings of the National Academy of Sciences of the United States of America, vol. 78, No. 10, pp. 6376-6380.
Ward et al., "Codon Optimization of Human Factor VIII cDNAs Leads to High-Level Expression", Blood, Jan. 20, 2011, 117(3): 798-807.
Ward, et al., "The Effector Functions of Immunoglobulins: Implications for Therapy", Therapeutic immunology, vol. 2, No. 2, pp. 77-94. (Apr. 1995).
White, G.C. II, et al., "A Multicenter Study of Recombinant Factor VIII (Recombinate(TM)) in Previously Treated Patients with Hemophilia A," Thrombosis and Haemostasis 77(4):660-667, F.K. Schattauer Verlagsgesellschaft mbH, Germany (1997).
Wigler, et al., "Biochemical Transfer of Single-Copy Eucaryotic Genes using Total Cellular DNA as Donor", Cell, vol. 14, No. 3, pp. 725-731. (Jul. 1978).
Wu et al. (2000) "Mutational Analysis of the Adeno-Associated Virus Type 2 (AAV2) Capsid Gene and Construction of AAV2 Vectors with Altered Tropism," Journal of Virology, 74(18):8635-8647.
Zhang et al., "An EpCAM/CD3 bispecific antibody efficiently eliminates hepatocellular carcinoma cells with limited galectin-1 expression", Cancer Immunology, Immunotherapy, 2014, 63(2): 121-132.
Akkina, et al., High-efficiency Gene Transfer Into CD34+ Cells With a Human Immunodeficiency Virus Type 1-based Retroviral Vector Pseudotyped With Vesicular Stomatitis Virus Envelope Glycoprotein G, Journal of Virology, vol. 70, No. 4, pp. 2581-2585, Apr. 1996.
Brown, et al., Endogenous microRNA Regulation Suppresses Transgene Expression in Hematopoietic Lineages and Enables Stable Gene Transfer, Nature Medicine, vol. 12, No. 5, pp. 585-591, May 1, 2006.
Chen, et al., MicroRNAs as Regulators of Mammalian Hematopoiesis, Seminars in Immunology, vol. 17, No. 2, pp. 155-165, Apr. 1, 2005.
Coffin, et al., The Interactions of Retroviruses and Their Hosts, Retroviruses, Cold Spring Harbor Laboratory Press Eds: JM Coffin, S M Hughes, HE Varmus, pp. 758-763, 1997.
Costa, et al., Transcriptional Control of the Mouse Prealbumin (Transthyretin) Gene: Both Promoter Sequences and a Distinct Enhancer Are Cell Specific, Molecular and Cellular Biology, vol. 6, No. 12, pp. 4697-4708, Jan. 1, 1986.
Dull, et al., A Third-Generation Lentivirus Vector with a Conditional Packaging System, Journal of Virology, vol. 72, No. 11, pp. 8463-8471, Nov. 1, 1998.
Figueiredo, et al., Cis-Acting Elements and Transcription Factors Involved in the Promoter Activity of the Human Factor VIII Gene, Journal of Biological Chemistry, vol. 270, No. 20, pp. 11828-11838, May 19, 1995.
GenBank, Synthetic Construct Hepatocyte-Restricted Expression Cassette, GenBank Accession No. AY661265.1, Retrieved From:<<https://www.ncbi.nlm.nih.gov/nuccore/AY661265>>, 2 Pages., Sep. 29, 2009.
Ill, et al., Optimization of the Human Factor VIII Complementary DNA Expression Plasmid for Gene Therapy of Hemophilia A, Blood Coagulation & Fibrinolysis: An International Journal in Haemostasis and Thrombosis, vol. 8, pp. S23-S30, Jan. 1, 1997.
Klimatcheva, et al., Lentiviral Vectors and Gene Therapy, Frontiers in Bioscience, vol. 4, pp. 481-496, Jun. 1, 1999.
Mount, et al., Sustained Phenotypic Correction of Hemophilia B Dogs With a Factor IX Null Mutation by Liver-Directed Gene Therapy, Blood, vol. 99, No. 8, pp. 2670-2676, Apr. 15, 2002.
Rouet, et al., A Potent Enhancer Made of Clustered Liver-Specific Elements in the Transcription Control Sequences of Human Alpha 1-Microglobulin/Bikunin Gene, Journal of Biological Chemistry, vol. 267, No. 29, pp. 20765-20773, Jan. 1, 1992.
Rouet, et al., An Array of Binding Sites for Hepatocyte Nuclear Factor 4 of High and Low Affinities Modulates the Liver-Specific Enhancer for the Human α1-Microglobulin/Bikunin Precursor, Biochemical Journal, vol. 334, No. 3, pp. 577-584, Jan. 1, 1998.
Rouet, et al., Hierarchy and Positive/Negative Interplays of the Hepatocyte Nuclear Factors HNF-1, -3 and- 4 in the Liver-Specific Enhancer for the Human α-1-Microglobulin/Bikunin Precursor, Nucleic Acids Research, vol. 23, No. 3, pp. 395-404, Jan. 1, 1995.
Vigna, et al., Efficient Tet-Dependent Expression of Human Factor IX In Vivo by a New Self-Regulating Lentiviral Vector, Molecular Therapy, vol. 11, No. 5, pp. 763-775, Jan. 1, 2005.
Zufferey, et al., Multiply Attenuated Lentiviral Vector Achieves Efficient Gene Delivery In Vivo, Nature Biotechnology, vol. 15, No. 9, pp. 871-875, Sep. 1, 1997.
Cantore et al., "Liver-directed lentiviral gene therapy in a dog model of hemophilia B", Science Translational Medicine, Mar. 4, 2015, 7(277): 277.
U.S. Appl. No. 18/461,697, filed Sep. 6, 2023, Siyuan Tan, Optimized Factor VIII Gene.
U.S. Appl. No. 16/074,729 2019/0185543 U.S. Pat. No. 11,753,461, filed Aug. 1, 2018 Jun. 20, 2019 Sep. 12, 2023, Siyuan Tan, Optimized Factor VIII Genes.
U.S. Appl. No. 18/364,103, filed Aug. 2, 2023, Siyuan Tan, Optimized Factor VIII Genes.
U.S. Appl. No. 16/965,895 2021/0038744, filed Jul. 29, 2020 Feb. 11, 2021, Andrea Annoni, Use of Lentiviral Vectors Expressing Factor VIII.

(56) References Cited

OTHER PUBLICATIONS

U.S. Appl. No. 16/704,400 2020/0199626, filed Dec. 5, 2019 Jun. 25, 2020, Tongyao Liu, Use of Lentiviral Vectors Expressing Factor VIII.
U.S. Appl. No. 14/767,425, 2015/0361158, U.S. Pat. No. 10,370,431, filed Aug. 12, 2015, Dec. 17, 2015, Aug. 6, 2019, Siyuan Tan, Optimized Factor VIII Gene.
U.S. Appl. No. 16/452,010, 2020/0024327, U.S. Pat. No. 11,787,951, filed Jun. 25, 2019, Jan. 23, 2020, Oct. 17, 2023, Siyuan Tan, Optimized Factor VIII Gene.
U.S. Appl. No. 18/461,697, 2024/0141019, filed Sep. 6, 2023, May 2, 2024, Siyuan Tan, Optimized Factor VIII Gene.
U.S. Appl. No. 15/323,302, 2017/0260516, U.S. Pat. No. 11,008,561, filed Dec. 30, 2016, Sep. 14, 2017, May 18, 2021, Siyuan Tan, Optimized Factor IX Gene.
U.S. Appl. No. 17/060,759, 2021/0115425, filed Oct. 1, 2020, Apr. 22, 2021, Siyuan Tan, Optimized Factor IX Gene.
U.S. Appl. No. 16/074,729, 2019/0185543, U.S. Pat. No. 11,753,461, filed Aug. 1, 2018, Jun. 20, 2019, Sep. 12, 2023, Siyuan Tan, Optimized Factor VIII Gene.
U.S. Appl. No. 18/364,103, 2024/0124555, filed Aug. 2, 2023, Apr. 18, 2024, Siyuan Tan, Optimized Factor VIII Gene.
U.S. Appl. No. 16/965,895, 2021/038744, filed Jul. 29, 2020, Feb. 11, 2021, Andrea Annoni, Use of Lentiviral Vectors Expressing Factor VIII.
U.S. Appl. No. 16/704,400, 2020/0199626, filed Dec. 5, 2019, Jun. 25, 2020, Tongyao Liu, Use of Lentiviral Vectors Expressing Factor IX.
U.S. Appl. No. 17/038,031, 2021/0113634, filed Sep. 30, 2020, Apr. 22, 2021, Andrew Kroetsch, Lentiviral Vector Formulations.
U.S. Appl. No. 17/356,980, 2022/0033849, filed Jun. 24, 2021, Feb. 3, 2022, Mukesh Mayani, Methods for the Purification Of Viral Vectors.
Höfig et al., "Abstract 4144: Improvement of tumor cell transduction with lentiviral vectors using chemical and cell targeting approaches", Cancer Res, Apr. 15, 2013, 73(8_Supplement): 4144.
Masiuk et al., "PGE2 and Poloxamer Synperonic F108 Enhance Transduction of Human HSPCs with a β-Globin Lentiviral Vector", Mol Ther Methods Clin Dev., Apr. 4, 2019, 4(13): 390-398, Epublished Jun. 14, 2019.

\* cited by examiner

SEQUENCE LISTING

<160> NUMBER OF SEQ ID NOS: 7

<210> SEQ ID NO 1
<211> LENGTH: 4371
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1

```
atgcagattg agctgtccac ttgtttcttc ctgtgcctcc tgcgcttctg tttctccgcc      60
actcgccggt actaccttgg agccgtggag ctttcatggg actacatgca gagcgacctg     120
ggcgaactcc ccgtggatgc cagattcccc ccccgcgtgc aaagtccttc ccctttaac     180
acctccgtgg tgtacaagaa aaccctcttt gtcgagttca ctgaccacct gttcaacatc     240
gccaagccgc gcccaccttg gatgggcctc ctgggaccga ccattcaagc tgaagtgtac     300
gacaccgtgg tgatcaccct gaagaacatg gcgtcccacc ccgtgtccct gcatgcggtc     360
ggagtgtcct actggaaggc ctccgaagga gctgagtacg acgaccagac tagccagcgg     420
gaaaaggagg acgataaagt gttcccgggc ggctcgcata cttacgtgtg gcaagtcctg     480
aaggaaaacg gacctatggc atccgatcct ctgtgcctga cttactccta cctttcccat     540
gtggacctcg tgaaggacct gaacagcggg ctgattggtg cacttctcgt gtgccgcgaa     600
ggttcgctcg ctaaggaaaa gacccagacc ctccataagt tcatccttt gttcgctgtg     660
ttcgatgaag gaaagtcatg gcattccgaa actaagaact cgctgatgca ggaccgggat     720
gccgcctcag cccgcgcctg gcctaaaatg catacagtca acggatacgt gaatcggtca     780
ctgcccgggc tcatcggttg tcacagaaag tccgtgtact ggcacgtcat cggcatgggc     840
actacgcctg aagtgcactc catcttcctg gaagggcaca ccttcctcgt gcgcaaccac     900
cgccaggcct ctctggaaat ctccccgatt accttctga ccgcccagac tctgctcatg     960
gacctggggc agttccttct cttctgccac atctccagcc atcagcacga cggaatggaa    1020
gcctacgtga aggtggactc atgcccggaa gaacctcagt tgcggatgaa gaacaacgag    1080
gaggccgagg actatgacga cgatttgact gactccgaga tggacgtcgt gcggttcgat    1140
gacgacaaca gccccagctt catccagatt cgcagcgtgg ccaagaagca ccccaaaacc    1200
tgggtgcact acatcgcggc cgaggaagaa gattgggact acgccccgtt ggtgctggca    1260
cccgatgacc ggtcgtacaa gtcccagtat ctgaacaatg gtccgcagcg gattggcaga    1320
aagtacaaga aagtgcggtt catggcgtac actgacgaaa cgtttaagac ccgggaggcc    1380
attcaacatg agagcggcat tctgggacca ctgctgtacg agaggtcgg cgataccctg    1440
ctcatcatct tcaaaaacca ggcctcccgg cctacaacaa tctaccctca cggaatcacc    1500
gacgtgcggc cactctactc gcggcgcctg ccgaagggcg tcaagcacct gaaagacttc    1560
cctatcctgc cgggcgaaat cttcaagtat aagtggaccg tcaccgtgga ggacgggccc    1620
accaagagcg atcctaggtg tctgactcgg tactactcca gcttcgtgaa catggaacgg    1680
gacctggcat cgggactcat tggaccgctg ctgatctgct acaaagagtc ggtggatcaa    1740
cgcggcaacc agatcatgtc cgacaagcgc aacgtgatcc tgttctccgt gtttgatgaa    1800
aacagatcct ggtacctcac tgaaaacatc cagaggttcc tcccaaaccc cgcaggagtg    1860
caactggagg accctgagtt tcaggcctcg aatatcatgc actcgattaa cggttacgtg    1920
ttcgactcgc tgcagctgag cgtgtgcctc catgaagtcg cttactggta cattctgtcc    1980
atcggcgccc agactgactt cctgagcgtg ttcttttccg gttacacctt taagcacaag    2040
atggtgtacg aagataccct gacctgttc cctttctccg cgaaacggt gttcatgtcg    2100
atggagaacc cgggtctgtg gattctggga tgccacaaca gcgactttcg gaaccgcgga    2160
```

```
atgactgccc tgctgaaggt gtcctcatgc gacaagaaca ccggagacta ctacgaggac    2220
tcctacgagg atatctcagc ctacctcctg tccaagaaca acgcgatcga gccgcgcagc    2280
ttcagccaga acccgcctgt gctgaagagg caccagcgag aaattacccg gaccaccctc    2340
caatcggatc aggaggaaat cgactacgac gacaccatct cggtggaaat gaagaaggaa    2400
gatttcgata tctacgacga ggacgaaaat cagtcccctc gctcattcca aaagaaaact    2460
agacactact ttatcgccgc ggtggaaaga ctgtgggact atggaatgtc atccagccct    2520
cacgtccttc ggaaccgggc ccagagcgga tcggtgcctc agttcaagaa agtggtgttc    2580
caggagttca ccgacggcag cttcacccag ccgctgtacc gggagaact gaacgaacac    2640 ctgggcctgc tcggtcccta catccgcgcg gaagtggagg ataacatcat ggtgaccttc    2700
cgtaaccaag catccagacc ttactccttc tattcctccc tgatctcata cgaggaggac    2760
cagcgccaag gcgccgagcc ccgcaagaac ttcgtcaagc ccaacgagac taagacctac    2820
ttctggaagg tccaacacca tatggccccg accaaggatg agtttgactg caaggcctgg    2880
gcctacttct ccgacgtgga ccttgagaag gatgtccatt ccggcctgat cgggccgctg    2940
ctcgtgtgtc acaccaacac cctgaaccca gcgcatggac gccaggtcac cgtccaggag    3000
tttgctctgt tcttcaccat ttttgacgaa actaagtcct ggtacttcac cgagaatatg    3060
gagcgaaact gtagagcgcc ctgcaatatc cagatggaag atccgacttt caaggagaac    3120
tatagattcc acgccatcaa cggtacatc atggatactc tgccggggct ggtcatggcc    3180
caggatcaga ggattcggtg gtacttgctg tcaatgggat cgaacgaaaa cattcactcc    3240
attcacttct ccggtcacgt gttcactgtg cgcaagaagg aggagtacaa gatggcgctg    3300
tacaatctgt accccggggt gttcgaaact gtggagatgc tgccgtccaa ggccggcatc    3360
tggagagtgg agtgcctgat cggagagcac ctccacgcgg ggatgtccac cctcttcctg    3420
gtgtactcga ataagtgcca gaccccgctg gcatggcct cgggccacat cagagacttc    3480
cagatcacag caagcggaca atacggccaa tgggcgccga agctggcccg cttgcactac    3540
tccggatcga tcaacgcatg gtccaccaag gaaccgttct cgtggattaa ggtgacctc    3600 ctggccccta tgattatcca cggaattaag acccagggcg ccaggcagaa gttctcctcc    3660
ctgtacatct cgcaattcat catcatgtac agcctggacg ggaagaagtg gcagacttac    3720
aggggaaact ccaccggcac cctgatggtc tttttcggca acgtggattc ctccggcatt    3780
aagcacaaca tcttcaaccc accgatcata gccagatata ttaggctcca ccccactcac    3840
tactcaatcc gctcaactct tcggatggaa ctcatggggt gcgacctgaa ctcctgctcc    3900
atgccgttgg ggatggaatc aaaggctatt agcgacgccc agatcaccgc gagctcctac    3960
ttcactaaca tgttcgccac ctggagcccc tccaaggcca ggctgcactt gcagggacgg    4020
tcaaatgcct ggcggccgca agtgaacaat ccgaaggaat ggcttcaagt ggatttccaa    4080
aagaccatga aagtgaccgg agtcaccacc caggagtga agtcccttct gacctcgatg    4140
tatgtgaagg agttcctgat tagcagcagc caggacgggc accagtggac cctgttcttc    4200
caaaacggaa aggtcaaggt gttccagggg aaccaggact cgttcacacc cgtggtgaac    4260
tccctggacc ccccactgct gacgcggtac ttgaggattc atcctcagtc ctgggtccat    4320
cagattgcat tgcgaatgga agtcctgggc tgcgaggccc aggacctgta c    4371
```

<210> SEQ ID NO 2
<211> LENGTH: 4812
<212> TYPE: DNA

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2

| | |
|---|---|
| atgcagattg agctgtccac ttgtttcttc ctgtgcctcc tgcgcttctg tttctccgcc | 60 |
| actcgccggt actaccttgg agccgtggag cttTcatggg actacatgca gagcgacctg | 120 |
| ggcgaactcc ccgtggatgc cagattcccc ccccgcgtgc caaagtcctt ccccttTaac | 180 |
| acctccgtgg tgtacaagaa aaccctcttt gtcgagttca ctgaccacct gttcaacatc | 240 |
| gccaagccgc gcccaccttg gatgggcctc ctgggaccga ccattcaagc tgaagtgtac | 300 |
| gacaccgtgg tgatcaccct gaagaacatg gcgtcccacc ccgtgtccct gcatgcggtc | 360 |
| ggagtgtcct actggaaggc ctccgaagga gctgagtacg acgaccagac tagccagcgg | 420 |
| gaaaaggagg acgataaagt gttcccgggc ggctcgcata cttacgtgtg gcaagtcctg | 480 |
| aaggaaaacg gacctatggc atccgatcct ctgtgcctga cttactccta cctttcccat | 540 |
| gtggacctcg tgaaggacct gaacagcggg ctgattggtg cacttctcgt gtgccgcgaa | 600 |
| ggttcgctcg ctaaggaaaa gacccagacc ctccataagt tcatccttTt gttcgctgtg | 660 |
| ttcgatgaag gaaagtcatg gcattccgaa actaagaact cgctgatgca ggaccgggat | 720 |
| gccgcctcag cccgcgcctg gcctaaaatg catacagtca acggatacgt gaatcggtca | 780 |
| ctgcccgggc tcatcggttg tcacagaaag tccgtgtact ggcacgtcat cggcatgggc | 840 |
| actacgcctg aagtgcactc catcttcctg gaagggcaca ccttcctcgt gcgcaaccac | 900 |
| cgccaggcct ctctggaaat ctccccgatt acctttctga ccgcccagac tctgctcatg | 960 |
| gacctggggc agttccttct cttctgccac atctccagcc atcagcacga cggaatggag | 1020 |
| gcctacgtga aggtggactc atgcccggaa gaacctcagt tgcggatgaa gaacaacgag | 1080 |
| gaggccgagc actatgacga cgatttgact gactccgaga tggacgtcgt gcggttcgat | 1140 |
| gacgacaaca gccccagctt catccagatt cgcagcgtgg ccaagaagca ccccaaaacc | 1200 |
| tgggtgcact acatcgcggc cgaggaagaa gattgggact acgccccgtt ggtgctggca | 1260 |
| cccgatgacc ggtcgtacaa gtcccagtat ctgaacaatg gtccgcagcg gattggcaga | 1320 |
| aagtacaaga aagtgcggtt catggcgtac actgacgaaa cgtttaagac ccgggaggcc | 1380 |
| attcaacatg agagcggcat tctgggacca ctgctgtacg agaggtcgg cgataccctg | 1440 |
| ctcatcatct tcaaaaacca ggcctcccgg cctacaacaa tctaccctca cggaatcacc | 1500 |
| gacgtgcggc cactctactc gcggcgcctg ccgaagggcg tcaagcacct gaaagacttc | 1560 |
| cctatcctgc cgggcgaaat cttcaagtat aagtggaccg tcaccgtgga ggacgggccc | 1620 |
| accaagagcg atcctaggtg tctgactcgg tactactcca gcttcgtgaa catggaacgg | 1680 |
| gacctggcat cgggactcat tggaccgctg ctgatctgct acaaagagtc ggtggatcaa | 1740 |
| cgcggcaacc agatcatgtc cgacaagcgc aacgtgatcc tgttctccgt gtttgatgaa | 1800 |
| aacagatcct ggtacctcac tgaaaacatc cagaggttcc tcccaaaccc cgcaggagtg | 1860 |
| caactggagg accctgagtt tcaggcctcg aatatcatgc actcgattaa cggttacgtg | 1920 |
| ttcgactcgc tgcagctgag cgtgtgcctc catgaagtcg cttactggta cattctgtcc | 1980 |
| atcggcgccc agactgactt cctgagcgtg ttctttTccg gttacacctt taagcacaag | 2040 |
| atggtgtacg aagatacccc tgaccctgtt ccctttctccg cgaaacggt gttcatgtcg | 2100 |
| atggagaacc cgggtctgtg gattctggga tgccacaaca gcgactttcg gaaccgcgga | 2160 |

```
atgactgccc tgctgaaggt gtcctcatgc gacaagaaca ccggagacta ctacgaggac    2220
tcctacgagg atatctcagc ctacctcctg tccaagaaca acgcgatcga gccgcgcagc    2280
ttcagccaga acacatcaga gagcgccacc cctgaaagtg gtcccgggag cgagccagcc    2340
acatctgggt cggaaacgcc aggcacaagt gagtctgcaa ctcccgagtc cggacctggc    2400
tccgagcctg ccactagcgg ctccgagact ccgggaactt ccgagagcgc tacaccagaa    2460
agcggacccg gaaccagtac cgaacctagc gagggctctg ctccgggcag cccagccggc    2520
tctcctacat ccacggagga gggcacttcc gaatccgcca ccccggagtc agggccagga    2580
tctgaacccg ctacctcagg cagtgagacg ccaggaacga gcgagtccgc tacaccggag    2640
agtgggccag ggagccctgc tggatctcct acgtccactg aggaagggtc accagcgggc    2700
tcgcccacca gcactgaaga aggtgcctcg agcccgcctg tgctgaagag caccagcga    2760 gaaattaccc ggaccaccct ccaatcggat caggaggaaa tcgactacga cgacaccatc    2820
tcggtggaaa tgaagaagga agatttcgat atctacgacg aggacgaaaa tcagtccct    2880 cgctcattcc aaaagaaaac tagacactac tttatcgccg cggtggaaag actgtgggac    2940 tatgaatgt catccagccc tcacgtcctt cggaaccggg cccagagcgg atcggtgcct    3000
cagttcaaga aagtggtgtt ccaggagttc accgacggca gcttcaccca gccgctgtac    3060
cggggagaac tgaacgaaca cctgggcctg ctcggtccct acatccgcgc ggaagtggag    3120
gataacatca tggtgacctt ccgtaaccaa gcatccagac cttactcctt ctattcctcc    3180
ctgatctcat acgaggagga ccagcgccaa ggcgccgagc cccgcaagaa cttcgtcaag    3240
cccaacgaga ctaagaccta cttctggaag gtccaacacc atatggcccc gaccaaggat    3300
gagtttgact gcaaggcctg ggcctacttc tccgacgtgg accttgagaa ggatgtccat    3360
tccggcctga tcgggccgct gctcgtgtgt cacaccaaca ccctgaaccc agcgcatgga    3420
cgccaggtca ccgtccagga gtttgctctg ttcttcacca tttttgacga aactaagtcc    3480
tggtacttca ccgagaatat ggagcgaaac tgtagagcgc cctgcaatat ccagatggaa    3540
gatccgactt tcaaggagaa ctatagattc cacgccatca acgggtacat catggatact    3600
ctgccggggc tggtcatggc ccaggatcag aggattcggt ggtacttgct gtcaatggga    3660
tcgaacgaaa acattcactc cattcacttc tccggtcacg tgttcactgt gcgcaagaag    3720
gaggagtaca agatggcgct gtacaatctg taccccgggg tgttcgaaac tgtggagatg    3780
ctgccgtcca aggccggcat ctggagagtg gagtgcctga tcggagagca cctccacgcg    3840
gggatgtcca ccctcttcct ggtgtactcg aataagtgcc agaccccgct gggcatggcc    3900
tcgggccaca tcagagactt ccagatcaca gcaagcggac aatacggcca atgggcgccg    3960
aagctggccc gcttgcacta ctccggatcg atcaacgcat ggtccaccaa ggaaccgttc    4020
tcgtggatta aggtggacct cctggcccct atgattatcc acggaattaa gacccagggc    4080
gccaggcaga agttctcctc cctgtacatc tcgcaattca tcatcatgta cagcctggac    4140
gggaagaagt ggcagactta caggggaaac tccaccggca ccctgatggt cttttcggc    4200 aacgtggatt cctccggcat taagcacaac atcttcaacc caccgatcat agccagatat    4260
attaggctcc accccactca ctactcaatc cgctcaactc ttcggatgga actcatgggg    4320
tgcgacctga actcctgctc catgccgttg gggatggaat caaaggctat tagcgacgcc    4380
cagatcaccg cgagctccta cttcactaac atgttcgcca cctggagccc ctccaaggcc    4440
aggctgcact tgcagggacg gtcaaatgcc tggcggccgc aagtgaacaa tccgaaggaa    4500
```

| | |
|---|---|
| tggcttcaag tggatttcca aaagaccatg aaagtgaccg agtcaccac ccagggagtg | 4560 |
| aagtcccttc tgacctcgat gtatgtgaag gagttcctga ttagcagcag ccaggacggg | 4620 |
| caccagtgga ccctgttctt ccaaaacgga aaggtcaagg tgttccaggg gaaccaggac | 4680 |
| tcgttcacac ccgtggtgaa ctccctggac cccccactgc tgacgcggta cttgaggatt | 4740 |
| catcctcagt cctgggtcca tcagattgca ttgcgaatgg aagtcctggg ctgcgaggcc | 4800 |
| caggacctgt ac | 4812 |

```
<210> SEQ ID NO 3
<211> LENGTH: 1383
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 3
```

| | |
|---|---|
| atgcagagag tcaacatgat tatggctgag tcacctgggc tgattactat ttgcctgctg | 60 |
| ggctacctgc tgtccgccga gtgtaccgtg ttcctggacc atgagaacgc aaataagatc | 120 |
| ctgaacaggc ccaaaagata caatagtggg aagctggagg aatttgtgca gggcaacctg | 180 |
| gagagagaat gcatggagga aaagtgtagc ttcgaggaag cccgcgaggt gtttgaaaat | 240 |
| acagagcgaa ccacagagtt ctggaagcag tatgtggacg gcgatcagtg cgagagcaac | 300 |
| ccctgtctga atggcggaag ttgcaaagac gatatcaact catacgaatg ctggtgtcct | 360 |
| ttcgggtttg aaggcaaaaa ttgcgagctg gacgtgacat gtaacattaa gaatggacgg | 420 |
| tgcgagcagt tttgtaaaaa ctctgccgat aataaggtgg tgtgcagctg tactgaagga | 480 |
| tatcgcctgg ctgagaacca gaagtcctgc gaaccagcag tgcccttccc ttgtgggagg | 540 |
| gtgagcgtct cccagacttc aaaactgacc agagcagaga cagtgttttcc cgacgtggat | 600 |
| tacgtcaaca gcactgaggc cgaaaccatc ctggacaaca ttactcagtc tacccagagt | 660 |
| ttcaatgact ttactcgggt ggtcgggggc gaggatgcta aaccaggcca gttccccctgg | 720 |
| caggtggtcc tgaacggaaa ggtggatgca ttttgcggag gtctatcgt gaatgagaaa | 780 |
| tggattgtca ccgccgctca ctgcgtggaa accggagtca agatcacagt ggtcgctggg | 840 |
| gagcacaaca ttgaggaaac agaacatact gagcagaagc ggaatgtgat ccgcatcatt | 900 |
| cctcaccata actacaatgc agccatcaac aaatacaatc atgacattgc cctgctggaa | 960 |
| ctggatgagc tctggtgct gaacagctac gtcactccaa tctgcattgc tgacaaagag | 1020 |
| tataccaata tcttcctgaa gtttggatca gggtacgtga gcggctgggg aagagtcttc | 1080 |
| cacaagggca ggagcgccct ggtgctccag tatctgcgag tgcctctggt cgatcgagct | 1140 |
| acctgtctgc tctctaccaa gtttacaatc tacaacaaca tgttctgcgc tgggtttcac | 1200 |
| gagggaggac gagactcctg tcagggcgat tctgggggcc acatgtgac agaggtcgaa | 1260 |
| ggcaccagct tcctgactgg catcatttcc tggggagagg aatgtgcaat gaagggaaaa | 1320 |
| tacgggatct acaccaaagt gagccgctat gtgaactgga tcaaggaaaa aaccaaactg | 1380 |
| acc | 1383 |

```
<210> SEQ ID NO 4
<211> LENGTH: 2332
<212> TYPE: PRT
<213> ORGANISM: Homo sapiens

<400> SEQUENCE: 4
```

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
50                      55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
            355                 360                 365

Ile Gln Ile Arg Ser Val Ala Lys Lys His Pro Lys Thr Trp Val His
            370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415
```

-continued

```
Gln Arg Ile Gly Arg Lys Tyr Lys Val Arg Phe Met Ala Tyr Thr
                420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
        755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
```

-continued

```
                835                 840                 845
Phe Thr Pro Glu Ser Gly Leu Gln Leu Arg Leu Asn Glu Lys Leu Gly
    850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
            900                 905                 910
Tyr Asp Ser Gln Leu Asp Thr Thr Leu Phe Gly Lys Lys Ser Ser Pro
                915                 920                 925
Leu Thr Glu Ser Gly Gly Pro Leu Ser Leu Ser Glu Glu Asn Asn Asp
    930                 935                 940
Ser Lys Leu Leu Glu Ser Gly Leu Met Asn Ser Gln Glu Ser Ser Trp
945                 950                 955                 960
Gly Lys Asn Val Ser Ser Thr Glu Ser Gly Arg Leu Phe Lys Gly Lys
                965                 970                 975
Arg Ala His Gly Pro Ala Leu Leu Thr Lys Asp Asn Ala Leu Phe Lys
            980                 985                 990
Val Ser Ile Ser Leu Leu Lys Thr  Asn Lys Thr Ser Asn  Asn Ser Ala
        995                 1000                 1005
Thr Asn Arg Lys Thr His Ile Asp Gly Pro Ser Leu  Leu Ile Glu
    1010                 1015                 1020
Asn Ser  Pro Ser Val Trp Gln  Asn Ile Leu Glu Ser  Asp Thr Glu
    1025                 1030                 1035
Phe Lys  Lys Val Thr Pro Leu  Ile His Asp Arg Met  Leu Met Asp
    1040                 1045                 1050
Lys Asn  Ala Thr Ala Leu Arg  Leu Asn His Met Ser  Asn Lys Thr
    1055                 1060                 1065
Thr Ser  Ser Lys Asn Met Glu  Met Val Gln Gln Lys  Lys Glu Gly
    1070                 1075                 1080
Pro Ile  Pro Pro Asp Ala Gln  Asn Pro Asp Met Ser  Phe Phe Lys
    1085                 1090                 1095
Met Leu  Phe Leu Pro Glu Ser  Ala Arg Trp Ile Gln  Arg Thr His
    1100                 1105                 1110
Gly Lys  Asn Ser Leu Asn Ser  Gly Gln Gly Pro Ser  Pro Lys Gln
    1115                 1120                 1125
Leu Val  Ser Leu Gly Pro Glu  Lys Ser Val Glu Gly  Gln Asn Phe
    1130                 1135                 1140
Leu Ser  Glu Lys Asn Lys Val  Val Val Gly Lys Gly  Glu Phe Thr
    1145                 1150                 1155
Lys Asp  Val Gly Leu Lys Glu  Met Val Phe Pro Ser  Ser Arg Asn
    1160                 1165                 1170
Leu Phe  Leu Thr Asn Leu Asp  Asn Leu His Glu Asn  Asn Thr His
    1175                 1180                 1185
Asn Gln  Glu Lys Lys Ile Gln  Glu Glu Ile Glu Lys  Lys Glu Thr
    1190                 1195                 1200
Leu Ile  Gln Glu Asn Val Val  Leu Pro Gln Ile His  Thr Val Thr
    1205                 1210                 1215
Gly Thr  Lys Asn Phe Met Lys  Asn Leu Phe Leu Leu  Ser Thr Arg
    1220                 1225                 1230
Gln Asn  Val Glu Gly Ser Tyr  Asp Gly Ala Tyr Ala  Pro Val Leu
    1235                 1240                 1245
```

-continued

```
Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr
    1340                1345                1350

Gln Ile Asp Tyr Asn Glu Lys Glu Lys Gly Ala Ile Thr Gln Ser
    1355                1360                1365

Pro Leu Ser Asp Cys Leu Thr Arg Ser His Ser Ile Pro Gln Ala
    1370                1375                1380

Asn Arg Ser Pro Leu Pro Ile Ala Lys Val Ser Ser Phe Pro Ser
    1385                1390                1395

Ile Arg Pro Ile Tyr Leu Thr Arg Val Leu Phe Gln Asp Asn Ser
    1400                1405                1410

Ser His Leu Pro Ala Ala Ser Tyr Arg Lys Lys Asp Ser Gly Val
    1415                1420                1425

Gln Glu Ser Ser His Phe Leu Gln Gly Ala Lys Lys Asn Asn Leu
    1430                1435                1440

Ser Leu Ala Ile Leu Thr Leu Glu Met Thr Gly Asp Gln Arg Glu
    1445                1450                1455

Val Gly Ser Leu Gly Thr Ser Ala Thr Asn Ser Val Thr Tyr Lys
    1460                1465                1470

Lys Val Glu Asn Thr Val Leu Pro Lys Pro Asp Leu Pro Lys Thr
    1475                1480                1485

Ser Gly Lys Val Glu Leu Leu Pro Lys Val His Ile Tyr Gln Lys
    1490                1495                1500

Asp Leu Phe Pro Thr Glu Thr Ser Asn Gly Ser Pro Gly His Leu
    1505                1510                1515

Asp Leu Val Glu Gly Ser Leu Leu Gln Gly Thr Glu Gly Ala Ile
    1520                1525                1530

Lys Trp Asn Glu Ala Asn Arg Pro Gly Lys Val Pro Phe Leu Arg
    1535                1540                1545

Val Ala Thr Glu Ser Ser Ala Lys Thr Pro Ser Lys Leu Leu Asp
    1550                1555                1560

Pro Leu Ala Trp Asp Asn His Tyr Gly Thr Gln Ile Pro Lys Glu
    1565                1570                1575

Glu Trp Lys Ser Gln Glu Lys Ser Pro Glu Lys Thr Ala Phe Lys
    1580                1585                1590

Lys Lys Asp Thr Ile Leu Ser Leu Asn Ala Cys Glu Ser Asn His
    1595                1600                1605

Ala Ile Ala Ala Ile Asn Glu Gly Gln Asn Lys Pro Glu Ile Glu
    1610                1615                1620

Val Thr Trp Ala Lys Gln Gly Arg Thr Glu Arg Leu Cys Ser Gln
    1625                1630                1635
```

| | | | | | | | | | | | |
|---|---|---|---|---|---|---|---|---|---|---|---|
|Asn|Pro|Pro|Val|Leu|Lys|Arg|His|Gln|Arg|Glu|Ile|Thr|Arg|Thr|
|1640| | | | |1645| | | |1650| | | | | |

Thr Leu Gln Ser Asp Gln Glu Glu Ile Asp Tyr Asp Asp Thr Ile
1655 1660 1665

Ser Val Glu Met Lys Lys Glu Asp Phe Asp Ile Tyr Asp Glu Asp
1670 1675 1680

Glu Asn Gln Ser Pro Arg Ser Phe Gln Lys Lys Thr Arg His Tyr
1685 1690 1695

Phe Ile Ala Ala Val Glu Arg Leu Trp Asp Tyr Gly Met Ser Ser
1700 1705 1710

Ser Pro His Val Leu Arg Asn Arg Ala Gln Ser Gly Ser Val Pro
1715 1720 1725

Gln Phe Lys Lys Val Val Phe Gln Glu Phe Thr Asp Gly Ser Phe
1730 1735 1740

Thr Gln Pro Leu Tyr Arg Gly Glu Leu Asn Glu His Leu Gly Leu
1745 1750 1755

Leu Gly Pro Tyr Ile Arg Ala Glu Val Glu Asp Asn Ile Met Val
1760 1765 1770

Thr Phe Arg Asn Gln Ala Ser Arg Pro Tyr Ser Phe Tyr Ser Ser
1775 1780 1785

Leu Ile Ser Tyr Glu Glu Asp Gln Arg Gln Gly Ala Glu Pro Arg
1790 1795 1800

Lys Asn Phe Val Lys Pro Asn Glu Thr Lys Thr Tyr Phe Trp Lys
1805 1810 1815

Val Gln His His Met Ala Pro Thr Lys Asp Glu Phe Asp Cys Lys
1820 1825 1830

Ala Trp Ala Tyr Phe Ser Asp Val Asp Leu Glu Lys Asp Val His
1835 1840 1845

Ser Gly Leu Ile Gly Pro Leu Leu Val Cys His Thr Asn Thr Leu
1850 1855 1860

Asn Pro Ala His Gly Arg Gln Val Thr Val Gln Glu Phe Ala Leu
1865 1870 1875

Phe Phe Thr Ile Phe Asp Glu Thr Lys Ser Trp Tyr Phe Thr Glu
1880 1885 1890

Asn Met Glu Arg Asn Cys Arg Ala Pro Cys Asn Ile Gln Met Glu
1895 1900 1905

Asp Pro Thr Phe Lys Glu Asn Tyr Arg Phe His Ala Ile Asn Gly
1910 1915 1920

Tyr Ile Met Asp Thr Leu Pro Gly Leu Val Met Ala Gln Asp Gln
1925 1930 1935

Arg Ile Arg Trp Tyr Leu Leu Ser Met Gly Ser Asn Glu Asn Ile
1940 1945 1950

His Ser Ile His Phe Ser Gly His Val Phe Thr Val Arg Lys Lys
1955 1960 1965

Glu Glu Tyr Lys Met Ala Leu Tyr Asn Leu Tyr Pro Gly Val Phe
1970 1975 1980

Glu Thr Val Glu Met Leu Pro Ser Lys Ala Gly Ile Trp Arg Val
1985 1990 1995

Glu Cys Leu Ile Gly Glu His Leu His Ala Gly Met Ser Thr Leu
2000 2005 2010

Phe Leu Val Tyr Ser Asn Lys Cys Gln Thr Pro Leu Gly Met Ala
2015 2020 2025

Ser Gly His Ile Arg Asp Phe Gln Ile Thr Ala Ser Gly Gln Tyr

```
                  2030               2035               2040

Gly Gln Trp Ala Pro Lys Leu Ala Arg Leu His Tyr Ser Gly Ser
        2045               2050               2055

Ile Asn Ala Trp Ser Thr Lys Glu Pro Phe Ser Trp Ile Lys Val
        2060               2065               2070

Asp Leu Leu Ala Pro Met Ile Ile His Gly Ile Lys Thr Gln Gly
        2075               2080               2085

Ala Arg Gln Lys Phe Ser Ser Leu Tyr Ile Ser Gln Phe Ile Ile
        2090               2095               2100

Met Tyr Ser Leu Asp Gly Lys Lys Trp Gln Thr Tyr Arg Gly Asn
        2105               2110               2115

Ser Thr Gly Thr Leu Met Val Phe Phe Gly Asn Val Asp Ser Ser
        2120               2125               2130

Gly Ile Lys His Asn Ile Phe Asn Pro Pro Ile Ile Ala Arg Tyr
        2135               2140               2145

Ile Arg Leu His Pro Thr His Tyr Ser Ile Arg Ser Thr Leu Arg
        2150               2155               2160

Met Glu Leu Met Gly Cys Asp Leu Asn Ser Cys Ser Met Pro Leu
        2165               2170               2175

Gly Met Glu Ser Lys Ala Ile Ser Asp Ala Gln Ile Thr Ala Ser
        2180               2185               2190

Ser Tyr Phe Thr Asn Met Phe Ala Thr Trp Ser Pro Ser Lys Ala
        2195               2200               2205

Arg Leu His Leu Gln Gly Arg Ser Asn Ala Trp Arg Pro Gln Val
        2210               2215               2220

Asn Asn Pro Lys Glu Trp Leu Gln Val Asp Phe Gln Lys Thr Met
        2225               2230               2235

Lys Val Thr Gly Val Thr Thr Gln Gly Val Lys Ser Leu Leu Thr
        2240               2245               2250

Ser Met Tyr Val Lys Glu Phe Leu Ile Ser Ser Ser Gln Asp Gly
        2255               2260               2265

His Gln Trp Thr Leu Phe Phe Gln Asn Gly Lys Val Lys Val Phe
        2270               2275               2280

Gln Gly Asn Gln Asp Ser Phe Thr Pro Val Val Asn Ser Leu Asp
        2285               2290               2295

Pro Pro Leu Leu Thr Arg Tyr Leu Arg Ile His Pro Gln Ser Trp
        2300               2305               2310

Val His Gln Ile Ala Leu Arg Met Glu Val Leu Gly Cys Glu Ala
        2315               2320               2325

Gln Asp Leu Tyr
        2330

<210> SEQ ID NO 5
<211> LENGTH: 1604
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30
```

```
Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
 50                  55                  60

Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                     85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
                115                 120                 125

Glu Gly Ala Glu Tyr Asp Asp Gln Thr Ser Gln Arg Glu Lys Glu Asp
        130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                    165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
        210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                    245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                    325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445
```

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Thr Ser Glu Ser
            755                 760                 765

Ala Thr Pro Glu Ser Gly Pro Gly Ser Glu Pro Ala Thr Ser Gly Ser
770                 775                 780

Glu Thr Pro Gly Thr Ser Glu Ser Ala Thr Pro Glu Ser Gly Pro Gly
785                 790                 795                 800

Ser Glu Pro Ala Thr Ser Gly Ser Glu Thr Pro Gly Thr Ser Glu Ser
                805                 810                 815

Ala Thr Pro Glu Ser Gly Pro Gly Thr Ser Thr Glu Pro Ser Glu Gly
            820                 825                 830

Ser Ala Pro Gly Ser Pro Ala Gly Ser Pro Thr Ser Thr Glu Glu Gly
            835                 840                 845

Thr Ser Glu Ser Ala Thr Pro Glu Ser Gly Pro Gly Ser Glu Pro Ala
850                 855                 860

Thr Ser Gly Ser Glu Thr Pro Gly Thr Ser Glu Ser Ala Thr Pro Glu

```
            865                 870                 875                 880
        Ser Gly Pro Gly Ser Pro Ala Gly Ser Pro Thr Ser Thr Glu Glu Gly
                        885                 890                 895
        Ser Pro Ala Gly Ser Pro Thr Ser Thr Glu Glu Gly Ala Ser Ser Pro
                        900                 905                 910
        Pro Val Leu Lys Arg His Gln Arg Glu Ile Thr Arg Thr Thr Leu Gln
                        915                 920                 925
        Ser Asp Gln Glu Glu Ile Asp Tyr Asp Asp Thr Ile Ser Val Glu Met
                        930                 935                 940
        Lys Lys Glu Asp Phe Asp Ile Tyr Asp Glu Asp Glu Asn Gln Ser Pro
        945                 950                 955                 960
        Arg Ser Phe Gln Lys Lys Thr Arg His Tyr Phe Ile Ala Ala Val Glu
                        965                 970                 975
        Arg Leu Trp Asp Tyr Gly Met Ser Ser Ser Pro His Val Leu Arg Asn
                        980                 985                 990
        Arg Ala Gln Ser Gly Ser Val Pro  Gln Phe Lys Lys Val  Val Phe Gln
                        995                 1000                1005
        Glu Phe  Thr Asp Gly Ser Phe  Thr Gln Pro Leu Tyr  Arg Gly Glu
        1010                 1015                 1020
        Leu Asn  Glu His Leu Gly Leu  Leu Gly Pro Tyr Ile  Arg Ala Glu
        1025                 1030                 1035
        Val Glu  Asp Asn Ile Met Val  Thr Phe Arg Asn Gln  Ala Ser Arg
        1040                 1045                 1050
        Pro Tyr  Ser Phe Tyr Ser Ser  Leu Ile Ser Tyr Glu  Glu Asp Gln
        1055                 1060                 1065
        Arg Gln  Gly Ala Glu Pro Arg  Lys Asn Phe Val Lys  Pro Asn Glu
        1070                 1075                 1080
        Thr Lys  Thr Tyr Phe Trp Lys  Val Gln His His Met  Ala Pro Thr
        1085                 1090                 1095
        Lys Asp  Glu Phe Asp Cys Lys  Ala Trp Ala Tyr Phe  Ser Asp Val
        1100                 1105                 1110
        Asp Leu  Glu Lys Asp Val His  Ser Gly Leu Ile Gly  Pro Leu Leu
        1115                 1120                 1125
        Val Cys  His Thr Asn Thr Leu  Asn Pro Ala His Gly  Arg Gln Val
        1130                 1135                 1140
        Thr Val  Gln Glu Phe Ala Leu  Phe Phe Thr Ile Phe  Asp Glu Thr
        1145                 1150                 1155
        Lys Ser  Trp Tyr Phe Thr Glu  Asn Met Glu Arg Asn  Cys Arg Ala
        1160                 1165                 1170
        Pro Cys  Asn Ile Gln Met Glu  Asp Pro Thr Phe Lys  Glu Asn Tyr
        1175                 1180                 1185
        Arg Phe  His Ala Ile Asn Gly  Tyr Ile Met Asp Thr  Leu Pro Gly
        1190                 1195                 1200
        Leu Val  Met Ala Gln Asp Gln  Arg Ile Arg Trp Tyr  Leu Leu Ser
        1205                 1210                 1215
        Met Gly  Ser Asn Glu Asn Ile  His Ser Ile His Phe  Ser Gly His
        1220                 1225                 1230
        Val Phe  Thr Val Arg Lys Lys  Glu Glu Tyr Lys Met  Ala Leu Tyr
        1235                 1240                 1245
        Asn Leu  Tyr Pro Gly Val Phe  Glu Thr Val Glu Met  Leu Pro Ser
        1250                 1255                 1260
        Lys Ala  Gly Ile Trp Arg Val  Glu Cys Leu Ile Gly  Glu His Leu
        1265                 1270                 1275
```

```
His Ala Gly Met Ser Thr Leu Phe Leu Val Tyr Ser Asn Lys Cys
    1280            1285                1290

Gln Thr Pro Leu Gly Met Ala Ser Gly His Ile Arg Asp Phe Gln
    1295            1300                1305

Ile Thr Ala Ser Gly Gln Tyr Gly Gln Trp Ala Pro Lys Leu Ala
    1310            1315                1320

Arg Leu His Tyr Ser Gly Ser Ile Asn Ala Trp Ser Thr Lys Glu
    1325            1330                1335

Pro Phe Ser Trp Ile Lys Val Asp Leu Leu Ala Pro Met Ile Ile
    1340            1345                1350

His Gly Ile Lys Thr Gln Gly Ala Arg Gln Lys Phe Ser Ser Leu
    1355            1360                1365

Tyr Ile Ser Gln Phe Ile Ile Met Tyr Ser Leu Asp Gly Lys Lys
    1370            1375                1380

Trp Gln Thr Tyr Arg Gly Asn Ser Thr Gly Thr Leu Met Val Phe
    1385            1390                1395

Phe Gly Asn Val Asp Ser Ser Gly Ile Lys His Asn Ile Phe Asn
    1400            1405                1410

Pro Pro Ile Ile Ala Arg Tyr Ile Arg Leu His Pro Thr His Tyr
    1415            1420                1425

Ser Ile Arg Ser Thr Leu Arg Met Glu Leu Met Gly Cys Asp Leu
    1430            1435                1440

Asn Ser Cys Ser Met Pro Leu Gly Met Glu Ser Lys Ala Ile Ser
    1445            1450                1455

Asp Ala Gln Ile Thr Ala Ser Ser Tyr Phe Thr Asn Met Phe Ala
    1460            1465                1470

Thr Trp Ser Pro Ser Lys Ala Arg Leu His Leu Gln Gly Arg Ser
    1475            1480                1485

Asn Ala Trp Arg Pro Gln Val Asn Asn Pro Lys Glu Trp Leu Gln
    1490            1495                1500

Val Asp Phe Gln Lys Thr Met Lys Val Thr Gly Val Thr Thr Gln
    1505            1510                1515

Gly Val Lys Ser Leu Leu Thr Ser Met Tyr Val Lys Glu Phe Leu
    1520            1525                1530

Ile Ser Ser Ser Gln Asp Gly His Gln Trp Thr Leu Phe Phe Gln
    1535            1540                1545

Asn Gly Lys Val Lys Val Phe Gln Gly Asn Gln Asp Ser Phe Thr
    1550            1555                1560

Pro Val Val Asn Ser Leu Asp Pro Pro Leu Leu Thr Arg Tyr Leu
    1565            1570                1575

Arg Ile His Pro Gln Ser Trp Val His Gln Ile Ala Leu Arg Met
    1580            1585                1590

Glu Val Leu Gly Cys Glu Ala Gln Asp Leu Tyr
    1595            1600

<210> SEQ ID NO 6
<211> LENGTH: 461
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6
```

-continued

| | | | | | | | | | | | | | | |
|---|---|---|---|---|---|---|---|---|---|---|---|---|---|---|
|Met|Gln|Arg|Val|Asn|Met|Ile|Met|Ala|Glu|Ser|Pro|Gly|Leu|Ile|Thr|
|1| | | |5| | | |10| | | |15| | |

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Leu
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly

```
                420              425              430
Glu Glu Cys Ala Met Lys Gly Lys Tyr Gly Ile Tyr Thr Lys Val Ser
            435              440              445

Arg Tyr Val Asn Trp Ile Lys Glu Lys Thr Lys Leu Thr
    450              455              460

<210> SEQ ID NO 7
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
tccataaagt aggaaacact aca                                           23
```

METHODS FOR THE PURIFICATION OF VIRAL VECTORS

RELATED APPLICATIONS

The instant application claims the benefit of priority to U.S. Provisional Application No. 63/043,697, filed Jun. 24, 2020 and U.S. Provisional Application No. 63/062,120, filed Aug. 6, 2020. The contents of the aforementioned provisional applications are incorporated by reference herein in their entireties.

BACKGROUND

Lentiviral vectors (LVs) and other viral vectors are an attractive tool for gene therapy (Thomas et al., 2003). LVs can transduce a broad range of tissues, including non-dividing cells such as hepatocytes, neurons and hematopoietic stem cells. Moreover, LVs can integrate into target cell genomes and provide long-term transgene expression.

In view of the ever-increasing need for viral vectors for gene therapy, improved methods of purification would be highly desired. Herein, we disclose improved methods for generating viral vector compositions that are suitable for systemic administration to subjects.

SUMMARY

The present disclosure relates to the purification of enveloped viral vectors for gene therapy applications. The present disclosure is based, at least in part, on the discovery that undesirable transgene protein contaminants can co-purify with a viral vector during conventional purification processes. In certain embodiments, the transgene protein contaminant is a by-product of transgene activity or secreted protein due to a promoter-mediated transcription product (e.g., a transgene protein contaminant that a viral vector encodes) generated during the bioproduction process. For example, packaging of a lentiviral vector requires the transfection of two or more plasmids into a host cell. In some embodiments, the plasmids include: (1) an envelope plasmid encoding an envelope protein (e.g., VSV-G); (2) a transfer plasmid encoding the transgene of interest; and (3) one or more packaging plasmids (e.g., a plasmid encoding gag and pol and a plasmid encoding rev, or a plasmid encoding gag, pol, and rev). In certain embodiments, the transgene protein contaminant is a promoter-mediated transcription product of a transfer plasmid. In certain embodiments, the promoter-mediated transcription product of the transfer plasmid is produced by the host cell (e.g., host packaging cell). In certain embodiments, the transgene protein contaminant is present in in the viral vector product sample, and may be present in detectable quantities.

The presence of a transgene protein contaminant in the viral vector drug product could result in one or more side effects when used for therapeutic treatment. This is particularly important in gene therapy approaches where the viral vector drug product is systemically administered. Systemic administration of viral vectors typically requires high viral vector doses to achieve efficient transduction of cells within a patient. In the case where a transgene protein contaminant is not sufficiently reduced and/or eliminated, the contaminating protein may be co-administered into a patient, and negatively impact the viral vector mediated production of the same protein within transduced cells of the body. Accordingly, the present invention provides methods to remove these transgene protein contaminants such that the viral vector drug substance is substantially free of the transgene protein contaminant.

In one aspect, the present invention provides a method of purifying a viral vector from a host cell, the method comprising: (i) contacting a composition comprising the viral vector and a transgene protein contaminant with a first chromatography matrix capable of selectively binding the transgene protein contaminant; and (ii) recovering the viral vector in the flow-through of the chromatography matrix, thereby separating the viral vector from the transgene protein contaminant.

In certain exemplary embodiments, the method further comprises (iii) contacting the composition comprising the viral vector and the transgene protein contaminant with a second chromatography matrix capable of selectively binding the viral vector, and (iv) eluting the viral vector from the second chromatography matrix, wherein steps (iii) and (iv) are performed prior to step (i).

In certain exemplary embodiments, the method further comprises (iii) contacting the viral vector recovered from step (ii) with a second chromatography matrix capable of selectively binding the viral vector, and (iv) eluting the viral vector from the second chromatography matrix.

In certain exemplary embodiments, steps (i) and (ii) are repeated multiple times.

In certain exemplary embodiments, step (i) is conducted in the presence of an agent that stabilizes the transgene protein contaminant. In certain exemplary embodiments, the agent is $CaCl_2$.

In certain exemplary embodiments, the method further comprises the step of (v) adjusting the concentration of a salt of the composition comprising the lentiviral vector and a FVIII transgene protein contaminant to a target salt concentration.

In certain exemplary embodiments, step (v) is performed prior to step (i).

In certain exemplary embodiments, if steps (iii) and (iv) are performed prior to step (i), then step (v) is performed between steps (iv) and (i).

In certain exemplary embodiments, the salt is NaCl.

In certain exemplary embodiments, the target salt concentration is from about 0.2M to about 0.6M. In certain exemplary embodiments, the target salt concentration is about 0.4M. In certain exemplary embodiments, the target salt concentration is from about 200 mM NaCl to about 600 mM NaCl.

In certain exemplary embodiments, step (i) is performed by loading the first chromatography matrix with the composition comprising the viral vector and the transgene protein contaminant in a loading buffer comprising Tris-HCl buffer at a pH about 7.0 to about 7.5. In certain embodiments, the loading buffer further comprises about 200 to about 600 mM NaCl and optionally about 2 mM $MgCl_2$.

In other exemplary embodiments, step (i) is performed by loading the first chromatography matrix with the composition comprising the viral vector and the transgene protein contaminant in a loading buffer comprising a phosphate buffer at a pH about 7.0 to about 7.5. In certain embodiments, the loading buffer further comprises about 200 to about 600 mM NaCl and optionally about 2 mM $MgCl_2$.

In certain exemplary embodiments, step (iv) is performed by eluting the viral vector from the second chromatography matrix with an elution buffer comprising Tris-HCl buffer at a pH about 7.0 to about 7.5. In certain embodiments, the elution buffer further comprises about 200 to about 600 mM NaCl and optionally about 2 mM $MgCl_2$.

In other exemplary embodiments, step (iv) is performed eluting the viral vector from the second chromatography matrix with an elution buffer comprising a phosphate buffer at a pH about 7.0 to about 7.5. In certain embodiments, the elution buffer further comprises about 200 to about 600 mM NaCl and optionally about 2 mM MgCl$_2$.

In certain exemplary embodiments, the method further comprises the step of (vi) combining the viral vector separated from the transgene protein contaminant with one or more pharmaceutical excipients to produce a pharmaceutical composition comprising the viral vector, wherein the pharmaceutical composition is substantially free of the transgene protein contaminant.

In certain exemplary embodiments, step (vi) is performed by ultrafiltration/diafiltration (UF/DF) of the viral vector separated from the transgene protein contaminant with a formulation buffer. In certain exemplary embodiments, the UF/DF step comprises tangential flow filtration (TFF).

In certain exemplary embodiments, the formulation buffer is a phosphate or histidine buffer comprising NaCl and Sucrose.

In certain exemplary embodiments, the pharmaceutical composition contains less than 20% of the transgene protein contaminant present in a reference viral vector composition purified with the second chromatography matrix but not the first chromatography matrix.

In certain exemplary embodiments, the viral vector is an enveloped viral vector. In certain exemplary embodiments, the enveloped viral vector is a lentiviral vector.

In certain exemplary embodiments, the viral vector encodes the transgene protein contaminant. In certain exemplary embodiments, the transgene protein contaminant is produced in the host cell by expression from a transfer plasmid.

In certain exemplary embodiments, the first chromatography matrix is selected from the group consisting of an affinity chromatography column, a cationic exchange (CEX) chromatography column, a multimodal chromatography (MMC) column and a hydrophobic interaction chromatography (HIC) column.

In certain exemplary embodiments, the first chromatography matrix is an affinity chromatography column comprising an affinity ligand that specifically binds to the transgene protein contaminant.

In certain exemplary embodiments, the second chromatography matrix is an anionic exchange (AEX) chromatography matrix. In certain exemplary embodiments, the second chromatography matrix is an anionic exchange (AEX) membrane.

In certain exemplary embodiments, the transgene protein is a clotting factor. In certain exemplary embodiments, the clotting factor is FVIII or FVIIIXTEN.

In certain exemplary embodiments, the first chromatography matrix is a VIIISelect affinity chromatography matrix.

In certain exemplary embodiments, the host cell is a mammalian cell or an insect cell. In certain exemplary embodiments, the mammalian cell is a CHO cell, a HEK293 cell, or a HeLa cell.

In certain exemplary embodiments, the composition comprising the viral vector and the transgene protein contaminant is a cell culture supernatant generated by culturing the host cell and separating and clarifying the cell culture supernatant from the host cell.

In certain exemplary embodiments, the cell culture supernatant is subjected to nuclease treatment.

In another aspect, the present invention provides a method of purifying a lentiviral vector (LVV) from a host cell, the lentiviral vector comprising a FVIII transgene, the method comprising: (i) contacting a composition comprising the lentiviral vector and a FVIII transgene protein contaminant with a first chromatography matrix capable of selectively binding FVIII transgene protein contaminant; and (ii) recovering the lentiviral vector in the flow-through of the chromatography matrix, thereby separating the lentiviral vector from the FVIII protein contaminant.

In certain exemplary embodiments, the method further comprises (iii) contacting the composition comprising the lentiviral vector and the FVIII transgene protein contaminant with a second chromatography matrix capable of selectively binding the lentiviral vector, and (iv) eluting the lentiviral vector from the second chromatography matrix, wherein steps (iii) and (iv) are performed prior to step (i), thereby separating the lentiviral vector from host cell contaminants.

In certain exemplary embodiments, the method further comprises (iii) contacting the lentiviral vector recovered from step (ii) with a second chromatography matrix capable of selectively binding the lentiviral vector, and (iv) eluting the lentiviral vector from the second chromatography matrix.

In certain exemplary embodiments, steps (i) and (ii) are repeated multiple times.

In certain exemplary embodiments, step (i) is conducted in the presence an agent that stabilizes the transgene protein contaminant. In certain exemplary embodiments, the agent is CaCl$_2$).

In certain exemplary embodiments, the method further comprises the step of (v) adjusting the concentration of a salt of the composition comprising the lentiviral vector and a FVIII transgene protein contaminant to a target salt concentration.

In certain exemplary embodiments, step (v) is performed prior to step (i).

In certain exemplary embodiments, if steps (iii) and (iv) are performed prior to step (i), then step (v) is performed between steps (iv) and (i).

In certain exemplary embodiments, the salt is NaCl.

In certain exemplary embodiments, the target salt concentration is from about 0.2M to about 0.6M. In certain exemplary embodiments, the target salt concentration is about 0.4M. In certain exemplary embodiments, the target salt concentration is from about 200 mM NaCl to about 600 mM NaCl.

In certain exemplary embodiments, step (i) is performed by loading the first chromatography matrix with the composition comprising the lentiviral vector and the FVIII transgene protein contaminant in a loading buffer comprising Tris-HCl buffer at a pH about 7.0 to about 7.5. In certain embodiments, the loading buffer further comprises about 200 to about 600 mM NaCl and optionally about 2 mM MgCl$_2$.

In other exemplary embodiments, step (i) is performed by loading the first chromatography matrix with the composition comprising the lentiviral vector and the FVIII transgene protein contaminant in a loading buffer comprising a phosphate buffer at a pH about 7.0 to about 7.5. In certain embodiments, the loading buffer further comprises about 200 to about 600 mM NaCl and optionally about 2 mM MgCl$_2$.

In certain exemplary embodiments, step (iv) is performed by eluting the lentiviral vector from the second chromatography matrix with an elution buffer comprising Tris-HCl buffer at a pH about 7.0 to about 7.5. In certain embodiments, the elution buffer further comprises about 200 to about 600 mM NaCl and optionally about 2 mM MgCl$_2$.

In other exemplary embodiments, step (iv) is performed eluting the lentiviral vector from the second chromatography matrix with an elution buffer comprising a phosphate buffer at a pH about 7.0 to about 7.5. In certain embodiments, the elution buffer further comprises about 200 to about 600 mM NaCl and optionally about 2 mM MgCl$_2$.

In certain exemplary embodiments, the method further comprises the step of (vi) combining the lentiviral vector separated from the transgene protein contaminant with one or more pharmaceutical excipients to make a pharmaceutical composition comprising the lentiviral vector, wherein the pharmaceutical composition is substantially free of the FVIII transgene protein contaminant.

In certain exemplary embodiments, step (vi) is performed by ultrafiltration/diafiltration (UF/DF) of the lentiviral vector separated from the transgene protein contaminant with a formulation buffer. In certain exemplary embodiments, the formulation buffer is a phosphate or histidine buffer comprising NaCl and Sucrose. In certain exemplary embodiments, the UF/DF step comprises tangential flow filtration (TFF).

In certain exemplary embodiments, the pharmaceutical composition contains less than 20% of the FVIII transgene protein contaminant present in a reference viral vector composition purified with the second chromatography matrix but not the first chromatography matrix.

In certain exemplary embodiments, the first chromatography matrix is selected from the group consisting of affinity chromatography column, cationic exchange (CEX) chromatography column, multimodal chromatography (MMC) column and hydrophobic interaction chromatography (HIC) column.

In certain exemplary embodiments, the first chromatography matrix is an affinity chromatography column comprising an affinity ligand that specifically binds to the recombinant FVIII protein. In certain exemplary embodiments, the affinity ligand is VIIISelect.

In certain exemplary embodiments, the FVIII transgene protein contaminant is a B-domain deleted FVIII protein. In certain exemplary embodiments, the FVIII transgene protein contaminant is a human FVIII protein comprising the amino acid sequence of SEQ ID NO:4. In certain exemplary embodiments, the FVIII transgene protein contaminant is a FVIIIXTEN molecule. In certain exemplary embodiments, the FVIIIXTEN molecule comprises the amino acid sequence of SEQ ID NO:5.

In certain exemplary embodiments, the second chromatography matrix is an anionic exchange (AEX) chromatography matrix. In certain exemplary embodiments, the second chromatography matrix is an anionic exchange (AEX) membrane.

In certain exemplary embodiments, the host cell is a mammalian cell or an insect cell. In certain exemplary embodiments, the mammalian cell is a CHO cell, a HEK293 cell, or a HeLa cell.

In certain exemplary embodiments, the composition comprising the viral vector and the FVIII transgene protein contaminant is a cell culture supernatant generated by culturing the host cell and separating and clarifying the cell culture supernatant from the host cell. \

In certain exemplary embodiments, the cell culture supernatant is subjected to nuclease treatment.

In another aspect, the present invention provides a composition comprising a viral vector produced according to a method described herein.

In certain exemplary embodiments, the composition is a pharmaceutical composition comprising the viral vector and one or more pharmaceutical excipients, and wherein the composition is substantially free of transgene protein contaminant.

In certain exemplary embodiments, the transgene protein is a clotting factor. In certain exemplary embodiments, the clotting factor is FVIII, FVIIIXTEN, or FIX. In certain exemplary embodiments, the clotting factor is a B-domain deleted FVIII protein. In certain exemplary embodiments, the clotting factor is a human FVIII protein comprising the amino acid sequence of SEQ ID NO:4. In certain exemplary embodiments, the clotting factor is a FVIII-XTEN molecule. In certain exemplary embodiments, the FVIII-XTEN molecule comprises the amino acid sequence of SEQ ID NO:5.

In certain exemplary embodiments, the composition contains less than 20% of the transgene protein present in a reference viral vector composition purified with the second chromatography matrix but not the first chromatography matrix. In certain exemplary embodiments, the composition has a total FVIII activity level of less than 10% of the reference viral vector composition purified with the second chromatography matrix but not the first chromatography matrix. In one exemplary embodiment, the composition has a total FVIII activity level of about 1 IU or less.

BRIEF DESCRIPTION OF THE DRAWINGS

FIG. 1A shows the conventional downstream work flow, involving a single vector capture purification chromatography step that is primarily responsible for purifying viral vector from process- and product-related impurities. FIG. 1B shows an improved downstream work flow according to one embodiment of the present disclosure, involving at least two purification chromatography steps, one of which is a transgene protein capture step of the invention.

FIG. 3A is a plot showing the level of transgene protein activity remaining in product following purification by a conventional One Column Process (e.g., as shown in FIG. 1A) or a Two Column Process of the invention that includes VIIISelect as the additional transgene protein capture step (e.g., as shown in FIG. 1B). FIG. 3B is a plot showing percent reduction of transgene protein activation for the Two Column Process as compared to the One Column Process.

FIG. 6A shows an improved downstream work flow according to one embodiment of the present disclosure, wherein the load sample for the second chromatography purification step is adjusted. FIG. 6B shows an improved downstream work flow according to one embodiment of the present disclosure, wherein the load sample for the first chromatography purification step is adjusted, and the load sample for the second chromatography purification step is adjusted.

FIG. 7A is a plot showing the level of FVIIIXTEN activity detected as a function of total functional vector recovery before (black bars) and after (grey bars) applying a sample to an VIIISelect affinity chromatography resin, wherein the load sample comprises 400 mM NaCl (Exp5) or 100 mM NaCl (Exp6). FIG. 7B is a plot showing the level of FVIIIXTEN activity detected as a function of total P24 capsid recovery before (black bars) and after (grey bars) applying a sample to an VIIISelect affinity chromatography resin, wherein the load sample comprises 400 mM NaCl (Exp5) or 100 mM NaCl (Exp6).

DETAILED DESCRIPTION

Figure 1A:
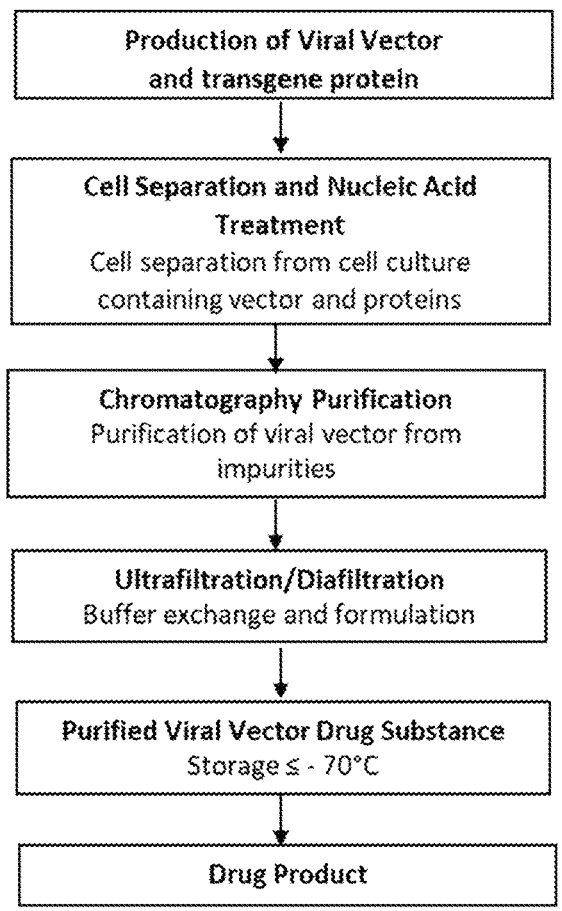
FIGS. 1A-1B show schematics of a conventional process work flow to manufacture an enveloped viral vector drug substance for gene therapy applications.

The present disclosure is based on the finding that during bioproduction of viral vector, the final viral vector product could contain a transgene protein contaminant. For example, during manufacturing of lentiviral vector (LV-FVIII or LV-FVIIIXTEN) product using HEK293T cells, it was unexpectedly found that upstream CMV promoter activity in the transgene encoding plasmid (e.g., transfer plasmid) could mediate transgene mRNA production that would result in the production of contaminating FVIII or FVIIIXTEN protein. During purification, such FVIII or FVIIIXTEN transgene protein contaminant could be inadvertently co-purified with lentiviral vector via non-specific association with vector particles and end up being inadvertently co-administered to a patient. Administering a viral vector product that contains a transgene protein contaminant could interfere with the efficiency of the viral vector to transduce target cells (e.g., target cells within a patient), and/or with viral vector mediated expression of the same transgene protein. Furthermore, the existence of contaminating transgene protein (e.g., FVIII or FVIIIXTEN) in the lentiviral vector drug product (LV-FVIII or LV-FVIIIXTEN) could potentially elicit unwanted immune responses that result in the generation of antibodies against the transgene protein contaminant (e.g., anti-drug antibodies (ADAs)) and/or potential cytotoxic T-cell responses against LV-transduced cells.

Therefore, to circumvent the issue of the presence of a transgene protein contaminant in a viral vector product, the instant disclosure provides methods for the purification of a viral vector from a host cell, comprising the reduction and/or elimination of a transgene protein contaminant that the viral vector encodes. In certain embodiments, purification of a viral vector utilizing the methods provided herein results in a viral vector product that is substantially free of a transgene protein contaminant.

Generally, nomenclature used in connection with cell and tissue culture, molecular biology, biophysics, immunology, microbiology, genetics, and protein and nucleic acid chemistry described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein is well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedence over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

As used herein, the term "about," when used in reference to a particular recited numerical value, means approximately, roughly, around, or in the regions of. When the term "about" is used in conjunction with a numerical range, it modifies that range by extending the upper and lower boundaries of the numerical values set forth. In general, the term "about" is used herein to modify a numerical value above and below the stated value by a variance of 10 percent, higher or lower than the stated value. For example, as used herein, the expression "about 100" includes 90 and 110 and all values in between (e.g., 91, 92, 93, 94, etc.). In certain embodiments, the term "about" means that the value may vary from the recited value by no more than 1%. For example, as used herein, the expression "about 100" includes 99 and 101 and all values in between (e.g., 99.1, 99.2, 99.3, 99.4, etc.).

As used herein, the term "vector" refers to any vehicle for the cloning of and/or transfer of a nucleic acid into a host cell. A vector can be a replicon to which another nucleic acid segment can be attached so as to bring about the replication of the attached segment. The term "vector" includes both viral and non-viral vehicles for introducing the nucleic acid into a cell in vitro, ex vivo or in vivo. A large number of vectors are known and used in the art including, for example, plasmids, modified eukaryotic viruses, or modified bacterial viruses. Insertion of a polynucleotide into a suitable vector can be accomplished by ligating the appropriate polynucleotide fragments into a chosen vector that has complementary cohesive termini.

As used herein, the term "viral vector" refers to any viral vehicle for introducing a nucleic acid into a cell. A viral vector may be utilized for introducing a nucleic acid into any cell in any way, for example, in vitro, ex vivo, or in vivo. As known to those of skill in the art, a viral vector is packaged (produced) by a packaging cell (e.g., a packaging cell line). In some embodiments, one or more plasmids are introduced into a packaging cell in order to produce the viral vector. In some embodiments, three or more plasmids are introduced into a packaging cell in order to produce the viral vector. In the production of a lentiviral vector, typically, (1) a transfer plasmid comprising a transgene of interest; (2) an envelope plasmid comprising an envelope protein coding sequence (e.g., VSV-G); and (3) one or more packaging plasmids are co-transfected into a packaging cell. The lentiviral packaging plasmids comprise at least the gag, pol, and rev genes, on a single plasmid (e.g., in the case of second generation lentiviral vector production), or on separate plasmids (i.e., one packaging plasmid comprising the gag and pol genes, and another packaging plasmids comprising the rev gene; e.g., in the case of third generation lentiviral vector production). In the production of adeno-associated viral (AAV) vector, typically, (1) a transfer plasmid comprising a transgene of interest; (2) a rep/cap plasmid comprising the rep and cap genes required for the AAV life cycle; and (3) a helper plasmid comprising genes that mediate AAV replication are co-transfected into a packaging cell. Variations on the production of viral vector are known to those of skill in the art. For example, one of skill in the art will appreciate that one or more of the vectors can be combined into a single vector.

As used herein, the phrase "recombinant lentiviral vector" refers to a vector with sufficient lentiviral genetic information to allow packaging of an RNA genome (e.g., a heterologous RNA genome), in the presence of packaging components, into a viral particle capable of infecting a target cell. Infection of the target cell may include reverse transcription and integration into the target cell genome. The recombinant lentiviral vector carries non-viral coding sequences which are to be delivered by the vector to the target cell. A recombinant lentiviral vector is incapable of independent replication to produce infectious lentiviral particles within the final target cell. Usually the recombinant lentiviral vector lacks a functional gag-pol and/or env gene and/or other genes essential for replication.

As used herein the terms "heterologous" or "exogenous" refer to such molecules that are not normally found in a given context, e.g., in a cell or in a polypeptide. For example, an exogenous or heterologous molecule can be introduced into a cell and are only present after manipulation of the cell, e.g., by transfection or other forms of genetic engineering or a heterologous amino acid sequence can be present in a protein in which it is not naturally found. Accordingly, a recombinant lentiviral vector comprising a heterologous RNA genome refers to an RNA genome that is not naturally found in a lentivirus.

As used herein, the term "transgene protein contaminant" refers to a transgene protein that is produced in a host cell during production of the viral vector in the host cell ex vivo. In certain embodiments, the transgene protein is encoded by a transgene of the viral vector but is unintentionally expressed in the host cell during the viral vector production. In certain embodiments, the transgene protein product may be a by-product of undesired transgene activity in the host cell. In other embodiments, the transgene protein may be secreted by the host cell due to promoter-mediated transcription. In exemplary embodiments, the transgene protein contaminant may be produced in the host cell by spurious expression from a transfer plasmid containing the transgene of interest.

As used herein, the term "capable of selectively binding" refers to having the ability to bind (e.g., reversibly bind) a certain molecule over other molecules (e.g., preferentially binds a particular molecule; has a greater affinity for; binds a particular molecule to a greater degree than, or to the exclusion of, other molecules). For example, when a composition comprising a viral vector is contacted with a chromatography matrix capable of selectively binding the viral vector, the chromatography matrix will bind (e.g., retain) the viral vector over other molecules that may be present in the composition (e.g., the chromatography matrix substantially binds more of the viral vector compared to other molecules present in the composition). As such, when a chromatography matrix selectively binds a viral vector, the viral vector is retained by the chromatography matrix.

As used herein, the term "treat" refers to an amelioration or reduction of one or more symptoms of a disorder. Treating can, but need not, be a cure.

As used herein, the phrase "systemically administer" refers to prescribing or giving a pharmaceutical composition comprising a drug product to a subject, such that the drug product is introduced into the circulatory system (e.g., bloodstream) of the subject. In certain embodiments, systemic administration refers to prescribing or giving a pharmaceutical composition comprising a viral vector (e.g., a lentiviral vector) to a subject, such that the viral vector is introduced into the circulatory system (e.g., bloodstream) of the subject. Examples of routes of systemic administration include, but are not limited to, intravenous, e.g., intravenous injection and intravenous infusion, e.g., via central venous access, oral administration, intramuscular administration, intradermal administration, and subcutaneous administration.

A. Purification of Viral Vectors

The present disclosure is based on the introduction of a purification step (herein the "transgene protein capture step") to a viral vector production process in order to reduce and/or eliminate a transgene protein contaminant. Introduction of the transgene protein capture step allows for the reduction and/or elimination of a transgene protein contaminant from a composition comprising a viral vector, and without limitation, could provide the following clinical benefits: (1) improve potency of viral vector drug product used to transduce cells within patient body; (2) potentially improve efficacy of gene therapy product administered systemically; (3) improve the safety profile of in vivo gene therapy products as a result of minimizing potential immune responses against protein antigens immediately after administration (e.g., minimize the potential development of anti-drug antibodies); (4) minimize any negative therapeutic effect or side effects due to presence of transgene protein product; and (5) improve product quality and increase product purity. In certain embodiments, the transgene protein contaminant is produced in the host cell by expression from a transfer plasmid.

In certain aspects, the transgene protein capture step comprises: (i) contacting a composition comprising the viral vector and a transgene protein contaminant with a first chromatography matrix capable of selectively binding the transgene protein contaminant; and (ii) recovering the viral vector in the flow-through of the chromatography matrix, thereby separating the viral vector from the transgene protein contaminant. As will be appreciated by one of skill in the art, the transgene capture step can be performed once or multiple times (two or more times, three or more times, etc.) using the same or different transgene capture steps. The resultant viral vector may then be utilized for introducing a nucleic acid into any cell in any way, for example, in vitro, ex vivo, or in vivo. In certain embodiments, a viral vector of the present disclosure is a lentiviral vector.

As known in the art, the safety profile of a drug product can depend on the development of any unwanted immunogenicity against the drug product (e.g., development of an anti-drug antibody against the drug product). The development of unwanted immunogenicity is affected by the route of administration (e.g., intradermal, subcutaneous, inhalation, intramuscular, intravenous routes, and the like), dose, and frequency of administration of the drug product. Methods of viral vector purification incorporating one or more transgene capture steps described herein reduces and/or eliminates a transgene protein contaminant that may be present in an administrable viral vector drug product, and as such, reduces and/or eliminates the development of unwanted immunogenicity against the transgene protein contaminant. Those of skill in the art will appreciate that the reduction and/or elimination of the development of unwanted immunogenicity can occur however the drug product (e.g., viral vector drug product) is administered, at any dosage, and at any dosing frequency.

In certain embodiments, the transgene protein capture step (e.g., the transgene impurity capture step) employs the use of one or more chromatography separation techniques. In certain embodiments, transgene protein capture step employs the use of one or more chromatography matrices. In some embodiments, the one or more chromatography matrices are selected from the group consisting of affinity chromatography, cation exchange (CEX) chromatography, anion exchange (AEX) chromatography, multimodal chromatography (MMC) and hydrophobic interaction chromatography (HIC).

In various embodiments described herein, various buffers and solutions that are known to those of skill in the art are used. Any suitable buffers and solutions known to those of skill in the art can be used. For example, a purification step may require the use of several buffers and solutions, e.g., sanitization solutions, equilibration buffers, wash buffers, elution buffers, stripping buffers, regeneration buffers, diluent buffers, and the like.

In certain embodiments, transgene protein capture step employs affinity chromatography. The term "affinity chromatography" refers to a protein separation technique in which a protein is reversibly and specifically bound to an affinity ligand (e.g., an affinity ligand that specifically binds to a transgene protein contaminant). As used herein, the term "specifically binds" refers to the ability to mediate a binding reaction with a molecule which is highly preferential to the molecule.

Affinity chromatography utilizes specific binding interactions between molecules to separate components. In affinity chromatography, an affinity ligand is immobilized to a solid support, e.g., resin, such that when a composition is passed through the solid support, molecules having specific binding affinity for the affinity ligand become retained by the resin. In certain embodiments, transgene protein capture step utilizes an affinity chromatography column comprising an affinity ligand that specifically binds to the transgene protein contaminant. In some embodiments, affinity ligands are immobilized or coupled directly to solid support material by formation of covalent chemical bonds between particular functional groups on the affinity ligand (e.g., primary amines, sulfhydryls, carboxylic acids, aldehydes) and reactive groups on the support. In some embodiments, affinity ligands are immobilized by indirect coupling approaches, e.g., via a glutathione S-transferase (GST)-tagged fusion protein captured to a glutathione support via the glutathione-GST affinity interaction. Affinity ligands that bind to general classes of proteins (e.g., antibodies) or commonly used fusion protein tags (e.g., Histidine tag, or His-tag) are readily available in pre-immobilized forms for use in affinity purification. In certain embodiments, more specialized affinity ligands such as specific antibodies or antigens of interest can be immobilized. For example, a peptide antigen can be immobilized to a support and used to purify antibodies that recognize the peptide. Accordingly, in certain embodiments, the present disclosure provides a method of purifying a viral vector from a host cell, comprising: subjecting a composition comprising the viral vector and a transgene protein contaminant to affinity chromatography purification capable of selectively binding the transgene protein contaminant; and recovering the viral vector in the resultant flow-through of the affinity chromatography purification, thereby separating the viral vector from the transgene protein contaminant. In certain embodiments, the method of purifying a viral vector from a host cell comprises: (i) contacting a composition comprising the viral vector and a transgene protein contaminant with an affinity chromatography matrix capable of selectively binding the transgene protein contaminant; and (ii) recovering the viral vector in the flow-through of the affinity chromatography matrix, thereby separating the viral vector from the transgene protein contaminant.

For the purposes of reducing and/or eliminating the presence of a specific transgene protein contaminant (e.g., an FVIII protein) in a viral vector product, in certain embodiments, the affinity ligand, is covalently attached to a chromatographic solid phase material and is accessible to the contaminating protein (e.g., an FVIII protein) in solution as the solution contacts the chromatographic solid phase material. The transgene protein contaminant (e.g., FVIII protein) is retained via its specific binding affinity for the affinity ligand during the chromatographic steps, while other solutes and/or proteins in the mixture (e.g., viral vector) do not bind appreciably or specifically to the ligand. Binding of the transgene protein contaminant to the immobilized ligand allows the desired viral vector to be passed through the chromatographic medium while the contaminating protein remains specifically bound to the immobilized ligand on the solid phase material. Any component can be used as a ligand for the purposes of reducing and/or eliminating its respective specific binding partner. In certain embodiments, the affinity ligand is an antibody, antibody fragment, antibody variant, peptidomimetic or peptide having specific binding affinity for the transgene, e.g. an antibody, antibody fragment, antibody variant, peptidomimetic or peptide having binding affinity for FVIII. In an exemplary embodiment, a ligand for the FVIII protein is VIIISelect™ from GE Healthcare/Cytiva.

In certain embodiments, affinity purification employs various buffers and solutions. Any buffers and solutions known to those of skill in the art can be used. For example, a suitable sanitization buffer can comprise 0.5 M NaOH; a suitable equilibration buffer can comprise 20 mM Tris or 20 mM phosphate, 0 to 2 mM $MgCl_2$, 10-30 mM $CaCl_2$), 10 to 70 mM NaCl, and have a pH of 7.2; a suitable stripping or cleaning buffer can comprise 0.5 M NaOH, a solution containing phosphoric acid, Benzyle alcohol, or acetic acid; and a suitable regenerating buffer can comprise 20 mM Tris, 2 mM $MgCl_2$, 150 mM NaCl, and have a pH of 7.2.

In some embodiments, the transgene protein capture step comprises subjecting a composition comprising a viral vector and a transgene protein contaminant to ion exchange chromatography purification capable of retaining the transgene protein contaminant within the chromatographic substrate (e.g., matrix, resin, column). As used herein, the term "ion exchange chromatography" refers to the separation of ionizable molecules based on their total surface charge. In certain embodiment, embodiments, the ion exchange chromatography employs a cation exchange resin. The terms "cation exchange resin," "cation exchange adsorbent," or "cation exchange matrix" refer to a solid phase which is negatively charged, and which thus has free cations for exchange with cations in an aqueous solution passed over or through the solid phase. A negatively charged ligand attached to the solid phase to form the cation exchange resin can, e.g., be a carboxylate or sulfonate. Commercially available cation exchange resins include carboxy-methylcellulose, sulphopropyl (SP) immobilized on agarose (e.g., SP SEPHAROSE-XL, SP-SEPHAROSE-Fast Flow, SP SEPHAROSE-High Performance, CM SEPHAROSE-Fast Flow, CM SEPHAROSE.High Performance, CAPTO-S, and CAPTO-SP ImpRes from GE Healthcare Life Sciences, or FRACTOGEL EMD SE HiCap, FRACTOGEL EMD SO3-, FRACTOGEL EMD COO—, ESHMUNO S, and ESHMUNO. CPX from EMD Millipore, or UNOSPHERE-S and NUVIA-S from Bio-Rad).

In some embodiments, the transgene protein capture step comprises subjecting a composition comprising a viral vector and a transgene protein contaminant to hydrophobic interaction chromatography (HIC) purification capable of retaining the transgene protein contaminant within the chromatographic substrate (e.g., matrix, resin, column). The term "hydrophobic interaction chromatography (HIC)," as used herein, refers to the separation of components based on hydrophobic interactions with a stationary phase (e.g., resin). The elution order in HIC enables components to be ranked on the basis of their relative hydrophobicity. Advantages of HIC include, e.g., the use of non-denaturing conditions, it does not require the use of organic solvents or high temperatures, and separations are carried out at physiological pH, which preserves virus structure when used in virus purification processes. In some embodiments, the transgene protein capture step utilizes hydrophobic interaction chromatography. Hydrophobic interaction chromatography (HIC) is a technique for separating biomolecules based on differences in their surface hydrophobicity. HIC chromatographic media contain hydrophobic ligands such as linear chain hydrocarbons (e.g., propyl (C3), butyl (C4), hexyl (C6), or octyl (C8)) or aromatics (e.g., phenyl). In pure water, the hydrophobic effect is too weak for functional interaction between the ligand and proteins, or between the proteins themselves. However, lyotropic salts enhance hydrophobic interactions, and the addition of salt drives the capture of proteins to HIC media. For this reason, HIC resins are usually loaded under high salt concentrations and eluted at lower salt concentrations. As one of ordinary skill in the art will appreciate, ammonium sulfate $[(NH_4)_2SO_4]$ is the most commonly used salt to control capture of proteins via HIC chromatography, because of the high lyotropic ranking of both ammonium and sulfate ions in the Hofmeister series, and the high solubility of the salt. As one of ordinary skill in the art can appreciate, the concentration of salt (e.g., ammonium sulfate) can be manipulated to achieve the optimal concentration for transgene protein contaminant binding. In addition, co-solvents can also affect the hydrophobic interaction. For example, ethylene or propylene glycol can reduce the interaction between protein and the immobilized ligand and thus be useful for improving elution profiles. Examples of suitable hydrophobic resins include without limitation, Capto Adhere, Tosoh Butyl 650M, Tosoh SuperButyl 650C, Tosoh Phenyl 650C, and EMD Fractogel® Phenyl (Tosoh Bioscience LLC, PA).

In some embodiments, the transgene protein capture step comprises subjecting a composition comprising a viral vector and a transgene protein contaminant to multimodal chromatography purification capable of retaining the transgene protein contaminant within the chromatographic substrate (e.g., matrix, resin, column) (e.g., matrix, resin, column). As used herein, the term "mixed mode chromatography" or "multi-modal chromatography," refers to a chromatography that employs a combination of two or more mechanisms in order to achieve separation of components in a mixture. In some embodiments, the transgene protein capture step utilizes multi-modal or mixed mode chromatography (MMC) to separate product-related impurities (e.g., a transgene protein contaminant) from viral vector. In some embodiments, MMC operates on the basis of at least size differences between the virus and the impurities, and/or chemical interaction occurring between the impurities and one or more chromatography ligands. Various types of MMC are known to those of skill in the art, including physical and chemical MMC. Chemical MMC includes combinations between principles of, without limitation, ion exchange chromatography, hydrophobic interaction chromatography, size exclusion chromatography, reverse phase liquid chromatography, and hydrophilic interaction liquid chromatography. Further examples include, without limitation, resins that exploit combinations of hydrogen bonding, pi-pi bonding, and metal affinity. An example of multimodal chromatography employs the use of Capto® Core 700 chromatography resin (GE Healthcare Bio-Sciences) which comprises octylamine ligands designed to have both hydrophobic and positively charged properties that trap molecules under a certain size, e.g., 700 kilodaltons (kDA). In such chromatography resins, the bead exteriors are inactive, and permits the purification of viral vector by size exclusion, where the desired viral vector passes through the resin and impurities are retained therein.

The steps involved in viral vector purification may be conducted in the presence of certain agents known to those of skill in the art that improve efficiency. For example, in certain embodiments, the transgene protein capture step is conducted in the presence of an agent that stabilizes the transgene protein contaminant. In certain embodiments, the transgene protein capture step is conducted in the presence of an agent that stabilizes the transgene protein contaminant, wherein the agent is $CaCl_2$).

The transgene protein capture step as described herein may be incorporated into a viral vector production process known to one of skill in the art. FIG. 1A is a generic flow diagram depicting a typical viral vector manufacturing process comprising the upstream steps (thawing of a cell bank vial; cell growth and passaging; transfection and/or induction of host cells to produce viral vector) followed by a series of downstream steps (harvesting of viral vector comprising cell removal (clarification) and nuclease treatment; at least one purification step to separate the vector from other product- and process-related impurities (herein the "viral vector capture step"); and an ultrafiltration/diafiltration step for final formulation of drug substance). In general, the transgene capture step can be incorporated into a viral vector production process at any point between the clarification step and the final step in the downstream process.

Upstream processing steps for viral vector production generally comprises the steps of cell expansion, transfection or infection of vector producing cells, and viral vector production. Generally, transfection or infection of vector producing cells is achieved by transient transfection, or the use of stable producer cell lines in mammalian or insect cells. Cells are transfected with viral vector encoding components and are cultured to increase virus numbers and/or virus titers. Methods of transfection and culturing cells are known to those of skill in the art, and includes at least, providing necessary nutrients to the cell, e.g., a suitable culture media. Methods for culturing cells include, e.g., growth adhering to surfaces, growth in suspension, or combinations thereof. Culturing can be performed in suitable containers, for example, culture dishes, culture flasks, or roller bottles. Large scale culturing is often performed with the use of bioreactors using a variety of systems available to those of skill in the art, including, e.g., batch, fed-batch, continuous systems, hollow fiber, etc.

Following upstream processing steps, downstream processing steps are typically as outlined in FIG. 1A, including the downstream processing steps of clarification, nuclease treatment, viral vector capture, and sterile filtration. The goal of downstream processing is to separate the viral vector from the various impurities produced during upstream processing and to get the vector into the appropriate state for formulation and administration to patients. The skilled artisan would be able to determine the optimal order of the aforementioned steps in order to obtain the most efficient process for viral vector manufacturing (e.g., the optimal order of steps in the process to yield the most viral vector).

The clarification step includes the elimination of large debris and macromolecular complexes from the initial crude suspension. In certain embodiments, clarification includes cell lysis in order to improve viral vector yield. A variety of methods are known to those of skill in the art seeking to lyse cells, including physical methods such as with the use of microfluidizers or heat-shock treatments to promote lysis. Lysis is often achieved using detergents. Detergents are available in nonionic form, e.g., Triton X-100, Triton X-114, Tween 20, Tween 80, NP-40, octyl glucoside, and octyl thioglucoside, in anionic form, e.g., SDS, and in zwitterionic form, e.g., CHAPS and CHAPSO. In some embodiments, clarification is performed by a filtration step to remove cellular debris and other impurities. Suitable filters include, without limitation, filters comprising cellulose filters, e.g., cellulose fibers combined with inorganic filter aids (e.g., fumed silica, perlite, diatomaceous earth), cellulose fibers combined with organic resins, or any combination thereof, and polymeric filters such as those comprising nylon, polyethersulfone, or polypropylene. Any clarification approach known to those of skill in the art would be suitable for a viral vector production process of the present invention. Suitable clarification approaches include, without limitation, centrifugation, microfiltration, dead-end filtration, depth filtration, membrane filtration, or a combination thereof. Accordingly, clarification may include the use of a combination of filters with decreasing pore size, e.g., down to 0.2 um.

Culturing a host cell (e.g., a viral vector producing cell) followed by subsequent lysis and clarification steps results in a composition comprising a viral vector and a transgene protein contaminant. In certain embodiments, the composition comprising the viral vector and a transgene protein contaminant is a cell culture supernatant generated by culturing the host cell and separating and clarifying the cell culture supernatant from the host cell. The host cell may be any host cell suitable for viral vector production known to those of skill in the art. In certain embodiments, the host cell is selected from the group consisting of a CHO cell, a HEK293 cell (e.g., a HEK293T cell), a HeLa cell, and an insect cell. In certain embodiments, the host cell is a HEK293 cell. In certain embodiments, the host cell is a HEK293T cell.

During and/or after the cell lysis step, a nuclease treatment step may be performed in order to degrade nucleic acids (e.g., host cell nucleic acids, RNA and/or DNA contaminants) and break up any macromolecular complexes. The nuclease treatment step may be performed during and/or after clarification. Suitable nucleases for use in a viral vector production process of the present invention include, without limitation, Benzonase, Denarase, and any other DNase and/or RNase known to those of skill in the art. In some embodiments, instead of, or in addition to nuclease treatment, selective precipitation of nucleic acid impurities may be performed, e.g. by precipitation with a suitable precipitation agent such as, without limitation, polyethylene imine (PEI), tetradecyltrimethyl-ammonium chloride (TTA), domiphen bromide (DB), cetylpyridinium chloride (CPC), benzethonium chloride (BTC), and cetyl trimethylammonium bromide (CTAB).

In certain embodiments, cell separation and nuclease treatment is carried out using a phosphate or Tris buffer having a pH of about 7.

After cell removal and nuclease treatment, one or more viral vector capture steps may be employed to purify the viral vector from various host cell contaminants. Whereas the transgene protein capture step of the invention comprises subjecting a composition comprising a viral vector and a transgene protein contaminant to chromatographic purification capable of selectively binding the transgene protein contaminant within the chromatographic substrate, the viral vector capture step employs a chromatographic substrate capable of selectively binding the viral vector within the chromatographic substrate (e.g., matrix, resin, column). In certain embodiments, the viral vector capture step comprises (i) contacting a composition comprising the viral vector (and one or most host cell contaminants) with a chromatography matrix capable of selectively binding the viral vector, and (ii) eluting the viral vector from the chromatography matrix, thereby separating the viral vector from host cell contaminants.

One or more of a variety of chromatographic purification techniques can be used for viral vector capture. In some embodiments, the viral vector capture step chromatography is selected from the group consisting of anion exchange chromatography, size exclusion chromatography, hydrophobic interaction chromatography (HIC), reverse-phase chromatography (RPC), and immobilized metal ion affinity chromatography (IMAC). In certain embodiments, the ion exchange chromatography employs an anionic exchange resin. The terms "anion exchange resin," "anion exchange adsorbent," or "anion exchange matrix" are used herein to refer to a solid phase which is positively charged, e.g., having one or more positively charged ligands, such as quaternary amino groups, attached thereto. Anion exchange chromatography resins have affinity for molecules having net negative surface charges and are useful in separating negatively charged molecules from a composition. Commercially available anion exchange resins include DEAE SEPHAROSE™ Fast Flow, Q SEPHAROSE™ Fast Flow, Q SEPHAROSE™ High Performance, Q SEPHAROSE™ XL, CAPTO™ DEAE, CAPTO™ Q, and CAPTO™ Q ImpRes from GE Healthcare Life Sciences, or FRACTOGEL™ EMD TMAE HiCap, FRACTOGEL™ EMD DEAE, and ESHMUNO™ Q from EMD Millipore, or UNOSPHERE™ Q and NUVIA™ Q from Bio-Rad.

In certain embodiments, the ion exchange chromatography comprises the use of membrane exchange. Membrane exchange chromatography is a type of ion exchange chromatography using a membrane absorber, for which there are various types including flat sheet, hollow fibre, and radial flow. In some embodiments, a membrane exchange column is packed with microporous membranes comprising internal pores which contain adsorptive moieties that can bind the viral vectors. Adsorptive membranes are available in a variety of shapes and chemistries which allows them to be suitable for purification purposes.

Various buffers and solutions known to those of skill in the art may be used for viral vector capture. For example, a suitable sanitization solution can comprise 0.5 M NaOH; a suitable equilibration buffer can comprise 20 mM Tris, 2 mM $MgCl_2$, 150 mM NaCl, and have a pH of 7.2; a suitable wash buffer can comprise 20 mM Tris, 2 mM $MgCl_2$, 400 mM NaCl, and have a pH of 7.2; a suitable elution buffer can comprise 20 mM Tris, 2 mM $MgCl_2$, 1200 mM NaCl, and have a pH of 7.2; a suitable stripping buffer can comprise 20 mM Tris, 2 mM $MgCl_2$, 2000 mM NaCl, and have a pH of 7.2; and a suitable regeneration buffer can comprise 20 mM Tris, 2 mM $MgCl_2$, 150 mM NaCl, and have a pH of 7.2.

Figure 1B:
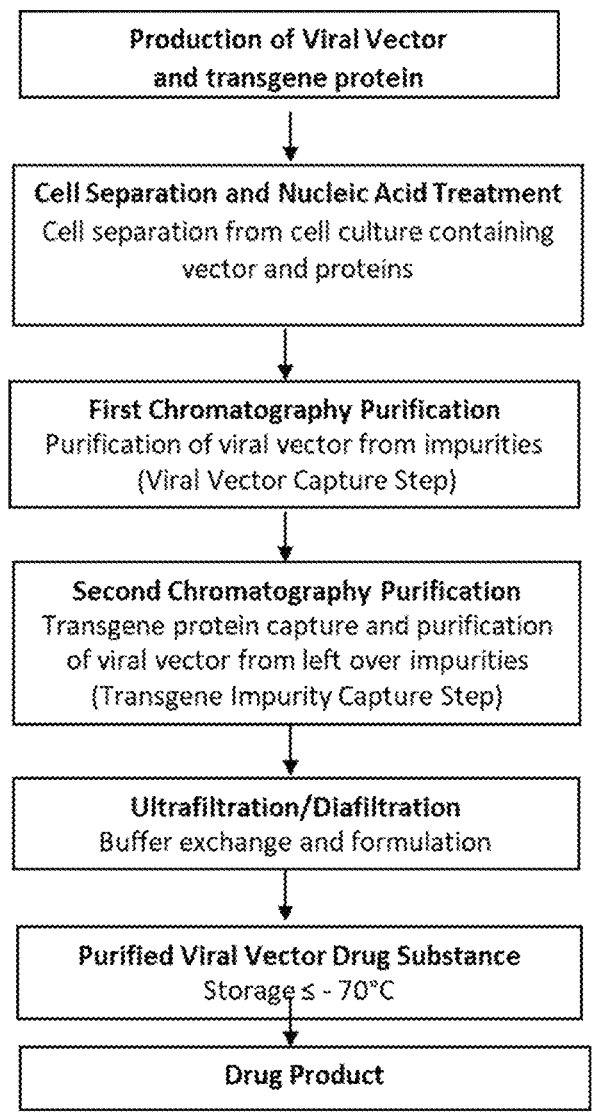

In certain embodiments, as shown in FIG. 1B, the viral vector capture step can be performed before the transgene protein purification step. For example, in certain aspects, the present disclosure provides a method of purifying a viral vector from a host cell, comprising: (i) contacting a composition comprising the viral vector and a transgene protein contaminant with a first chromatography matrix capable of selectively binding the transgene protein contaminant; (ii) recovering the viral vector in the flow-through of the chromatography matrix, thereby separating the viral vector from the transgene protein contaminant; (iii) contacting the viral vector recovered from step (ii) with a second chromatography matrix capable of selectively binding the viral vector, and (iv) eluting the viral vector from the second chromatography matrix, thereby separating the viral vector from host cell contaminants.

In other embodiments, the viral vector capture step can be performed after the transgene protein capture step. Accordingly, in certain embodiments, the present disclosure provides a method of purifying a viral vector from a host cell, comprising: (i) contacting the composition comprising the viral vector and the transgene protein contaminant with a chromatography matrix capable of selectively binding the viral vector, (ii) eluting the viral vector (and any remaining transgene protein contaminant) from the second chromatography matrix, (iii) contacting the eluate of step (ii) with a first chromatography matrix capable of selectively binding the transgene protein contaminant; and (iv) recovering the viral vector in the flow-through of the chromatography matrix, thereby separating the viral vector from the transgene protein contaminant.

In certain embodiments, after conducting the transgene protein capture step and/or viral vector capture step, the viral vector composition may be subjected to one or more steps of ultrafiltration, in order to further concentrate the viral vector. The ultrafiltration step is sometimes referred to as diafiltration when used for buffer exchange. In certain embodiments, an ultrafiltration/diafiltration step comprises concentrating the vector and/or exchanging the buffer. Any filtration process, e.g., direct flow filtration, tangential flow filtration, is suitable for an ultrafiltration/diafiltration step of a viral vector production process described herein. In general, the filtration process concentrates vector by forcing a diluent through a filter such that the diluent is removed from the composition, but the vector is unable to pass through the filter, thereby resulting in a concentrated vector composition. In certain embodiments, tangential flow filtration (TFF) is employed in the ultrafiltration/diafiltration step. TFF systems are composed of three distinct process streams: the feed solution, the permeate and the retentate (e.g., retentate containing the viral vector). Those of skill in the art will readily factor in considerations regarding fluid characteristics, sample volumes, and processing times, in order to select the optimal membrane and device for us in TFF applications for the purpose of concentration the vector and/or exchanging the buffer. For example, a membrane with molecular weight cut off that is three to six times smaller than the molecular weight of the viral vector to be retained is typically selected for use in filtration systems. Membranes can be flat sheets or hollow fibers.

In certain embodiments, wherein the viral vector capture step follows the transgene protein capture step, the eluate from the viral vector capture step is concentrated and further purified by ultrafiltration/diafilturation (UF/DF). In other embodiments, where the transgene protein capture step follows the viral vector capture step, the eluate from the transgene protein capture step is concentrated and further purified by UF/DF. In certain embodiments, the eluate may first be diluted before subjecting it to UF/DF. In certain embodiments, dilution of the eluant of the first purification step comprises the use of a diluent buffer, e.g., a diluent buffer comprising 20 mM Tris or 20 mM phosphate, 2 mM $MgCl_2$, 30 mM to 120 mM $CaCl_2$), and having a pH of 6.5 to 7.5. In certain embodiments, the diluent buffer is chilled prior to dilution (having a temperature <15° C.). In certain embodiments, post dilution conductivity is 20 to 40 mS/cm.

In various embodiments described herein, prior to loading a sample to carry out the transgene protein capture step of the invention, the load sample may be adjusted to a suitable loading condition. As used herein, the term "load sample" refers to the sample that is applied to the downstream chromatography matrix. For example, an anion exchange chromatography load sample refers to the sample that is applied to the downstream anion exchange chromatography matrix. As another example, an affinity chromatography load sample refers to the sample that is applied to the downstream affinity chromatography matrix.

Figure 6A:
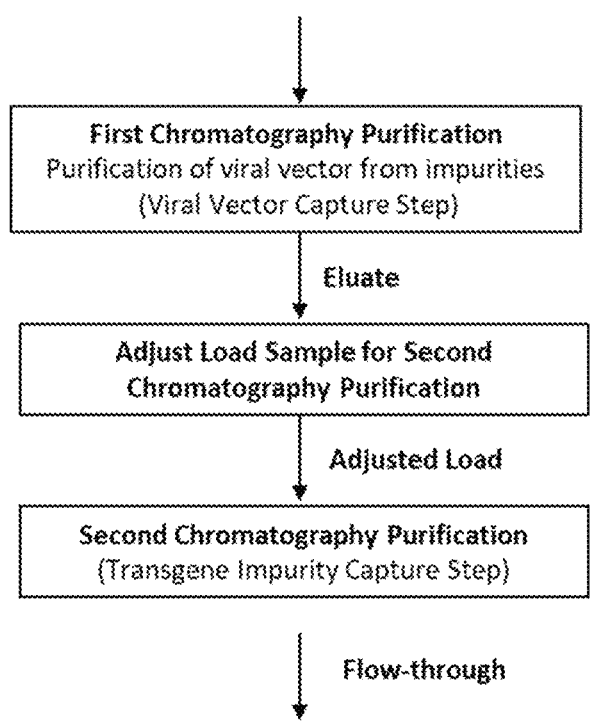
FIGS. 6A-6B show schematics of a downstream process work flow to manufacture an enveloped viral vector drug substance for gene therapy applications, according to one embodiment of the invention.

In an exemplary embodiment, as shown in FIG. 6A, where the downstream processing steps for viral vector production comprises a transgene protein capture step that follows a viral vector capture step, the eluate of the viral vector capture step (first chromatography purification step;

the eluate of the viral vector capture step is also referred to herein as the load sample for the transgene protein capture step) is adjusted to a suitable loading condition before being applied to the transgene protein capture chromatography matrix. In such an embodiment, the load sample for the transgene protein capture step (i.e., eluate of the viral vector capture step) is obtained by eluting bound vector from the viral vector capture chromatography matrix (e.g., anion exchange media) using elution buffer that has a salt (e.g., NaCl or KCl) concentration from about 300 mM to about 1,500 mM. The load sample for the transgene protein capture step is then adjusted to suitable loading conditions as described herein.

Figure 6B:
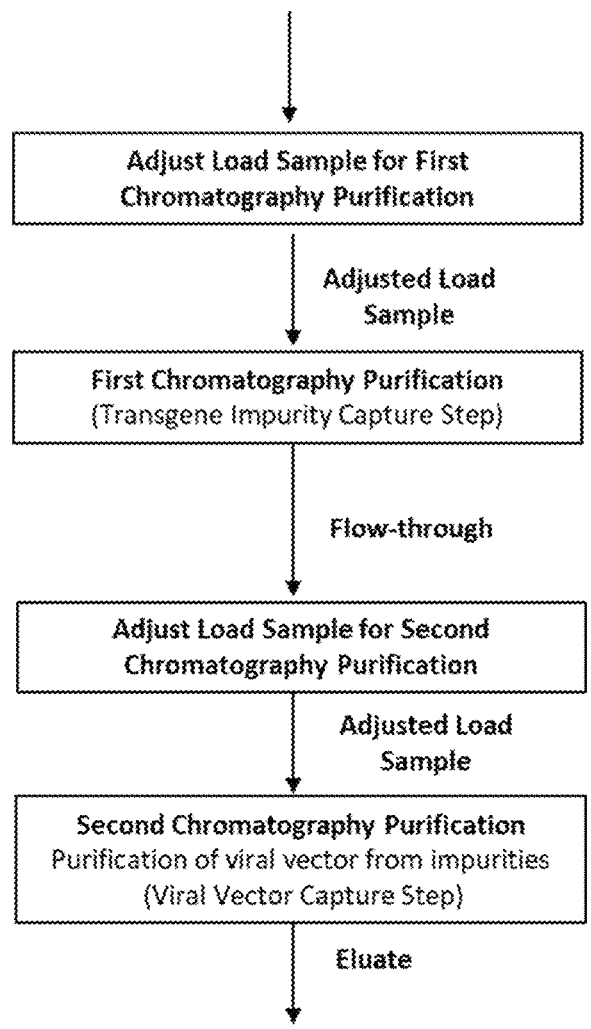

In another embodiment, as shown in FIG. 6B, where the downstream processing steps for viral vector production comprises a viral vector capture step that follows a transgene protein capture step, the load sample for the transgene protein capture step is adjusted to a suitable loading condition before being applied to the transgene protein capture chromatography matrix. After collecting the flow-through from the transgene protein capture step (flow-through that contains the purified viral vector), the flow-through sample may be adjusted to a suitable loading condition for applying to the subsequent viral vector capture chromatography matrix. In certain embodiments, the flow-through sample of the transgene protein capture step (e.g., load sample for a viral vector capture step) is adjusted to a target salt concentration to achieve a target sample conductivity of less than 20 mS/cm.

As such, in certain embodiments, the downstream processing steps for viral vector production described in the present disclosure comprises the step of adjusting the concentration of a salt of the composition comprising the viral vector and the transgene protein contaminant to a target salt concentration.

In certain embodiments, the adjusting of the load sample for the transgene protein capture step comprises adjusting the concentration of a salt to a target salt concentration. Adjustment of the load sample for the transgene protein capture step may comprise adjusting the concentration of salt and ionic components, including, without limitation, NaCl, KCl, CaCl$_2$), and MgCl$_2$. In some embodiments, adjusting of the load sample for the transgene protein capture step comprises diluting the load sample by a factor of 1:0, 1:1, 1:2, 1:3, 1:4, 1:5, 1:6, 1:7, 1:8, 1:9, 1:10, and the like, to decrease the concentration of salt in the load sample to a target salt concentration. In some embodiments, adjusting of the load sample for the transgene protein capture step comprises addition of salt (e.g., via bolus addition of stock salt) to increase the concentration of salt in the load sample to a target salt concentration. Those of ordinary skill in the art will readily be able to determine the amount of dilution required, or the amount of salt that is needed to be added to the load sample to achieve the target salt concentration suitable for applying to the transgene protein capture chromatography matrix. The adjusted load sample for the transgene protein capture step may have a target salt concentration of from about 200 mM (0.2 M) and about 600 mM (0.6 M). For example, in certain embodiments, the target salt concentration is about 200 mM, about 250 mM, about 300 mM, about 350 mM, about 400 mM, about 450 mM, about 500 mM, about 550 mM, about 600 mM. In certain exemplary embodiments, the target salt concentration is about 400 mM. In some embodiments, the salt in the load sample for the transgene protein capture step is NaCl or KCl. As such, in some embodiments, the adjusted load sample for the transgene protein capture step may have a target salt concentration of from about 200 mM NaCl and about 600 mM NaCl. In certain exemplary embodiments, the adjusted load sample for the transgene protein capture step has a target NaCl concentration of about 400 mM. In other embodiments, the adjusted load sample for the transgene protein capture step may have a target salt concentration of from about 200 mM KCl and about 600 mM KCl. In certain exemplary embodiments, the adjusted load sample for the transgene protein capture step has a target KCl concentration of about 400 mM. Without being bound to any theory, adjusting the salt concentration of the load sample for the transgene protein capture step of the invention may improve the efficiency of the transgene protein capture step by providing an optimal salt concentration in which the viral vector is separated from any bound contaminating transgene protein.

Addition to or dilution of the load sample for the transgene protein capture step to adjust for other ionic components and/or excipients may be performed to facilitate optimal removal of contaminating transgene protein in a transgene protein capture step of the invention. Buffer systems such as Tris, phosphate, bis-Tris, or other buffer systems known in the art suitable for a transgene protein capture step of the invention may be used. Such buffer systems may contain excipients such as sugar (e.g., sucrose), Poloxamer, polysorbate, and other suitable excipients known in the art. In certain embodiments, the buffer system also contains one or more ionic components such as MgCl$_2$, CaCl$_2$), or others known in the art to enhance the efficiency of transgene protein capture and removal in a transgene protein capture step of the invention. In certain exemplary embodiments, ionic components such as MgCl$_2$ and CaCl$_2$ may be adjusted to a target concentration of from 0 mM to about 20 mM. In certain exemplary embodiments, a suitable adjusted load sample for the transgene protein capture step of the invention may comprise from about 200 mM to about 600 mM of NaCl or KCl, from about 0 mM to about 20 mM MgCl2 or CaCl2, and may or may not contain excipients such as sugar (e.g., sucrose), Poloxamer, polysorbate, and/or any other excipients known in the art to be suitable.

The adjusted load sample for the transgene protein capture step of the invention may be stored at a lower temperature for temporary hold depending on processing need. In certain embodiments, the adjusted load sample is applied directly to the transgene protein capture chromatography matrix. Suitable conditions (e.g., temperature from about 4° C. to about 25° C.) for carrying out the transgene protein capture step of the invention are known to those of skill in the art, and may be provided by the manufacturer of the transgene protein capture chromatography matrix. The adjusted sample is loaded into the transgene protein capture chromatography matrix (e.g., transgene protein capture chromatography column) at a residence time value ranging from about 4 to about 12 minutes, allowing for sufficient time to elapse in order for the transgene protein contaminant to be retained within the transgene protein capture chromatography matrix. The unbound viral vector particles flow through the matrix, resulting in a purified viral vector product. To recover any remaining viral vector particles from the chromatography matrix (e.g., void space of a packed column), a chase of equilibration buffer is applied to the chromatography matrix and the flow-through is collected until a desired level of viral vector particles has been obtained.

At this stage in a viral production process described herein, the viral vector composition (i.e., viral vector eluate) is combined with one or more pharmaceutical excipients to make a pharmaceutical composition, which is then optionally subjected to filter sterilization to render the composition suitable for clinical use. Various filter sterilization processes and sterilizing filters are known to those of skill in the art. Accordingly, a viral vector production process described herein comprises combining the viral vector separated from the transgene protein contaminant (e.g., viral vector eluate) with one or more pharmaceutical excipients to make a pharmaceutical composition comprising the viral vector. In certain embodiments, the combining of viral vector separated from the transgene protein contaminant (e.g., viral vector eluate) with one or more pharmaceutical excipients is achieved through UF/DF of the viral vector separated from the transgene protein contaminant (e.g., viral vector eluate) with a formulation buffer.

In certain embodiments, a viral vector production process described herein results in a composition comprising a viral vector, wherein the composition is substantially free of a transgene protein contaminant. As used herein, the term "substantially free of a transgene protein contaminant" refers to a composition comprising less than about 50% of the amount of transgene protein contaminant that is present in a reference viral vector composition purified without a transgene protein capture step of the invention (e.g., a viral vector composition purified according to a conventional purification process that employs a viral vector capture step but not a transgene protein capture step). For example, a composition is substantially free of a transgene protein contaminant when the composition comprises less than about 45%, less than about 40%, less than about 35%, less than about 30%, less than about 25%, less than about 20%, less than about 15%, less than about 10%, or less than about 5% of the amount of transgene protein contaminant present in the reference viral vector composition. In certain embodiments, the composition contains less than 20% of the transgene protein contaminant present in the reference viral vector composition.

Various methods of assaying the amount of a transgene protein contaminant are known to those of skill in the art and are suitable. In certain embodiments, for a transgene protein contaminant having a specific activity (e.g., an enzymatic activity), the activity of the transgene protein contaminant in the composition of the invention can be assayed and compared to the activity of the transgene protein contaminant in a reference viral vector composition. For example, the level of FVIII transgene activity (mU/ml) can be assayed by a variety of chromogenic assays known to those of skill in the art. In certain embodiments, the purified FVIII viral vector composition of the invention comprises less than 50000 mU/ml of FVIII activity (e.g., less than 40000, 30000, 20000, 10000 or 500 mU of FVIII activity). In certain exemplary embodiments, the purified FVIII viral vector composition of the invention comprises a total FVIII activity of about 1 IU or less.

In certain embodiments, the amount of a transgene protein contaminant can be detected via various techniques known in the art to quantify the presence of actual contaminant protein. In certain embodiments, the presence of the transgene protein contaminant in the composition of the invention can be assayed and compared to the presence of the transgene protein contaminant in a reference viral vector composition. For example, an enzyme-linked immunosorbent assay (ELISA) can be performed to detect the presence of a transgene protein contaminant. Other examples that may be suitable include spectrometry methods (e.g., high-performance liquid chromatography (HPLC), and liquid chromatography-mass spectrometry (LC/MS), etc.), and antibody-based methods of protein detection (e.g., protein immunoprecipitation, immunoelectrophoresis, etc.).

B. Viral Vectors

The methods and processes provided herein are suitable for the production and purification of any viral vector. In certain embodiments, the viral vector is an enveloped viral vector. As known in the art enveloped viral vectors include, without limitation, enveloped DNA viral vectors, e.g., herpesvirus and poxvirus, and enveloped RNA viral vectors, e.g., alphavirus and paramyxovirus. Enveloped viral vectors also include retroviruses, e.g., oncoretroviruses, lentiviruses, and spumaviruses. In certain embodiments, the enveloped viral vector is a lentiviral vector. Lentiviral vectors are part of a larger group of retroviral vectors (Coffin et al. (1997) "Retroviruses" Cold Spring Harbor Laboratory Press Eds: J M Coffin, S M Hughes, H E Varmus pp 758-763). Examples of primate lentiviruses include: the human immunodeficiency virus (HIV) and the simian immunodeficiency virus (SIV). The lentivirus family differs from retroviruses in that lentiviruses have the capability to infect both dividing and non-dividing cells (Lewis et al. (1992); Lewis and Emerman (1994)).

As used herein, the term "lentiviral vector" refers to a vector which comprises at least one component part derivable from a lentivirus. In some embodiments, the component part is involved in the biological mechanisms by which the vector infects cells, expresses genes or is replicated. In some embodiments, a recombinant lentiviral vector at least part of one or more protein coding regions essential for replication may be removed from the virus. Accordingly, in some embodiments, recombinant lentiviral vectors are replication-defective. Portions of the viral genome may also be replaced by a transgene, thus rendering the vector capable of transducing a target non-dividing host cell and/or integrating its genome into a host genome.

In certain embodiments, a recombinant enveloped virus (e.g., a recombinant lentivirus) is pseudotyped to alter or modify the tropism of the recombinant lentiviral vector. Pseudotyping can confer one or more advantages. For example, the env gene product of the HIV based vectors would restrict these vectors to infecting only cells that express a protein called CD4. In some embodiments, if the env gene in these vectors has been substituted with env sequences from other RNA viruses, this may confer a broader infectious spectrum (Verma and Somia (1997)). The envelope glycoprotein (G) of Vesicular stomatitis virus (VSV), a rhabdovirus, is an envelope protein that has been shown to be capable of pseudotyping certain retroviruses. Pseudotyped VSV-G vectors may be used to transduce a wide range of mammalian cells. The incorporation of a non-lentiviral pseudotyping envelope, such as VSV-G protein, gives the advantage that vector particles can be concentrated to a high titre without loss of infectivity (Akkina et al. (1996) J. Virol. 70:2581-5).

Lentiviruses include members of the bovine lentivirus group, equine lentivirus group, feline lentivirus group, ovine lentivirus group, caprine lentivirus group, and primate lentivirus group. The development of lentivirus vectors for gene therapy has been reviewed in Klimatcheva et al. (1999) Frontiers in Bioscience 4:481-496. The design and use of lentiviral vectors suitable for gene therapy is described for example in U.S. Pat. Nos. 6,207,455 and 6,615,782. Examples of lentiviruses include, but are not limited to, HIV-1, HIV-2, HIV-1/HIV-2 pseudotype, HIV-1/SIV, FIV, caprine arthritis encephalitis virus (CAEV), equine infectious anemia virus, and bovine immunodeficiency virus.

In some embodiments, a lentiviral vector is a "third-generation" lentiviral vector. As used herein, the term "third-generation" lentiviral vector refers to a lentiviral packaging system that has the characteristics of a second-generation vector system, and that further lacks a functional tat gene, such as one from which the tat gene has been deleted or inactivated. Typically, the gene encoding rev is provided on a separate expression construct. See, e.g., Dull et al. (1998) J. Virol. 72: 8463-8471. As used herein, a "second-generation" lentiviral vector system refers to a lentiviral packaging system that lacks functional accessory genes, such as one from which the accessory genes vif, vpr, vpu, and nef have been deleted or inactivated. See, e.g., Zufferey et al. (1997) Nat. Biotechnol. 15:871-875. As used herein, "packaging system" refers to a set of viral constructs comprising genes that encode viral proteins involved in packaging a recombinant virus. Typically, the constructs of the packaging system will ultimately be incorporated into a packaging cell.

In certain embodiments, the lentiviral vector is a vector of a recombinant lentivirus capable of infecting non-dividing cells. In certain embodiments, the lentiviral vector is a vector of a recombinant lentivirus capable of infecting liver cells (e.g., hepatocytes). The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The κ' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV). Adjacent to the 5' LTR are sequences necessary for reverse transcription of the genome (the tRNA primer binding site) and for efficient encapsidation of viral RNA into particles (the Psi site).

In some embodiments, a method of producing a recombinant lentivirus capable of infecting a non-dividing cell comprises transfecting a suitable host cell with two or more vectors carrying the packaging functions, namely gag, pol and env, as well as rev and tat. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV-G), that of hepatitis viruses and of influenza also can be used.

In certain embodiments, a lentiviral vector of the instant disclosure comprises one or more nucleotide sequences encoding a gag protein, a Rev-response element, a central polypurine track (cPPT), or any combination thereof.

In some embodiments, the lentiviral vector expresses on its surface one or more polypeptides that improve the targeting and/or activity of the lentiviral vector or the encoded FVIII polypeptide. The one or more polypeptides can be encoded by the lentiviral vector or can be incorporated during budding of the lentiviral vector from a host cell. During lentiviral production, viral particles bud off from a producing host cell. During the budding process, the viral particle takes on a lipid coat, which is derived from the lipid membrane of the host cell. As a result, the lipid coat of the viral particle can include membrane bound polypeptides that were previously present on the surface of the host cell.

In some embodiments, the lentiviral vector expresses one or more polypeptides on its surface that inhibit an immune response to the lentiviral vector following administration to a human subject. In some embodiments, the surface of the lentiviral vector comprises one or more CD47 molecules. CD47 is a "marker of self" protein, which is ubiquitously expressed on human cells. Surface expression of CD47 inhibits macrophage-induced phagocytosis of endogenous cells through the interaction of CD47 and macrophage expressed-SIRPα. Cells expressing high levels of CD47 are less likely to be targeted and destroyed by human macrophages in vivo.

In some embodiments, the lentiviral vector comprises a high concentration of CD47 polypeptide molecules on its surface. In some embodiments, the lentiviral vector is produced in a cell line that has a high expression level of CD47. In certain embodiments, the lentiviral vector is produced in a $CD47^{high}$ cell, wherein the cell has high expression of CD47 on the cell membrane. In particular embodiments, the lentiviral vector is produced in a $CD47^{high}$ HEK 293T cell, wherein the HEK 293T is has high expression of CD47 on the cell membrane. In some embodiments, the HEK 293T cell is modified to have increased expression of CD47 relative to unmodified HEK 293T cells. In certain embodiments, the CD47 is human CD47.

In some embodiments, the lentiviral vector has little or no surface expression of major histocompatibility complex class I (MHC-I). Surface expressed MHC-I displays peptide fragments of "non-self" proteins from within a cell, such as protein fragments indicative of an infection, facilitating an immune response against the cell. In some embodiments, the lentiviral vector is produced in a MHC-$I^{low}$ cell, wherein the cell has reduced expression of MHC-I on the cell membrane. In some embodiments, the lentiviral vector is produced in an MHC-I⁻ (or "MHC-$I^{free}$", "MHC-$1^{neg}$" or "MHC-negative") cell, wherein the cell lacks expression of MHC-I.

In particular embodiments, the lentiviral vector comprises a lipid coat comprising a high concentration of CD47 polypeptides and lacking MHC-I polypeptides. In certain embodiments, the lentiviral vector is produced in a $CD47^{high}$/MHC-$I^{low}$ cell line, e.g., a $CD47^{high}$/MHC-$I^{low}$ HEK 293 T cell line. In some embodiments, the lentiviral vector is produced in a $CD47^{high}$/MHC-$I^{free}$ cell line, e.g., a $CD47^{high}$/MHC-$I^{free}$ HEK 293T cell line.

Examples of lentiviral vectors are disclosed in U.S. Pat. No. 9,050,269 and International Publication Nos. WO9931251, WO9712622, WO9817815, WO9817816, and WO9818934, which are incorporated herein by reference in their entireties.

Expression Control Elements

In some embodiments, the nucleic acid molecule or vector of the disclosure further comprises at least one expression control sequence. An expression control sequence as used herein is any regulatory nucleotide sequence, such as a promoter sequence or promoter-enhancer combination, which facilitates the efficient transcription and translation of the coding nucleic acid to which it is operably linked. For example, the isolated nucleic acid molecule of the disclosure can be operably linked to at least one transcription control sequence.

The gene expression control sequence can, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus.

Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In one embodiment, the disclosure includes expression of a transgene under the control of a tissue specific promoter and/or enhancer. In another embodiment, the promoter or other expression control sequence selectively enhances expression of the transgene in liver cells. Examples of liver specific promoters include, but are not limited to, a mouse thyretin promoter (mTTR), an endogenous human factor VIII (F8) promoter, an endogenous human factor IX (F9) promoter, human alpha-1-antitrypsin promoter (hAAT), human albumin minimal promoter, and mouse albumin promoter. In a particular embodiment, the promoter comprises a mTTR promoter. The mTTR promoter is described in R. H. Costa et al., 1986, *Mol. Cell. Biol.* 6:4697. The F8 promoter is described in Figueiredo and Brownlee, 1995, *J. Biol. Chem.* 270:11828-11838. In certain embodiments, the promoter comprises any of the mTTR promoters (e.g., mTTR202 promoter, mTTR202opt promoter, mTTR482 promoter) as disclosed in U.S. patent publication no. US2019/0048362, which is incorporated by reference herein in its entirety.

Expression levels can be further enhanced to achieve therapeutic efficacy using one or more enhancers. One or more enhancers can be provided either alone or together with one or more promoter elements. Typically, the expression control sequence comprises a plurality of enhancer elements and a tissue specific promoter. In one embodiment, an enhancer comprises one or more copies of the α-1-microglobulin/bikunin enhancer (Rouet et al., 1992, *J. Biol. Chem.* 267:20765-20773; Rouet et al., 1995, *Nucleic Acids Res.* 23:395-404; Rouet et al., 1998, *Biochem. J.* 334:577-584; Ill et al., 1997, *Blood Coagulation Fibrinolysis* 8:S23-S30). In another embodiment, an enhancer is derived from liver specific transcription factor binding sites, such as EBP, DBP, HNF1, HNF3, HNF4, HNF6, with Enhl, comprising HNF1, (sense)-HNF3, (sense)-HNF4, (antisense)-HNF 1, (anti sense)-HNF6, (sense)-EBP, (anti sense)-HNF4 (anti sense).

In a particular example, a promoter useful for the disclosure is an ET promoter, which is also known as GenBank No. AY661265. See also Vigna et al., *Molecular Therapy* 11(5):763 (2005). Examples of other suitable vectors and gene regulatory elements are described in WO 02/092134, EP1395293, or U.S. Pat. Nos. 6,808,905, 7,745,179, or 7,179,903, which are incorporated by reference herein in their entireties.

In general, the expression control sequences shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined coding nucleic acid. The gene expression sequences optionally include enhancer sequences or upstream activator sequences as desired.

In certain embodiments, it will be useful to include within the lentiviral vector one or more miRNA target sequences which, for example, are operably linked to a transgene within a lentiviral vector. More than one copy of a miRNA target sequence included in the lentiviral vector can increase the effectiveness of the system.

Also included are different miRNA target sequences. For example, lentiviral vectors which express more than one transgene can have the transgene under control of more than one miRNA target sequence, which can be the same or different. The miRNA target sequences can be in tandem, but other arrangements are also included. The transgene expression cassette, containing miRNA target sequences, can also be inserted within the lentiviral vector in antisense orientation. Antisense orientation can be useful in the production of viral particles to avoid expression of gene products which can otherwise be toxic to the producer cells.

In other embodiments, the lentiviral vector comprises 1, 2, 3, 4, 5, 6, 7 or 8 copies of the same or different miRNA target sequence. In certain embodiments, the lentiviral vector does not include any miRNA target sequence. Choice of whether or not to include an miRNA target sequence (and how many) will be guided by known parameters such as the intended tissue target, the level of expression required, etc.

In one embodiment, the target sequence is an miR-223 target which has been reported to block expression most effectively in myeloid committed progenitors and at least partially in the more primitive HSPC. miR-223 target can block expression in differentiated myeloid cells including granulocytes, monocytes, macrophages, myeloid dendritic cells. miR-223 target can also be suitable for gene therapy applications relying on robust transgene expression in the lymphoid or erythroid lineage. miR-223 target can also block expression very effectively in human HSC.

In another embodiment, the target sequence is an miR-142 target (tccataaagtaggaaacactaca (SEQ ID NO: 7)). In one embodiment, the lentiviral vector comprises 4 copies of miR-142 target sequences. In certain embodiments, the complementary sequence of hematopoietic-specific microRNAs, such as miR-142 (142T), is incorporated into the 3' untranslated region of a lentiviral vector, making the transgene-encoding transcript susceptible to miRNA-mediated down-regulation. By this method, transgene expression can be prevented in hematopoietic-lineage antigen presenting cells (APC), while being maintained in non-hematopoietic cells (Brown et al., Nat Med 2006). This strategy can impose a stringent post-transcriptional control on transgene expression and thus enables stable delivery and long-term expression of transgenes. In some embodiments, miR-142 regulation prevents immune-mediated clearance of transduced cells and/or induce antigen-specific Regulatory T cells (T regs) and mediate robust immunological tolerance to the transgene-encoded antigen.

In some embodiments, the target sequence is an miR181 target. Chen C-Z and Lodish H, Seminars in Immunology (2005) 17(2):155-165 discloses miR-181, a miRNA specifically expressed in B cells within mouse bone marrow (Chen and Lodish, 2005). It also discloses that some human miRNAs are linked to leukemias.

The target sequence can be fully or partially complementary to the miRNA. The term "fully complementary" means that the target sequence has a nucleic acid sequence which is 100% complementary to the sequence of the miRNA which recognizes it. The term "partially complementary" means that the target sequence is only in part complementary to the sequence of the miRNA which recognizes it, whereby the partially complementary sequence is still recognized by the miRNA. In other words, a partially complementary target sequence in the context of the present disclosure is effective in recognizing the corresponding miRNA and effecting prevention or reduction of transgene expression in cells expressing that miRNA. Examples of the miRNA target sequences are described at WO2007/000668, WO2004/094642, WO2010/055413, or WO2010/125471, which are incorporated herein by reference in their entireties.

In some embodiments, a suitable third-generation lentiviral vector is a self-inactivating lentiviral vector. In some embodiments, the lentiviral vector is a VSV.G pseudo type lentiviral vector. In some embodiments, the lentiviral vector comprises a hepatocyte-specific promoter for transgene expression. In some embodiments, the hepatocyte-specific promoter is an enhanced transthyretin promoter. In some embodiments, the lentiviral vector comprises one or more target sequences for miR-142 to reduce immune response to the transgene product. In some embodiments, incorporating one or more target sequences for miR-142 into a lentiviral vector of the present disclosure allows for a desired transgene expression profile. For example, incorporating one or more target sequences for miR-142 may suppress transgene expression in intravascular and extravascular hematopoietic lineages, whereas transgene expression is maintained in nonhematopoietic cells.

C. Viral Vector Transgenes

A viral vector suitable for a method described herein comprises a transgene expression cassette encoding a transgene protein, e.g., therapeutic protein, for treatment of a disease or disorder in a subject suffering therefrom. When the viral vector is administered to the subject in vivo, the viral vector transduces cells of the subject with the transgene expression cassette such that the protein product of the transgene in expressed in the subject as desired. However, if the transgene is expressed during the viral vector production process ex vivo, the transgene protein is considered a contaminant that can co-purify with the virus. Therefore, the methods of the invention may be employed to remove the transgene protein contaminant.

The transgene protein contaminant may correspond to any transgene of interest. In certain embodiments, the transgene may encode a protein selected from a clotting factor, a growth factor, an antibody, or a metabolic enzyme. As used herein, the term "clotting factor," refers to molecules, or analogs thereof, naturally occurring or recombinantly produced, which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. "Clotting factor" as used herein includes an activated clotting factor, its zymogen, or an activatable clotting factor. An "activatable clotting factor" is a clotting factor in an inactive form (e.g., in its zymogen form) that is capable of being converted to an active form. The term "clotting factor" includes but is not limited to factor I (FI), factor II (FII), factor V (FV), FVII, FVIII, FIX, factor X (FX), factor XI (FXI), factor XII (FXII), factor XIII (FXIII), Von Willebrand factor (VWF), prekallikrein, high-molecular weight kininogen, fibronectin, antithrombin III, heparin cofactor II, protein C, protein S, protein Z, Protein Z-related protease inhibitor (ZPI), plasminogen, alpha 2-antiplasmin, tissue plasminogen activator (tPA), urokinase, plasminogen activator inhibitor-1 (PAM), plasminogen activator inhibitor-2 (PAI2), zymogens thereof, activated forms thereof, or any combination thereof. In certain embodiments, the clotting factor comprises FVIII or a variant or fragment thereof. In other embodiments, the clotting factor comprises FVIIIXTEN or a variant or fragment thereof. In certain embodiments, the clotting factor comprises FIX or a variant or fragment thereof.

In some embodiments, the transgene encodes heterologous amino acid sequence. The heterologous amino acid sequence can be linked to the N-terminus or the C-terminus of the FVIII amino acid sequence or the FIX amino acid sequence or inserted between two amino acids in the FVIII amino acid sequence or the FIX amino acid sequence. In some embodiments, the heterologous amino acid sequence can be inserted within the FVIII polypeptide at any site disclosed in International Publication No. WO 2013/123457 A1 and WO 2015/106052 A1 or U.S. Publication No. 2015/0158929 A1, which are herein incorporated by reference in their entirety.

In some embodiments, the heterologous amino acid sequence is inserted within the B domain of FVIII or a fragment thereof. In some embodiments, the heterologous amino acid sequence is inserted within the FVIII immediately downstream of an amino acid corresponding to amino acid 745 of mature human FVIII (SEQ ID NO:4). In one particular embodiment, the FVIII comprises a deletion of amino acids 746-1646, corresponding to mature human FVIII, and the heterologous amino acid sequence is inserted immediately downstream of amino acid 745, corresponding to mature human FVIII.

In some embodiments, a heterologous moiety comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

In some embodiments, the XTEN sequence useful for the disclosure is a peptide or a polypeptide having greater than about 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, or 2000 amino acid residues. In certain embodiments, XTEN is a peptide or a polypeptide having greater than about 20 to about 3000 amino acid residues, greater than 30 to about 2500 residues, greater than 40 to about 2000 residues, greater than 50 to about 1500 residues, greater than 60 to about 1000 residues, greater than 70 to about 900 residues, greater than 80 to about 800 residues, greater than 90 to about 700 residues, greater than 100 to about 600 residues, greater than 110 to about 500 residues, or greater than 120 to about 400 residues. In one particular embodiment, the XTEN comprises an amino acid sequence of longer than 42 amino acids and shorter than 144 amino acids in length.

The XTEN sequence of the disclosure can comprise one or more sequence motifs of 5 to 14 (e.g., 9 to 14) amino acid residues or an amino acid sequence at least 80%, 90%, 91%, 92%, 93%, 94%, 95%, 96%, 97%, 98%, or 99% identical to the sequence motif, wherein the motif comprises, consists essentially of, or consists of 4 to 6 types of amino acids (e.g., 5 amino acids) selected from the group consisting of glycine (G), alanine (A), serine (S), threonine (T), glutamate (E) and proline (P). Examples of XTEN sequences that can be used as heterologous moieties in chimeric proteins of the disclosure are disclosed, e.g., in U.S. Patent Publication Nos. 2010/0239554 A1, 2010/0323956 A1, 2011/0046060 A1, 2011/0046061 A1, 2011/0077199 A1, or 2011/0172146 A1, or International Patent Publication Nos. WO 2010/091122 A1, WO 2010/144502 A2, WO 2010/144508 A1, WO 2011/028228 A1, WO 2011/028229 A1, or WO 2011/028344 A2, each of which is incorporated by reference herein in its entirety.

In certain embodiments, the transgene comprises a FVIII coding sequence as shown in Table 1. In certain embodiments the transgene protein encoded by the transgene comprises an amino acid sequence as shown in Table 1.

TABLE 1

Sequences

| SEQ ID NO | Description | Sequence |
|---|---|---|
| 1 | FVIII coding sequence (non-codon optimized) | ATGCAGATTGAGCTGTCCACTTGTTTCTTCCTGTGCCTCCTGC GCTTCTGTTTCTCCGCCACTCGCCGGTACTACCTTGGAGCCGT GGAGCTTTCATGGGACTACATGCAGAGCGACCTGGGCGAACTC CCCGTGGATGCCAGATTCCCCCCCGCGTGCCAAAGTCCTTCC CCTTTAACACCTCCGTGGTGTACAAGAAAACCCTCTTTGTCGA GTTCACTGACCACCTGTTCAACATCGCCAAGCCGCGCCCACCT TGGATGGGCCTCCTGGGACCGACCATTCAAGCTGAAGTGTACG ACACCGTGGTGATCACCCTGAAGAACATGGCGTCCCACCCCGT GTCCCTGCATGCGGTCGGAGTGTCCTACTGGAAGGCCTCCGAA GGAGCTGAGTACGACGACCAGACTAGCCAGCGGGAAAAGGAGG ACGATAAAGTGTTCCCGGGCGGCTCGCATACTTACGTGTGGCA AGTCCTGAAGGAAAACGGACCTATGGCATCCGATCCTCTGTGC CTGACTTACTCCTACCTTTCCCATGTGGACCTCGTGAAGGACC TGAACAGCGGGCTGATTGGTGCACTTCTCGTGTGCCGCGAAGG TTCGCTCGCTAAGGAAAAGACCCAGACCCTCCATAAGTTCATC CTTTTGTTCGCTGTGTTCGATGAAGGAAAGTCATGGCATTCCG AAACTAAGAACTCGCTGATGCAGGACCGGGATGCCGCCTCAGC CCGCGCCTGGCCTAAAATGCATACAGTCAACGGATACGTGAAT CGGTCACTGCCCGGGCTCATCGGTTGTCACAGAAAGTCCGTGT ACTGGCACGTCATCGGCATGGGCACTACGCCTGAAGTGCACTC CATCTTCCTGGAAGGGCACACCTTCCTCGTGCGCAACCACCGC CAGGCCTCTCTGGAAATCTCCCCGATTACCTTTCTGACCGCCC AGACTCTGCTCATGGACCTGGGGCAGTTCCTTCTCTTCTGCCA CATCTCCAGCCATCAGCACGACGGAATGGAGGCCTACGTGAAG GTGGACTCATGCCCGGAAGAACCTCAGTTGCGGATGAAGAACA ACGAGGAGGCCGAGGACTATGACGACGATTTGACTGACTCCGA GATGGACGTCGTGCGGTTCGATGACGACAACAGCCCCAGCTTC ATCCAGATTCGCAGCGTGGCCAAGAAGCACCCCAAAACCTGGG TGCACTACATCGCGGCCGAGGAAGAAGATTGGGACTACGCCCC GTTGGTGCTGGCACCCGATGACCGGTCGTACAAGTCCCAGTAT CTGAACAATGGTCCGCAGCGGATTGGCAGAAAGTACAAGAAAG TGCGGTTCATGGCGTACACTGACGAAACGTTTAAGACCCGGGA GGCCATTCAACATGAGAGCGGCATTCTGGGACCACTGCTGTAC GGAGAGGTCGGCGATACCCTGCTCATCATCTTCAAAAACCAGG CCTCCCGGCCTTACAACATCTACCCTCACGGAATCACCGACGT GCGGCCACTCTACTCGCGGCGCCTGCCGAAGGGCGTCAAGCAC CTGAAAGACTTCCCTATCCTGCCGGGCGAAATCTTCAAGTATA AGTGGACCGTCACCGTGGAGGACGGGCCCACCAAGAGCGATCC TAGGTGTCTGACTCGGTACTACTCCAGCTTCGTGAACATGGAA CGGGACCTGGCATCGGGACTCATTGGACCGCTGCTGATCTGCT ACAAAGAGTCGGTGGATCAACGCGGCAACCAGATCATGTCCGA CAAGCGCAACGTGATCCTGTTCTCCGTGTTTGATGAAAACAGA TCCTGGTACCTCACTGAAAACATCCAGAGGTTCCTCCCAAACC CCGCAGGAGTGCAACTGGAGGACCCTGAGTTTCAGGCCTCGAA TATCATGCACTCGATTAACGGTTACGTGTTCGACTCGCTGCAG CTGAGCGTGTGCCTCCATGAAGTCGCTTACTGGTACATTCTGT CCATCGGCGCCCAGACTGACTTCCTGAGCGTGTTCTTTTCCGG TTACACCCTTTAAGCACAAGATGGTGTACGAAGATACCCTGACC CTGTTCCCTTTCTCCGGCGAAACGGTGTTCATGTCGATGGAGA ACCCGGGTCTGTGGATTCTGGGATGCCACAACAGCGACTTTCG GAACCGCGGAATGACTGCCCTGCTGAAGGTGTCCTCATGCGAC AAGAACACCGGAGACTACTACGAGGACTCCTACGAGGATATCT CAGCCTACCTCCTGTCCAAGAACAACGCGATCGAGCCGCGCAG CTTCAGCCAGAACCCGCCTGTGCTGAAGAGGCACCAGCGAGAA ATTACCCGGACCACCCTCCAATCGGATCAGGAGGAAATCGACT |

TABLE 1-continued

Sequences

| SEQ ID NO | Description | Sequence |
|---|---|---|
| | | ACGACGACACCATCTCGGTGGAAATGAAGAAGGAAGATTTCGA
TATCTACGACGAGGACGAAAATCAGTCCCCTCGCTCATTCCAA
AAGAAAACTAGACACTACTTTATCGCCGCGGTGGAAAGACTGT
GGGACTATGGAATGTCATCCAGCCCTCACGTCCTTCGGAACCG
GGCCCAGAGCGGATCGGTGCCTCAGTTCAAGAAAGTGGTGTTC
CAGGGAGTTCACCGACGGCAGCTTCACCCAGCCGCTGTACCGGG
GAGAACTGAACAACACCTGGGCCTGCTCGGTCCCTACATCCG
CGCGGAAGTGGAGGATAACATCATGGTGACCTTCCGTAACCAA
GCATCCAGACCTTACTCCTTCTATTCCTCCCTGATCTCATACG
AGGAGGACCAGCGCCAAGGCGCCGAGCCCCGCAAGAACTTCGT
CAAGCCCAACGAGACTAAGACCTACTTCTGGAAGGTCCAACAC
CATATGGCCCCGACCAAGGATGAGTTTGACTGCAAGGCCTGGG
CCTACTTCTCCGACGTGGACCTTGAGAAGGATGTCCATTCCGG
CCTGATCGGGCCGCTGCTCGTGTGTCACACCAACACCCTGAAC
CCAGCGCATGGACGCAGGTCACCGTCCAGGAGTTTGCTCTGT
TCTTCACCATTTTTGACGAAACTAAGTCCTGGTACTTCACCGA
GAATATGGAGCGAAACTGTAGAGCGCCCTGCAATATCCAGATG
GAAGATCCGACTTTCAAGGAGAACTATAGATTCCACGCCATCA
ACGGGTACATCATGGATACTCTGCCGGGGCTGGTCATGGCCCA
GGATCAGAGGATTCGGTGGTACTTGCTGTCAATGGGATCGAAC
GAAAACATTCACTCCATTCACTTCTCCGGTCACGTGTTCACTG
TGCGCAAGAAGGAGGAGTACAAGATGGCGCTGTACAATCTGTA
CCCCGGGGTGTTCGAAACTGTGGAGATGCTGCCGTCCAAGGCC
GGCATCTGGAGAGTGGAGTGCCTGATCGGAGAGCACCTCCACG
CGGGGATGTCCACCCTCTTCCTGGTGTACTCGAATAAGTGCCA
GACCCCGCTGGGCATGGCCTCGGGCCACATCAGAGACTTCCAG
ATCACAGCAAGCGGACAATACGGCCAATGGGCGCCGAAGCTGG
CCCGCTTGCACTACTCCGGATCGATCAACGCATGGTCCACCAA
GGAACCGTTCTCGTGGATTAAGGTGGACCTTCCTGGCCCCTATG
ATTATCCACGGAATTAAGACCCAGGGCGCCAGGCAGAAGTTCT
CCTCCCTGTACATCTCGCAATTCATCATCATGTACAGCCTGGA
CGGGAAGAAGTGGCAGACTTACAGGGGAAACTCCACCGGCACC
CTGATGGTCTTTTTCGGCAACGTGGATTCCTCCGGCATTAAGC
ACAACATCTTCAACCCACCGATCATAGCCAGATATATTAGGCT
CCACCCCACTCACTACTCAATCCGCTCAACTCTTCGGATGGAA
CTCATGGGGTGCGACCTGAACTCCTGCTCCATGCCGTTGGGGA
TGGAATCAAAGGCTATTAGCGACGCCCAGATCACCGCGAGCTC
CTACTTCACTAACATGTTCGCCACCTGGAGCCCCTCCAAGGCC
AGGCTGCACTTGCAGGGACGGTCAAATGCCTGGCGGCCGCAAG
TGAACAATCCGAAGGAATGGCTTCAAGTGGATTTCCAAAAGAC
CATGAAAGTGACCGGAGTCACCACCCAGGGAGTGAAGTCCCTT
CTGACCTCGATGTATGTGAAGGAGTTCCTGATTAGCAGCAGCC
AGGACGGGCACCAGTGGACCCTGTTCTTCCAAAACGGAAAGGT
CAAGGTGTTCCAGGGGAACCAGGACTCGTTCACACCCGTGGTG
AACTCCCTGGACCCCCCACTGCTGACGCGGTACTTGAGGATTC
ATCCTCAGTCCTGGGTCCATCAGATTGCATTGCGAATGGAAGT
CCTGGGCTGCGAGGCCCAGGACCTGTAC |
| 2 | FVIII coding sequence comprising XTEN (XTEN in bold and underline) (non-codon optimized) | ATGCAGATTGAGCTGTCCACTTGTTTCTTCCTGTGCCTCCTGC
GCTTCTGTTTCTCCGCCACTCGCCGGTACTACCTTGGAGCCGT
GGAGCTTTCATGGGACTACATGCAGAGCGACCTGGGCGAACTC
CCCGTGGATGCCAGATTCCCCCCCGCGTGCCAAAGTCCTTCC
CCTTTAACACCTCCGTGGTGTACAAGAAAACCCTCTTTGTCGA
GTTCACTGACCACCTGTTCAACATCGCCAAGCCGCGCCCACCT
TGGATGGGCCTCCTGGGACCGACCATTCAAGCTGAAGTGTACG
ACACCGTGGTGATCACCCTGAAGAACATGGCGTCCCACCCCGT
GTCCCTGCATGCGGTCGGAGTGTCCTACTGGAAGGCCTCCGAA
GGAGCTGAGTACGACGACCAGACTAGCCAGCGGGAAAAGGAGG
ACGATAAAGTGTTCCCGGGCGGCTCGCATACTTACGTGTGGCA
AGTCCTGAAGGAAAACGGACCTATGGCATCCGATCCTCTGTGC
CTGACTTACTCCTACCTTTCCCATGTGGACCTCGTGAAGGACC
TGAACAGCGGGCTGATTGGTGCACTTCTCGTGTGCCGCGAAGG
TTCGCTCGCTAAGGAAAAGACCCAGACCCTCCATAAGTTCATC
CTTTTGTTCGCTGTGTTCGATGAAGGAAAGTCATGGCATTCCG
AAACTAAGAACTCGCTGATGCAGGACCGGGATGCCGCCTCAGC
CCGCGCCTGGCCTAAAATGCATACAGTCAACGGATACGTGAAT
CGGTCACTGCCCGGGCTCATCGGTTGTCACAGAAAGTCCGTGT
ACTGGCACGTCATCGGCATGGGCACTACGCCTGAAGTGCACTC
CATCTTCCTGGAAGGGCACACCTTCCTCGTGCGCAACCACCGC
CAGGCCTCTCTGGAAATCTCCCCGATTACCTTTCTGACCGCCC
AGACTCTGCTCATGGACCTGGGGCAGTTCCTTCTCTTCTGCCA
CATCTCCAGCCATCAGCACGACGGAATGGAGGCCTACGTGAAG
GTGGACTCATGCCCGGAAGAACTCAGTTGCGGATGAAGAACA
ACGAGGAGGCCGAGGACTATGACGACGATTTGACTGACTCCGA
GATGGACGTCGTGCGGTTCGATGACGACAACAGCCCCCAGCTTC
ATCCAGATTCGCAGCGTGGCCAAGAAGCACCCCAAAACCTGGG |

TABLE 1-continued

Sequences

| SEQ ID NO | Description | Sequence |
|---|---|---|
| | | TGCACTACATCGCGGCCGAGGAAGAAGATTGGGACTACGCCCC |
| | | GTTGGTGCTGGCACCCGATGACCGGTCGTACAAGTCCCAGTAT |
| | | CTGAACAATGGTCCGCAGCGGATTGGCAGAAAGTACAAGAAAG |
| | | TGCGGTTCATGGCGTACACTGACGAAACGTTTAAGACCCGGGA |
| | | GGCCATTCAACATGAGAGCGGCATTCTGGGACCACTGCTGTAC |
| | | GGAGAGGTCGGCGATACCCTGCTCATCATCTTCAAAAACCAGG |
| | | CCTCCCGGCCTTACAACATCTACCCTCACGGAATCACCGACGT |
| | | GCGGCCACTCTACTCGCGGCGCCTGCCGAAGGGCGTCAAGCAC |
| | | CTGAAAGACTTCCCTATCCTGCCGGGCGAAATCTTCAAGTATA |
| | | AGTGGACCGTCACCGTGGAGGACGGGCCCACCAAGAGCGATCC |
| | | TAGGTGTCTGACTCGGTACTACTCCAGCTTCGTGAACATGGAA |
| | | CGGGACCTGGCATCGGGACTCATTGGACCGCTGCTGATCTGCT |
| | | ACAAAGAGTCGGTGGATCAACGCGGCAACCAGATCATGTCCGA |
| | | CAAGCGCAACGTGATCCTGTTCTCCGTGTTTGATGAAAACAGA |
| | | TCCTGGTACCTCACTGAAAACATCCAGAGGTTCCTCCCAAACC |
| | | CCGCAGGAGTGCAACTGGAGGACCCTGAGTTTCAGGCCTCGAA |
| | | TATCATGCACTCGATTAACGGTTACGTGTTCGACTCGCTGCAG |
| | | CTGAGCGTGTGCCTCCATGAAGTCGCTTACTGGTACATTCTGT |
| | | CCATCGGCGCCCAGACTGACTTCCTGAGCGTGTTCTTTTCCGG |
| | | TTACACCTTTAAGCACAAGATGGTGTACAAGATACCCTGACC |
| | | CTGTTCCCTTTCTCCGGCGAAACGGTGTTCATGTCGATGGAGA |
| | | ACCCGGGTCTGTGGATTCTGGGATGCCACAACAGCGACTTTCG |
| | | GAACCGCGGAATGACTGCCCTGCTGAAGGTGTCCTCATGCGAC |
| | | AAGAACACCGGAGACTACTACGAGGACTCCTACGAGGATATCT |
| | | CAGCCTACCTCCTGTCCAAGAACAACGCGATCGAGCCGCGCAG |
| | | CTTCAGCCAGAACACATCAGAGAGCGCCACCCCTGAAAGTGGT |
| | | CCCGGGAGCGAGCCAGCCACATCTGGGTCGGAAACGCCAGGCA |
| | | CAAGTGAGTCTGCAACTCCCGAGTCCGGACCTGGCTCCGAGCC |
| | | TGCCACTAGCGGCTCCGAGACTCCGGGAACTTCCGAGAGCGCT |
| | | ACACCAGAAAGCGGACCCGGAACCAGTACCGAACCTAGCGAGG |
| | | GCTCTGCTCCGGGCAGCCCAGCCGGCTCTCCTACATCCACGGA |
| | | GGAGGGCACTTCCGAATCCGCCACCCCGGAGTCAGGGCCAGGA |
| | | TCTGAACCCGCTACCTCAGGCAGTGAGACGCCAGGAACGAGCG |
| | | AGTCGCTACACCGGAGAGTGGGCCAGGGAGCCCTGCTGGATC |
| | | TCCTACGTCCACTGAGGAAGGGTCACCAGCGGGCTCGCCCACC |
| | | AGCACTGAAGAAGGTGCCTCGAGCCCGCCTGTGCTGAAGAGGC |
| | | ACCAGCGAGAAATTACCCGGACCACCCTCCAATCGGATCAGGA |
| | | GGAAATCGACTACGACGACACCATCTCGGTGGAAATGAAGAAG |
| | | GAAGATTTCGATATCTACGACGAGGACGAAAATCAGTCCCCTC |
| | | GCTCATTCCAAAAGAAAACTAGACACTACTTTATCGCCGCGGT |
| | | GGAAAGACTGTGGGACTATGGAATGTCATCCAGCCCTCACGTC |
| | | CTTCGGAACCGGGCCCAGAGCGGATCGGTGCCTCAGTTCAAGA |
| | | AAGTGGTGTTCCAGGAGTTCACCGACGGCAGCTTCACCCAGCC |
| | | GCTGTACCGGGGAGAACTGAACGAACACCTGGGCCTGCTCGGT |
| | | CCCTACATCCGCGCGGAAGTGGAGGATAACATCATGGTGACCT |
| | | TCCGTAACCAAGCATCCAGACCTTACTCCTTCTATTCCTCCCT |
| | | GATCTCATACGAGGAGGACCAGCGCCAAGGCGCCGAGCCCCGC |
| | | AAGAACTTCGTCAAGCCCAACGAGACTAAGACCTACTTCTGGA |
| | | AGGTCCAACACCATATGGCCCCGACCAAGGATGAGTTTGACTG |
| | | CAAGGCCTGGGCCTACTTCTCCGACGTGGACCTTGAGAAGGAT |
| | | GTCCATTCCGGCCTGATCGGGCCGCTGCTCGTGTGTCACACCA |
| | | ACACCCTGAACCCAGCGCATGGACGCCAGGTCACCGTCCAGGA |
| | | GTTTGCTCTGTTCTTCACCATTTTTGACGAAACTAAGTCCTGG |
| | | TACTTCACCGAGAATATGGAGCGAAACTGTAGAGCGCCCTGCA |
| | | ATATCCAGATGGAAGATCCGACTTTCAAGGAGAACTATAGATT |
| | | CCACGCCATCAACGGGTACATCATGGATACTCTGCCGGGGCTG |
| | | GTCATGGCCCAGGATCAGAGGATTCGGTGGTACTTGCTGTCAA |
| | | TGGGATCGAACGAAAACATTCACTCCATTCACTTCTCCGGTCA |
| | | CGTGTTCACTGTGCGCAAGAAGGAGGAGTACAAGATGGCGCTG |
| | | TACAATCTGTACCCCGGGGTGTTCGAAACTGTGGAGATGCTGC |
| | | CGTCCAAGGCCGGCATCTGGAGAGTGGAGTGCCTGATCGGAGA |
| | | GCACCTCCACGCGGGGATGTCCACCCTCTTCCTGGTGTACTCG |
| | | AATAAGTGCCAGACCCCGCTGGGCATGGCCTCGGGCCACATCA |
| | | GAGACTTCCAGATCACAGCAAGCGGACAATACGGCCAATGGGC |
| | | GCCGAAGCTGGCCCGCTTGCACTACTCCGGATCGATCAACGCA |
| | | TGGTCCACCAAGGAACCGTTCTCGTGGATTAAGGTGGACCTCC |
| | | TGGCCCCTATGATTATCCACGGAATTAAGACCCAGGGCGCCAG |
| | | GCAGAAGTTCTCCTCCCTGTACATCTCGCAATTCATCATCATG |
| | | TACAGCCTGGACGGGAAGAAGTGGCAGACTTACAGGGGAAACT |
| | | CCACCGGCACCCTGATGGTCTTTTTCGGCAACGTGGATTCCTC |
| | | CGGCATTAAGCACAACATCTTCAACCCACCGATCATAGCCAGA |
| | | TATATTAGGCTCCACCCCACTCACTACTCAATCCGCTCAACTC |
| | | TTCGGATGGAACTCATGGGTGCGACCTGAACTCCTGCTCCAT |
| | | GCCGTTGGGGATGGAATCAAAGGCTATTAGCGACGCCCAGATC |
| | | ACCGCGAGCTCCTACTTCACTAACATGTTCGCCACCTGGAGCC |
| | | CCTCCAAGGCCAGGCTGCACTTGCAGGGACGGTCAAATGCCTG |

TABLE 1-continued

Sequences

| SEQ ID NO | Description | Sequence |
|---|---|---|
| | | GCGGCCGCAAGTGAACAATCCGAAGGAATGGCTTCAAGTGGAT<br>TTCCAAAAGACCATGAAAGTGACCGGAGTCACCACCCAGGGAG<br>TGAAGTCCCTTCTGACCTCGATGTATGTGAAGGAGTTCCTGAT<br>TAGCAGCAGCCAGGACGGGCACCAGTGGACCCTGTTCTTCCAA<br>AACGGAAAGGTCAAGGTGTTCCAGGGGAACCAGGACTCGTTCA<br>CACCCGTGGTGAACTCCCTGGACCCCCCACTGCTGACGCGGTA<br>CTTGAGGATTCATCCTCAGTCCTGGGTCCATCAGATTGCATTG<br>CGAATGGAAGTCCTGGGCTGCGAGGCCCAGGACCTGTAC |
| 3 | FIX coding sequence comprising R338L mutation (signal peptide in bold and underline) (Non-codon optimized) | ATGCAGAGAGTCAACATGATTATGGCTGAGTCACCTGGGCTGA<br>TTACTATTTGCCTGCTGGGCTACCTGCTGTCCGCCGAGTGTAC<br>CGTGTTCCTGGACCATGAGAACGCAAATAAGATCCTGAACAGG<br>CCCAAAAGATACAATAGTGGGAAGCTGGAAGAATTTGTGCAGG<br>GCAACCTGGAGAGAGAATGCATGGAGGAAAAGTGTAGCTTCGA<br>GGAAGCCCGCGAGGTGTTTGAAAATACAGAGCGAACCACAGAG<br>TTCTGGAAGCAGTATGTGGACGGCGATCAGTGCGAGAGCAACC<br>CCTGTCTGAATGGCGGAAGTTGCAAAGACGATATCAACTCATA<br>CGAATGCTGGTGTCCTTTCGGGTTTGAAGGCAAAAATTGCGAG<br>CTGGACGTGACATGTAACATTAAGAATGGACGGTGCGAGCAGT<br>TTTGTAAAAACTCTGCCGATAATAAGGTGGTGTGCAGCTGTAC<br>TGAAGGATATCGCCTGGCTGAGAACCAGAAGTCCTGCGAACCA<br>GCAGTGCCCTTCCCTTGTGGAGGGTGAGCGTCTCCCAGACTT<br>CAAAACTGACCAGAGCAGAGACAGTGTTTCCCGACGTGGATTA<br>CGTCAACAGCACTGAGGCCGAAACCATCCTGGACAACATTACT<br>CAGTCTACCCAGAGTTTCAATGACTTTACTCGGGTGGTCGGGG<br>GCGAGGATGCTAAACCAGGCCAGTTCCCCTGGCAGGTGGTCCT<br>GAACGGAAAGGTGGATGCATTTTGCGGAGGGTCTATCGTGAAT<br>GAGAAATGGATTGTCACCGCCGCTCACTGCGTGGAAACCGGAG<br>TCAAGATCACAGTGGTCGCTGGGGAGCACAACATTGAGGAAAC<br>AGAACATACTGAGCAGAAGCGGAATGTGATCCGCATCATTCCT<br>CACCATAACTACAATGCAGCCATCAACAAATACAATCATGACA<br>TTGCCCTGCTGGAACTGGATGAGCCTCTGGTGCTGAACAGCTA<br>CGTCACTCCAATCTGCATTGCTGACAAAGAGTATACCAATATC<br>TTCCTGAAGTTTGGATCAGGGTACGTGAGCGGCTGGGGAAGAG<br>TCTTCCACAAGGGCAGGAGCGCCCTGGTGCTCCAGTATCTGCG<br>AGTGCCTCTGGTCGATCGAGCTACCTGTCTGCTCTCTACCAAG<br>TTTACAATCTACAACAACATGTTCTGCGCTGGGTTTCACGAGG<br>GAGGACGAGACTCCTGTCAGGGCGATTCTGGGGCCCACATGT<br>GACAGAGGTCGAAGGCACCAGCTTCCTGACTGGCATCATTTCC<br>TGGGGAGAGGAATGTGCAATGAAGGGAAAATACGGGATCTACA<br>CCAAAGTGAGCCGCTATGTGAACTGGATCAAGGAAAAAACCAA<br>ACTGACC |
| 4 | Mature FVIII polypeptide | ATRRYYLGAVELSWDYMQSDLGELPVDARFPPRVPKSFPFNTS<br>VVYKKTLFVEFTDHLFNIAKPRPPWMGLLGPTIQAEVYDTVVI<br>TLKNMASHPVSLHAVGVSYWKASEGAEYDDQTSQREKEDDKVF<br>PGGSHTYVWQVLKENGPMASDPLCLTYSYLSHVDLVKDLNSGL<br>IGALLVCREGSLAKEKTQTLHKFILLFAVFDEGKSWHSETKNS<br>LMQDRDAASARAWPKMHTVNGYVNRSLPGLIGCHRKSVYWHVI<br>GMGTTPEVHSIFLEGHTFLVRNHRQASLEISPITFLTAQTLLM<br>DLGQFLLFCHISSHQHDGMEAYVKVDSCPEEPQLRMKNNEEAE<br>DYDDDLTDSEMDVVRFDDDNSPSFIQIRSVAKKHPKTWVHYIA<br>AEEEDWDYAPLVLAPDDRSYKSQYLNNGPQRIGRKYKKVRFMA<br>YTDETFKTREAIQHESGILGPLLYGEVGDTLLIIFKNQASRPY<br>NIYPHGITDVRPLYSRRLPKGVKHLKDFPILPGEIFKYKWTVT<br>VEDGPTKSDPRCLTRYYSSFVNMERDLASGLIGPLLICYKESV<br>DQRGNQIMSDKRNVILFSVFDENRSWYLTENIQRFLPNPAGVQ<br>LEDPEFQASNIMHSINGYVFDSLQLSVCLHEVAYWYILSIGAQ<br>TDFLSVFFSGYTFKHKMVYEDTLTLFPFSGETVFMSMENPGLW<br>ILGCHNSDFRNRGMTALLKVSSCDKNTGDYYEDSYEDISAYLL<br>SKNNAIEPRSFSQNSRHPSTRQKQFNATTIPENDIEKTDPWFA<br>HRTPMPKIQNVSSSDLLMLLRQSPTPHGLSLSDLQEAKYETFS<br>DDPSPGAIDSNNSLSEMTHFRPQLHHSGDMVFTPESGLQLRLN<br>EKLGTTAATELKKLDFKVSSTSNNLISTIPSDNLAAGTDNTSS<br>LGPPSMPVHYDSQLDTTLFGKKSSPLTESGGPLSLSEENNDSK<br>LLESGLMNSQESSWGKNVSSTESGRLFKGKRAHGPALLTKDNA<br>LFKVSISLLKTNKTSNNSATNRKTHIDGPSLLIENSPSVWQNI<br>LESDTEFKKVTPLIHDRMLMDKNATALRLNHMSNKTTSSKNME<br>MVQQKKEGPIPPDAQNPDMSFFKMLFLPESARWIQRTHGKNSL<br>NSGQGPSPKQLVSLGPEKSVEGQNFLSEKNKVVVGKGEFTKDV<br>GLKEMVFPSSRNLFLTNLDNLHENNTHNQEKKIQEEIEKKETL<br>IQENVVLPQIHTVTGTKNFMKNLFLLSTRQNVEGSYDGAYAPV<br>LQDFRSLNDSTNRTKKHTAHFSKKGEEENLEGLGNQTKQIVEK<br>YACTTRISPNTSQQNFVTQRSKRALKQFRLPLEETELEKRIIV<br>DDTSTQWSKNMKHLTPSTLTQIDYNEKEKGAITQSPLSDCLTR<br>SHSIPQANRSPLPIAKVSSFPSIRPIYLTRVLFQDNSSHLPAA |

TABLE 1-continued

| SEQ ID NO | Description | Sequence |
|---|---|---|
| | | SYRKKDSGVQESSHFLQGAKKNNLSLAILTLEMTGDQREVGSL
GTSATNSVTYKKVENTVLPKPDLPKTSGKVELLPKVHIYQKDL
FPTETSNGSPGHLDLVEGSLLQGTEGAIKWNEANRPGKVPFLR
VATESSAKTPSKLLDPLAWDNHYGTQIPKEEWKSQEKSPEKTA
FKKKDTILSLNACESNHAIAAINEGQNKPEIEVTWAKQGRTER
LCSQNPPVLKRHQREITRTTLQSDQEEIDYDDTISVEMKKEDF
DIYDEDENQSPRSFQKKTRHYFIAAVERLWDYGMSSSPHVLRN
RAQSGSVPQFKKVVFQEFTDGSFTQPLYRGELNEHLGLLGPYI
RAEVEDNIMVTFRNQASRPYSFYSSLISYEEDQRQGAEPRKNF
VKPNETKTYFWKVQHFIMAPTKDEFDCKAWAYFSDVDLEKDVH
SGLIGPLLVCHTNTLNPAHGRQVTVQEFALFFTIFDETKSWYF
TENMERNCRAPCNIQMEDPTFKENYRFHAINGYIMDTLPGLVM
AQDQRIRWYLLSMGSNENIHSIHFSGHVFTVRKKEEYKMALYN
LYPGVFETVEMLPSKAGIWRVECLIGEHLHAGMSTLFLVYSNK
CQTPLGMASGHIRDFQITASGQYGQWAPKLARLHYSGSINAWS
TKEPFSWIKVDLLAPMIIHGIKTQGARQKFSSLYISQFIIIVI
YSLDGKKWQTYRGNSTGTLMVFFGNVDSSGIKHNIFNPPIIAR
YIRLHPTHYSIRSTLRMELMGCDLNSCSMPLGMESKAISDAQI
TASSYFTNMFATWSPSKARLHLQGRSNAWRPQVNNPKEWLQVD
FQKTMKVTGVTTQGVKSLLTSMYVKEFLISSSQDGHQWTLFFQ
NGKVKVFQGNQDSFTPVVNSLDPPLLTRYLRIHPQSWVHQIAL
RMEVLGCEAQDLY |
| 5 | FVIII amino acid sequence comprising XTEN (XTEN in bold and underline) | MQIELSTCFFLCLLRFCFSATRRYYLGAVELSWDYMQSDLGEL
PVDARFPPRVPKSPFPNTSVVYKKTLFVEFTDHLFNIAKPRPP
WMGLLGPTIQAEVYDTVVITLKNMASHPVSLHAVGVSYWKASE
GAsequenceEYDDQTSQREKEDDKVFPGGSHTYVWQVLKENG
PMASDPLCLTYSYLSHVDLVKDLNSGLIGALLVCREGSLAKEK
TQTLHKFILLFAVFDEGKSWHSETKNSLMQDRDAASARAWPKM
HTVNGYVNRSLPGLIGCHRKSVYWHVIGMGTTPEVHSIFLEGH
TFLVRNHRQASLEISPITFLTAQTLLMDLGQFLLFCHISSHQH
DGMEAYVKVDSCPEEPQLRMKNNEEAEDYDDDLTDSEMDVVRF
DDDNSPSFIQIRSVAKKHPKTWVHYIAAEEEDWDYAPLVLAPD
DRSYKSQYLNNGPQRIGRKYKKVRFMAYTDETFKTREAIQHES
GILGPLLYGEVGDTLLIIFKNQASRPYNIYPHGITDVRPLYSR
RLPKGVKHLKDFPILPGEIFKYKWTVTVEDGPTKSDPRCLTRY
YSSFVNMERDLASGLIGPLLICYKESVDQRGNQIMSDKRNVIL
FSVFDENRSWYLTENIQRFLPNPAGVQLEDPEFQASNIMHSIN
GYVFDSLQLSVCLHEVAYWYILSIGAQTDFLSVFFSGYTFKHK
MVYEDTLTLFPFSGETVFMSMENPGLWILGCHNSDFRNRGMTA
LLKVSSCDKNTGDYYEDSYEDISAYLLSKNNAIEPRSFSQN**TS
ESATPESGPGSEPATSGSETPGTSESATPESGPGSEPATSGSE
TPGTSESATPESGPGTSTEPSEGSAPGSPAGSPTSTEEGTSES
ATPESGPGSEPATSGSETPGTSESATPESGPGSPAGSPTSTEE
GSPAGSPTSTEEGASS**PPVLKRHQREITRTTLQSDQEEIDYDD
TISVEMKKEDFDIYDEDENQSPRSFQKKTRHYFIAAVERLWDY
GMSSSPHVLRNRAQSGSVPQFKKVVFQEFTDGSFTQPLYRGEL
NEHLGLLGPYIRAEVEDNIMVTFRNQASRPYSFYSSLISYEED
QRQGAEPRKNFVKPNETKTYFWKVQHFIMAPTKDEFDCKAWAY
FSDVDLEKDVHSGLIGPLLVCHTNTLNPAHGRQVTVQEFALFF
TIFDETKSWYFTENMERNCRAPCNIQMEDPTFKENYRFHAING
YIMDTLPGLVMAQDQRIRWYLLSMGSNENIHSIHFSGHVFTVR
KKEEYKMALYNLYPGVFETVEMLPSKAGIWRVECLIGEHLHAG
MSTLFLVYSNKCQTPLGMASGHIRDFQITASGQYGQWAPKLAR
LHYSGSINAWSTKEPFSWIKVDLLAPMIIHGIKTQGARQKFSS
LYISQFIIIVIYSLDGKKWQTYRGNSTGTLMVFFGNVDSSGIK
HNIFNPPIIARYIRLHPTHYSIRSTLRMELMGCDLNSCSMPLG
MESKAISDAQITASSYFTNMFATWSPSKARLHLQGRSNAWRPQ
VNNPKEWLQVDFQKTMKVTGVTTQGVKSLLTSMYVKEFLISSS
QDGHQWTLFFQNGKVKVFQGNQDSFTPVVNSLDPPLLTRYLRI
HPQSWVHQIALRMEVLGCEAQDLY |
| 6 | FIX-R338L amino acid sequence (signal peptide in bold and underline) | **MQRVNMIMAESPGLITICLLGYLLSAECTVFLDHENANKILNR
PKR**YNSGKLEEFVQGNLERECMEEKCSFEEAREVFENTERTTE
FWKQYVDGDQCESNPCLNGGSCKDDINSYECWCPFGFEGKNCE
LDVTCNIKNGRCEQFCKNSADNKVVCSCTEGYRLAENQKSCEP
AVPFPCGRVSVSQTSKLTRAETVFPDVDYVNSTEAETILDNIT
QSTQSFNDFTRVVGGEDAKPGQFPWQVVLNGKVDAFCGGSIVN
EKWIVTAAHCVETGVKITVVAGEHNIEETEHTEQKRNVIRIIP
HHNYNAAINKYNHDIALLELDEPLVLNSYVTPICIADKEYTNI
FLKFGSGYVSGWGRVFHKGRSALVLQYLRVPLVDRATCLLSTK
FTIYNNMFCAGFHEGGRDSCQGDSGGPHVTEVEGTSFLTGIIS
WGEECAMKGKYGIYTKVSRYVNWIKEKTKLT |

D. Excipients, Carriers, and Other Constituents of Formulations

In certain embodiments, viral vector compositions produced by a process or method provided herein are combined with one or more pharmaceutical excipients to make a pharmaceutical composition comprising the viral vector.

In certain embodiments, the pharmaceutical composition comprises an effective dose of a viral vector (e.g., a recombinant lentiviral vector). In certain embodiments, the pharmaceutical composition comprises an effective dose of a recombinant lentiviral vector. In certain embodiments, the pharmaceutical composition comprises a formulation buffer. In certain embodiments, the formulation buffer is a phosphate or histidine buffer comprising NaCl and sucrose. In certain embodiments, the pharmaceutical composition comprises: (a) an effective dose of a recombinant lentiviral vector; (b) a TRIS-free buffer system; (c) a salt; (d) a surfactant; and (e) a carbohydrate, wherein the pharmaceutical composition is suitable for administration to a human subject. In certain embodiments, the pH of the buffer system is between 6.0 and 8.0. In certain embodiments, the buffer system is a phosphate buffer or a histidine buffer. In certain embodiments, the concentration of the phosphate or histidine buffer is between 5 mM and 30 mM. In certain embodiments, the concentration of the phosphate buffer is about 10 to about 20 mM, about 10 to about 15 mM, about 20 to about 30 mM, about 20 to about 25 mM, or about 15 to about 20 mM. In certain embodiments, the salt is a chloride salt. In certain embodiments, the concentration of the chloride salt is between 80 mM and 150 mM. In certain embodiments, the concentration of the salt is about 100 mM, about 110 mM, about 130 mM, or about 150 mM. In certain embodiments, the surfactant is a poloxamer or a polysorbate. In certain embodiments, the concentration of the poloxamer or polysorbate is between 0.01% and 0.1%. In certain embodiments, the carbohydrate is sucrose. In certain embodiments, the concentration of the carbohydrate is between 0.5% and 5%. In certain embodiments, the chloride salt is NaCl. In certain embodiments, the poloxamer is selected from the group consisting of poloxamer 101 (P101), poloxamer 105 (P105), poloxamer 108 (P108), poloxamer 122 (P122), poloxamer 123 (P123), poloxamer 124 (P124), poloxamer 181 (P181), poloxamer 182 (P182), poloxamer 183 (P183), poloxamer 184 (P184), poloxamer 185 (P185), poloxamer 188 (P188), poloxamer 212 (P212), poloxamer 215 (P215), poloxamer 217 (P217), poloxamer 231 (P231), poloxamer 234 (P234), poloxamer 235 (P235), poloxamer 237 (P237), poloxamer 238 (P238), poloxamer 282 (P282), poloxamer 284 (P284), poloxamer 288 (P288), poloxamer 331 (P331), poloxamer 333 (P333), poloxamer 334 (P334), poloxamer 335 (P335), poloxamer 338 (P338), poloxamer 401 (P401), poloxamer 402 (P402), poloxamer 403 (P403), poloxamer 407 (P407), and a combination thereof. In certain embodiments, the polysorbate is selected from the group consisting of polysorbate 20, polysorbate 40, polysorbate 60, polysorbate 80, and a combination thereof. In certain embodiments, the pH of the phosphate or histidine buffer is 6.1, 6.3, 6.5, 6.7, 6.9, 7.1, 7.3, 7.5, 7.7, or 7.9. In certain embodiments, the concentration of the phosphate or histidine buffer is 10 mM, 15 mM, 20 mM, or 25 mM. In certain embodiments, the chloride salt is 100 mM, 110 mM, 130 mM, or 150 mM. In certain embodiments, the concentration of the poloxamer or polysorbate is 0.03%, 0.05%, 0.07%, or 0.09%. In certain embodiments, the concentration of the carbohydrate is 1%, 2%, 3%, or 4%. In certain embodiments, the poloxamer is poloxamer 188 (P188). In certain embodiments, the poloxamer is poloxamer 407 (P407).

The viral vector of the disclosure can be administered intravenously, subcutaneously, intramuscularly, or via any mucosal surface, e.g., orally, sublingually, buccally, sublingually, nasally, rectally, vaginally or via pulmonary route. The viral vector can be implanted within or linked to a biopolymer solid support that allows for the slow release of the vector to the desired site.

In one embodiment, the route of administration of the formulated drug substance comprising a viral vector is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the disclosure, a form for administration would be a solution for injection, in particular for intravenous or intraarterial injection or drip. Usually, a suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, the viral vector can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject disclosure, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present disclosure, for the treatment of conditions vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

A pharmaceutical composition comprising a viral vector can be administered as a single dose or as multiple doses, wherein the multiple doses can be administered continuously or at specific timed intervals. In vitro assays can be employed to determine optimal dose ranges and/or schedules for administration. In vitro assays that measure clotting factor activity are known in the art. Additionally, effective doses can be extrapolated from dose-response curves obtained from animal models, e.g., a hemophiliac dog (Mount et al. 2002, Blood 99 (8): 2670).

Doses intermediate in the above ranges are also intended to be within the scope of the disclosure. Subjects can be administered such doses daily, on alternative days, weekly or according to any other schedule determined by empirical analysis. An exemplary treatment entails administration in multiple dosages over a prolonged period, for example, of at least six months.

A pharmaceutical composition comprising a viral vector can be administered on multiple occasions. Intervals between single dosages can be daily, weekly, monthly or yearly. Intervals can also be irregular as indicated by measuring blood levels of modified polypeptide or antigen in the patient. Dosage and frequency of a viral vector may vary depending on the half-life of the transgene protein product in the patient.

The dosage and frequency of administration of a pharmaceutical composition comprising a viral vector can vary depending on whether the treatment is prophylactic or therapeutic. In prophylactic applications, compositions containing a viral vector are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

A pharmaceutical composition comprising a viral vector can optionally be administered in combination with other agents that are effective in treating the disorder or condition in need of treatment (e.g., prophylactic or therapeutic).

As used herein, the administration of a pharmaceutical composition comprising a viral vector in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen can be timed to enhance the overall effectiveness of the treatment. A skilled artisan (e.g., a physician) would be readily be able to discern effective combined therapeutic regimens without undue experimentation based on the selected adjunct therapy and the teachings of the instant specification.

It will further be appreciated that a pharmaceutical composition comprising a viral vector can be used in conjunction or combination with an agent or agents (e.g., to provide a combined therapeutic regimen). Exemplary agents with which a pharmaceutical composition comprising a viral vector can be combined include agents that represent the current standard of care for a particular disorder being treated. Such agents can be chemical or biologic in nature. The term "biologic" or "biologic agent" refers to any pharmaceutically active agent made from living organisms and/or their products which is intended for use as a therapeutic.

The amount of agent to be used in combination with a pharmaceutical composition comprising a viral vector can vary by subject or can be administered according to what is known in the art. See, e.g., Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., $9^{th}$ ed. 1996). In another embodiment, an amount of such an agent consistent with the standard of care is administered.

In certain embodiments, a pharmaceutical composition comprising a viral vector is administered in conjunction with an immunosuppressive, anti-allergic, or anti-inflammatory agent. These agents generally refer to substances that act to suppress or mask the immune system of the subject being treated herein. These agents include substances that suppress cytokine production, downregulate or suppress self-antigen expression, or mask the MHC antigens. Examples of such agents include 2-amino-6-aryl-5-substituted pyrimidines; azathioprine; cyclophosphamide; bromocryptine; danazol; dapsone; glutaraldehyde; anti-idiotypic antibodies for MHC antigens and MHC fragments; cyclosporin A; steroids such as glucocorticosteroids, e.g., prednisone, methylprednisolone, and dexamethasone; cytokine or cytokine receptor antagonists including anti-interferon-γ, -β, or -α antibodies, anti-tumor necrosis factor-α antibodies, anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; pan-T antibodies; soluble peptide containing a LFA-3 binding domain;

streptokinase; TGF-β; streptodornase; FK506; RS-61443; deoxyspergualin; and rapamycin. In certain embodiments, the agent is an antihistamine. An "antihistamine" as used herein is an agent that antagonizes the physiological effect of histamine. Examples of antihistamines are chlorpheniramine, diphenhydramine, promethazine, cromolyn sodium, astemizole, azatadine maleate, bropheniramine maleate, carbinoxamine maleate, cetirizine hydrochloride, clemastine fumarate, cyproheptadine hydrochloride, dexbrompheniramine maleate, dexchlorpheniramine maleate, dimenhydrinate, diphenhydramine hydrochloride, doxylamine succinate, fexofendadine hydrochloride, terphenadine hydrochloride, hydroxyzine hydrochloride, loratidine, meclizine hydrochloride, tripelannamine citrate, tripelennamine hydrochloride, and triprolidine hydrochloride.

Immunosuppressive, anti-allergic, or anti-inflammatory agents may be incorporated into the pharmaceutical composition comprising a viral vector administration regimen. For example, administration of immunosuppressive or anti-inflammatory agents may commence prior to administration of a pharmaceutical composition comprising a viral vector, and may continue with one or more doses thereafter. In certain embodiments, the immunosuppressive or anti-inflammatory agents are administered as premedication to the pharmaceutical composition comprising a viral vector.

It will be appreciated that a pharmaceutical composition comprising a viral vector can be formulated to facilitate administration and promote stability of the active agent. Preferably, pharmaceutical compositions in accordance with the present disclosure comprise a pharmaceutically acceptable, non-toxic, sterile carrier such as physiological saline, non-toxic buffers, preservatives and the like. Of course, the pharmaceutical compositions of the present disclosure can be administered in single or multiple doses to provide for a pharmaceutically effective amount of the polypeptide.

Having now described the present disclosure in detail, the same will be more clearly understood by reference to the following examples, which are included herewith for purposes of illustration only and are not intended to be limiting of the disclosure. All patents, publications, and articles referred to herein are expressly and specifically incorporated herein by reference.

EXAMPLES

Materials and Methods

The following are exemplary reagents (Table 2) and general methods provided that are suitable for carrying out methods of the present disclosure, as outlined in Examples 1-6.

TABLE 2

Exemplary reagents suitable for use in methods described herein.

| Description of Material | Vendor | Cat. No. |
|---|---|---|
| HEK293 cells | In-house | N/A |
| Plasmids (Genomic FVIIIXTEN, FVIII, FIX; Gagpol; VSV-G; Rev) Transfection agent: | In-house | N/A |
| PEIpro | Polyplus Transfection | 115-400 |
| Lipofactamine 2000 | Thermo-Fisher Scientific | 11668019 |
| Lipofactamine 3000 | Thermo-Fisher Scientific | L300075 |
| VIIISelect resin | Cytiva | Cat No. 17-5450 |
| FreeStyle 293 Expression Production Media | Thermo-Fisher Scientific | 12338-002 |
| 250 X Cholesterol Lipid Concentrate (CLC) | Thermo Scientific | 12351-018 |
| BIOSTAT ® STR50 FlexSafe ® Bag | Sartorius Stedim | FRS131920 D |
| Benzonase ® endonuclease | Merck Millipore | 1.01697.001 |
| Anion Exchange Chromatography media (Sartobind ® Q) | Sartorius Stedim | 96IEXQ42D1GSS |
| AKTA Avant 150 Chromatography | GE Healthcare | |
| HDC ® II pre-filter part number | Pall Corporation | NP7J100P1G |
| Supor ® EAV 0.2 μm filter | Pall Corporation | NT7UEAVP1S |
| Hollow Fiber membrane, 500 kDa | Cytiva | ReadyToProcess ™ RTPUFP-500-C-6S |
| Chromogenix Coatest ® SP Factor VIII Kit | Diapharma | K824086 |
| CaCl2 | Millipore-Sigma | 449709-10G |
| Sodium phosphate | VWR | JT3802-1 and JT3827-1 |
| Tromethane or Tris | Avantor, Millipore | T6066, T5941 |
| Sodium Chloride | J T Baker | BAKR3627 |
| Capto MMC | Cytiva | 17531710, 17371601 |
| Capto Adhere | Cytiva | 17544410, 17371501 |
| CIMmultus Advanced composite Monolith columns | Bia Separations | 411.5114-2, 411.5113-2, |

FVIIIXTEN or FVIII Activity Determination: The chromogenic assay kit Chromogenix Coatest® SP Factor VIII (Cat No. K824086; Diapharma™) can be used for the in vitro diagnostic photometric determination of FVIII activity. Briefly, Factor X is activated to Factor Xa by Factor IXa in the presence of calcium and phospholipids. This generation is greatly stimulated by FVIII. Optimal amounts of Ca$^{2+}$ and phospholipids and an excess of Factors IXa and X was used, making the rate of activation of Factor X dependent on the amount of FVIII. Factor Xa hydrolyses the chromogenic substrate (Z-D-Arg-Gly-Arg-pNA) S-2765™, thus liberating the chromophoric group, pNA (p-nitroaniline). The generated Factor Xa and resulting intensity of color is proportional to the FVIII activity in the sample. The color can then be read photometrically at 405 nm.

Production of Viral Vector: Enveloped viral vectors LV-FVIIIXTEN or LV-FVIII were produced in human embryonic kidney 293 (HEK293) cells. The cells are adapted to culture media and either: (1) transfected transiently using plasmid DNA and transfection agent such as PEIpro® (Cat. No. 115-400, Polyplus Transfection®), Lipofactamine® 2000 (Cat. No. 11668019, Thermo Fisher™), Lipofactamine® 3000 (Cat. No. L300075, Thermo Fisher™) or other equivalent reagents, or (2) stable producer cells are induced in shake flasks or bioreactors (disposable systems, conventional stirred tanks with or without adsorption media in the vessel) and run as batch, fed-batch, perfusion or continuous chemostate culture to produce viral particles. The vector producing cells can be cultured in production media such as FreeStyle™ 293 Expression medium, LV-Max™ or equivalent media, generally, serum free and chemically defined. Typically, suspension culture involves perfusion of medium, exchange of media using alternating tangential flow (ATF) or addition of fresh media using sequential addition of nutrients, and is performed to increase cell numbers and product titer beyond the batch culture systems. The product yield, product purity and amount of impurities depends on the ability of the cells to produce vectors, the system of production used, or a combination thereof. The viral vector produced from cells remains in culture supernatant along with other process- and product-related impurities and proteins generated during the process.

Cell Separation and Nucleic Acid Treatment: Vector producing cells, cell debris and other particulate impurities can be separated from supernatant using a filtration step. Suitable filters include those comprising two or more filters in sequence, and may utilize regenerated cellulose fibers, cellulose fibers combined with inorganic filter aids or organic resins, or any combination thereof, and polymeric filters. For example, nylon, polypropylene (PE), polyethersulfone (PES) filters can be used to achieve effective removal of cell debris and other particulate impurities, and result in acceptable recoveries. A multiple stage process can be used to improve vector yield and impurity reduction. An exemplary two or three-stage process would consist of a coarse filter(s) to remove cells, large precipitate and cell debris followed by a polishing second stage filter(s) with nominal pore sizes of 0.65, 0.45, 0.22, or 0.2 micron. The optimal combination may be a function of the depth filter size grading, cell holding capacity and interaction of filter contact surface with viral vector and impurities. Alternatively, a staged operation may be performed for clarification, and may include single stage operations employing a centrifugation followed by a polishing stage filter(s) with nominal pore sizes of 0.65, 0.45, 0.22, or 0.2 micron. Generally, a clarification approach includes a combination of one or more of the following, without limitation, dead-end filtration, microfiltration, centrifugation, and depth filtration, providing a supernatant of suitable clarity or turbidity and absent of particulate matters that are suitable for subsequent purification steps. For example, two stage depth filtration including 5-10 micron and 1.2-2.0 micron depth filtration followed by a membrane filtration of 0.2-0.65 um can be used in combination.

The supernatant contains nucleic acids (DNA/RNA) impurities generated by host cells or a product of the transient transfection process. Such nucleic acids can be degraded by using suitable nucleases, for example Benzonase® Endonuclease (Cat. No. 1.01697.001, Millipore Sigma™) or any other DNase and/or RNase commonly used within the art for the purpose of eliminating unwanted or contaminating DNA and/or RNA. Such nucleases function by attacking and degrading all forms of DNA and RNA (single stranded, double stranded linear or circular) for the preparation of supernatant before or after the cell separation operations are performed. In some embodiments, the concentration of nucleases used is within the range of 1-100 Units/mL, added before or after cell separation unit operation and allowed to incubate with supernatant culture for 5-60 min at 20-37° C., or potentially over night at 2-8° C., for digestion of nucleic acids to an acceptable level. Alternatively, in absence of such addition of nucleases, non-vector producing cells responsible for nuclease enzyme secretion can be added, or selective precipitation can be performed using suitable precipitating agents for the removal of DNA/RNA impurities.

Purification of Viral Vector: The purification of viral vector involves separating functional vector from supernatant comprising viral vector product as well as other protein- and non-protein-related impurities, including the transgene protein contaminants mediated by the promoter upstream of the transgene expression cassette (e.g., CMV promoter). The supernatant undergoes stages of purifications, for example, potentially multiple stages of chromatography, TFF and microfiltration processes, as outlined in FIGS. 1A and 1B. Subsequent purification is performed to achieve the drug substance.

In some embodiments, two or more sequential chromatography steps may be useful to achieve higher viral vector particle purity and assure removal of contaminating proteins, nucleic acids, endotoxins, and other product-related variants. High viral vector particle purity is a requirement for the manufacture of enveloped viral vector for use in human subjects to treat diseases. Sequential chromatography steps can use different resins performed sequentially in varying orders, optimized for higher recovery of functional viral vector and minimizing impurities in the final drug product. For example, vector particle purification achieved by two sequential chromatography steps, as shown in FIG. 1B, may employ Viral Vector Capture Chromatography (First Chromatography Purification) followed by a transgene protein encoded by the Transgene Impurity Capture Chromatography (Second Chromatography Purification). The viral vector capture chromatography step and the transgene impurity capture chromatography step can be performed in any order, e.g., in reverse order to what is shown in FIG. 1B where the transgene impurity capture chromatography step is performed first, followed by the viral vector capture chromatography step.

In certain embodiments, the supernatant is applied to a first anion exchange column. In certain embodiments, the anion exchange column comprises a combination of membrane and DEAE or Q chemistry. A number of suitable anion exchangers for use with the present invention includes, without limitation, CIM Monolith (Q or DEAE, strong or weak anion-exchanger, BIA Separations), Sartobind Q (Q or DEAE, strong or weak anion exchanger, Sartorius Stedim), TOYOPEARLE 650C (DEAE, UNOSPHERE Q or DEAE, strong or weak anion-exchanger, BioRad, Hercules); POROS 50 (HQ, strong-anion-exchanger, Life Technologies), POROS 50 (XS, strong-anion-exchanger, Life Technologies), POROS 50 (D, weak anion-exchanger, Life Technologies), POROS 50 (PI, weak anion-exchanger, Life Technologies), SEPHAROSE (DEAE, weak anion-exchanger, Cytiva); SEPHAROSE (Q, Strong anion-exchanger, Cytiva), and Capto Q (Srong anion-exchanger, Cytiva).

The anion exchange column is first equilibrated using standard buffers and according to the manufacturer's specifications or buffers well known to those of skill in the art. Such buffers may comprise, without limitation, Tris, phosphate, histidine, salt and other excipients at a pH value close to physiological condition. For example, the column can be equilibrated with a buffer comprising 10-50 mM Tris-HCl, 2 mM $MgCl_2$, 150 mM NaCl, pH 7.2, or a buffer comprising 10-50 mM Phosphate, 2 mM $MgCl_2$, 150 mM NaCl, pH 7.2. Sample is then loaded and two elution buffers are applied, one low salt buffer and one high salt buffer. Fractions are collected following each of the low salt and high salt washes and protein is detected in the fractions using standard techniques, such as monitoring UV absorption at 260 and/or 280 nm. Using an anion exchanger, the protein peaks from the higher salt eluate contain viral vector particles, which are diluted using a low salt or no salt containing elution buffer and processed for the next step. Alternatively, the vector containing product fraction is diluted and stored at 2-15° C. prior to the next operation step. Appropriate buffers for use in the viral vector capture chromatography step comprising the use of anion-exchange columns are well known in the art and are generally cationic or zwitterionic in nature. Such buffers include, without limitation, buffers with the following buffer ions: Triethanolamine; Tris; Sodium or Potassium Phosphate; Bis-Tris; Bis-Tris propane; N-methyldiethanolamine, and the like.

In certain embodiments, the eluate of the viral vector chromatography step can be further processed by a transgene impurity capture chromatography step, wherein undesired impurities including transgene protein contaminants encoded by the viral vector are captured. The purified composition comprising the viral vector is received in the flow-through product, wherein the viral vector runs through the chromatography device without specifically binding to a transgene impurity capture chromatography matrix.

The transgene impurity capture chromatography step comprises use of polymers having sufficient matrix crosslinking such that interaction of a transgene protein contaminant takes place, wherein also present are any of a number of binding groups including, for example, those that are affinity, ion-exchange, multimodal, mixed-mode or hydrophobic in nature. The second transgene impurity capture chromatography step involves capture of impurities including transgene protein contaminants mediated by viral vector, and uses one or a combination of affinity (e.g. VIIISelect available from Cytiva), ion-exchange (e.g. Cation-exchange available from multiple vendors), multimodal/mixed-mode (e.g. Capto MMC available from Cytiva) and hydrophobic interaction (e.g. Capto Adhere available from Cytiva) chromatography resins.

In certain embodiments, the resulting sample obtained after a viral vector capture chromatography step is loaded onto a transgene impurity capture chromatography matrix after dilution of the sample to enable appropriate impurity binding and viral vector unbinding condition into the column. For example, the loading sample may comprise, without limitation, 10-50 mM Tris-HCl or 10-50 mM Phosphate, with 2 mM $MgCl_2$, 10 mM to 120 mM $CaCl_2$), pH 6.5 to 7.5 with diluted sample conductivity in the range of 20 to 40 mS/cm. The transgene impurity capture chromatography resin is equilibrated with an equilibration buffer known to those of skill in the art, for example, a buffer comprising, without limitation, 10-50 mM Tris or 10-50 mM Phosphate containing 0 to 2 mM $MgCl_2$, 10-30 mM $CaCl_2$), 10 to 70 mM NaCl, pH 7.2.

Example 1: Transgene Protein Encoded by the Viral Vector

Figure 2:
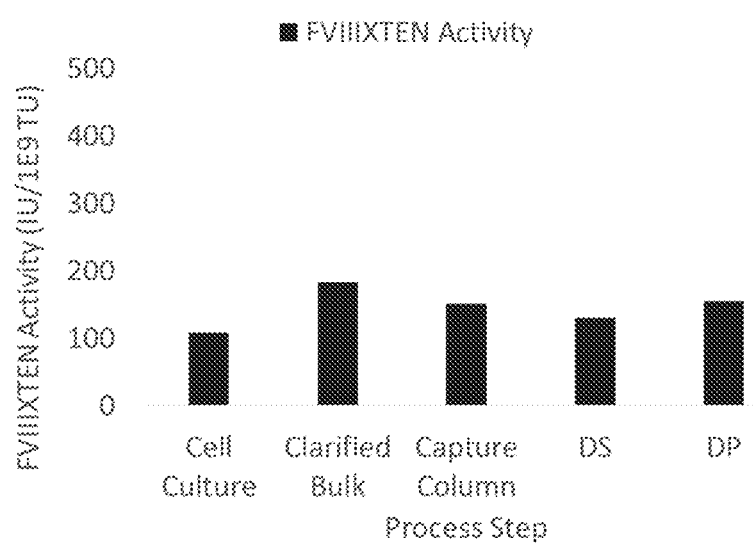
FIG. 2 are plots showing the activity of FVIIIXTEN transgene protein per 1E9 TU of lentiviral vector during each step of the conventional purification process as shown in FIG. 1A. The contaminating FVIIIXTEN protein activity is consistently present during various stages of the production process, including in the final drug substance (DS) and drug product (DP).

LV-FVIIIXTEN/LV-FVIII are lentiviral vectors developed to express FVIIIXTEN/FVIII proteins respectively, in blood after post-administration of viral vector for use in the treatment of Hemophilia A. FVIIIXTEN/FVIII activity was observed during LV-FVIIIXTEN/LV-FVIII viral vector production process, respectively in the bioreactor cell culture, clarified supernatant, after purification chromatography, drug substance and in the purified drug product. Purified enveloped viral vector produced in a bioreactor and purified according to a process as shown in FIG. 1A, was found to contain a significant level of protein impurity in the drug product. Without being bound to any theory, the protein impurity may be present due to the expression of transgene proteins mediated by the CMV promoter upstream of the FVIIIXTEN/FVIII expression cassette. The protein impurity (e.g., transgene protein contaminant) could not be purified efficiently using standard (i.e. conventional) downstream process workflows such as the one shown in FIG. 1A. The activity of transgene protein per 1E9 TU of functional viral vector was found to be consistent across the stages of the purification process, and the final product sample, as shown in FIG. 2. Without being bound to any theory, the purification chromatography column utilized to capture viral vector particles was found to be less effective in separating enveloped viral vector from transgene protein contaminants, likely due to the transgene protein contaminant co-purifying with viral vector product.

Figure 3A:
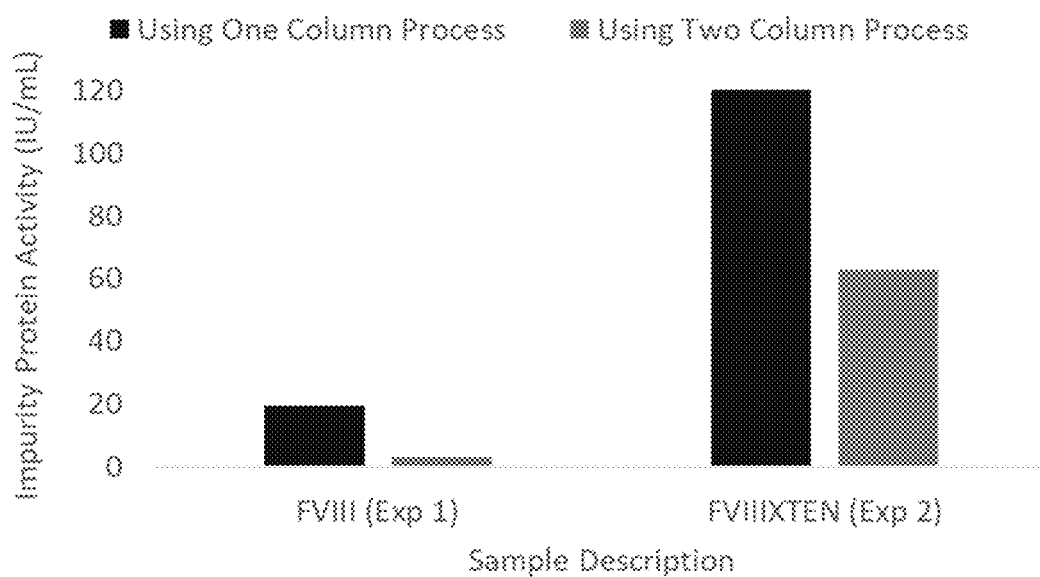
FIGS. 3A-3B are plots showing the evaluation of VIIISelect affinity chromatography for the purification of lentiviral vector from FVIII transgene protein encoded by the viral vector. The experiments were conducted with either FVIII (Exp 1) or FVIIIXTEN (Exp 2) transgene protein.
Figure 3B:
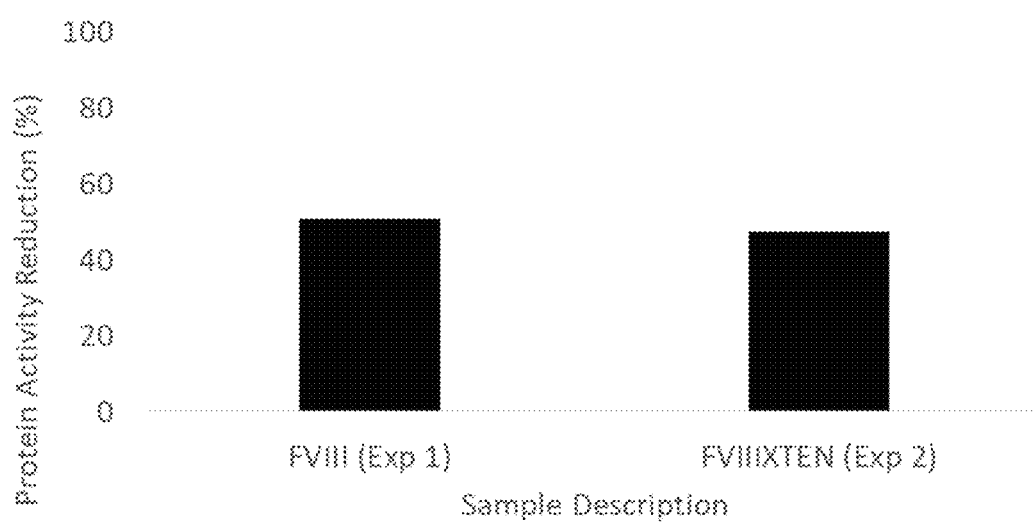

Example 2: Reduction of Contaminating Transgene Protein Product During Purification To reduce contaminating transgene protein product, a second purification chromatography resin or media was investigated for capturing transgene protein encoded by viral vector to improve overall viral vector purification in the downstream process workflow, as shown in FIG. 1B. In FIGS. 3A and 3B, Exp 1 and 2 were performed with the addition of a second purification chromatography column. The column XK16/20 (GE Healthcare, Cat No. 17-5450) was packed with VIIISelect resin (Cat No. 17-5450-01) to a bed height of 11.5 cm with a Column Volume (CV) of 23 mL. The column and VIIISelect resin were purchased from Cytiva, USA. The starting material was produced in suspension culture using a single use stirred tank bioreactor utilizing HEK293 cells (in-house), FreeStyle 293 Expression (Cat. No. 12338-002, Thermo Fisher Scientific) production media, plasmids (in-house) and PEIpro transfection agent (Cat. No. 115-400, Polyplus Transfection) using a quad transfection process.

The second purification chromatography resin captured specific transgene protein contaminants and allowed viral vector to flow through the chromatography column without viral particles being specifically bound to the column. The one-column process was compared to the two-column process involving VIIISelect affinity resin as second chromatography resin to capture transgene protein contaminant, and it was found that the two-column process enabled lower level of FVIIIXTEN or FVIII protein contaminant in the drug product. The level of transgene protein contaminant was reduced from 20 IU/mL to 3 IU/mL in the LV-FVIII sample (Exp 1) and from 129 IU/mL to 63 IU/mL in the LV-FVIIIXTEN sample (Exp 2) (FIG. 3A). This equates to a total reduction of about 51% and 48% in transgene protein contaminant level in the LV-FVIII and LV-FVIIIXTEN viral vector samples, respectively (FIG. 3B). In FIGS. 3A and 3B, the LV-FVIII and LV-FVIIIXTEN samples for loading into VIIISelect affinity resin were formulated in 10 mM sodium phosphate, 100 mM NaCl, 3% sucrose (w/v), and 0.05% Poloxamer (w/v), pH 7.2.

Example 3: Enhanced Reduction of Contaminating Transgene Protein During Purification To improve transgene impurity capture in the two-column purification work flow, addition of $CaCl_2$) was investigated for potential improvement in viral vector purification. 10 mM of $CaCl_2$) was either added in the viral vector sample before capture chromatography (+CaCl2) or not added (−CaCl2)), and the load sample was incubated for 10 minutes prior to subjecting the sample to the purification column using VIIISelect affinity chromatography media. In the second chromatography purification step, affinity chromatography was performed using 450 uL of VIIISelect resin in a column. The column was equilibrated with 10 volumes of resin with formulation buffer containing histidine for FVIII (Exp 3) or phosphate for FVIIIXTEN (Exp 4) for separation. In an experiment, the viral vector sample was mixed with 500 ul of resulting sample and 10 mM $CaCl_2$ (+CaCl2) or without $CaCl_2$) (−CaCl2)) and loaded into the column. The formulation buffer was loaded to recover vector product in flow-through after a 10 minute contact time.

Figure 4:
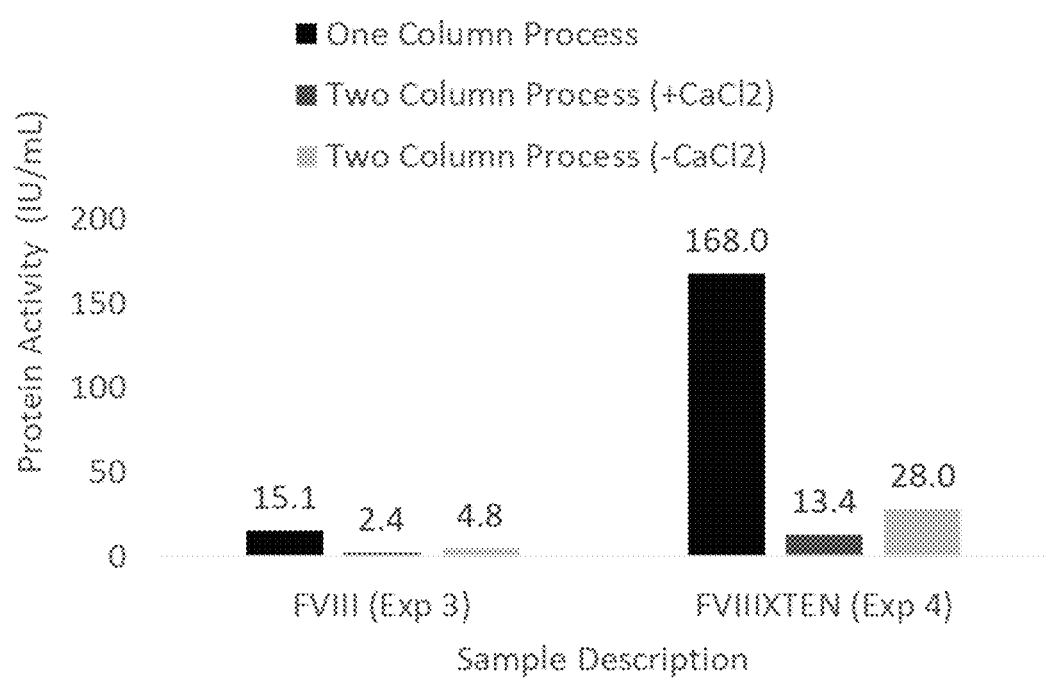
FIG. 4 is a plot showing the results of using a calcium chloride in a Two Column Process of the invention. VIIISelect affinity chromatography was employed to capture FVIII transgene protein in the presence ("+CaCl2") or absence of CaCl$_2$) ("−CaCl2"). Lentiviral vector encoding FVIIIX-TEN (LV-FVIIIXTEN) was purified in phosphate buffer (Exp 3), whereas lentiviral vector encoding FVIII (LV-FVIII) was purified in histidine buffer (Exp 4).

Remaining FVIIIXTEN or FVIII activity in the flow-through sample was measured by chromogenic assay (See above materials and methods). FIG. 4 shows the remaining FVIIIXTEN or FVIII activity in the flow-through in formulation buffer containing histidine, where the viral vector sample was mixed with LV-FVIII or flow-through in formulation buffer containing phosphate, where the viral vector was LV-FVIIIXTEN.

As shown in FIG. 4, bars labeled "One Column Process" indicate downstream workflow involving one dedicated vector purification chromatography step, whereas bars labelled "Two Column Process" indicates downstream workflow involving two dedicated vector purification chromatography steps. In Exp 3, FVIII protein activity was reduced from 15.1 IU/mL to 2.4 IU/mL in the +CaCL2 condition, and was reduced to 4.8 IU/mL in the −CaCl2 condition. In Exp 4, FVIIIXTEN protein activity was reduced from 168.0 IU/mL to 13.4 IU/mL in the +CaCl2 condition, and reduced to 28.0 IU/mL in the −CaCl2 condition. As shown in FIG. 4, the presence of $CaCl_2$) in the pre-column samples provides improvement in viral vector purification.

Figure 5:
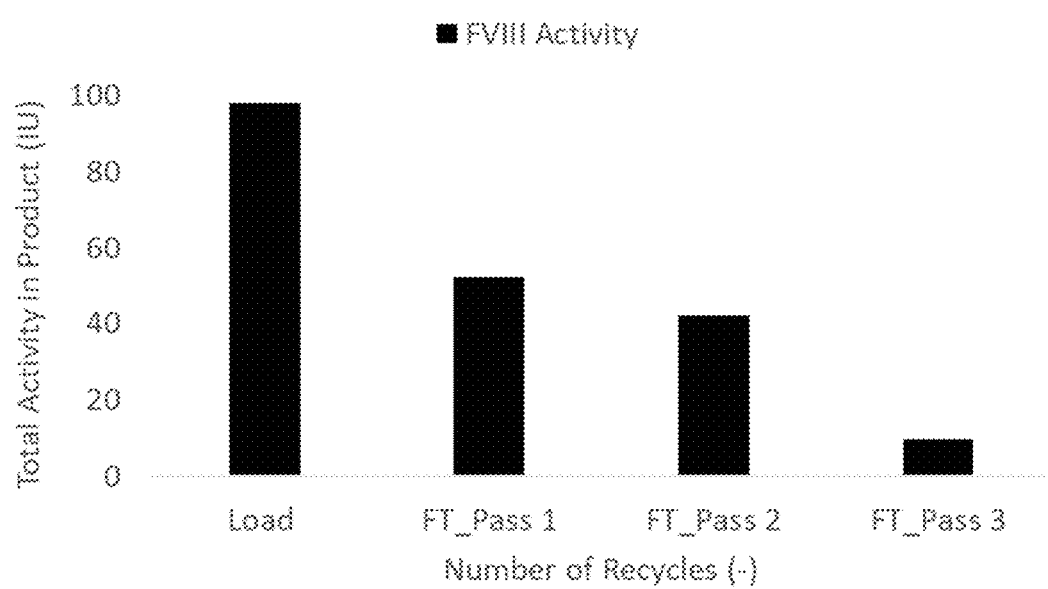
FIG. 5 is a plot showing the total FVIII activity remaining in a lentiviral vector preparation encoding FVIII (LV-FVIII) after conducting multiple transgene protein capture steps. The viral sample was recycled by passing it through a VIIISelect affinity chromatography resin multiple times to capture transgene protein encoded by the viral vector. Each transgene protein capture step was performed in the presence of $CaCl_2$). The viral vector LV-FVIII was purified in histidine buffer.

Example 4: Enhanced Reduction of Contaminating Transgene Protein Using Recycling Mode Transgene protein contaminant reduction was investigated for further reduction using recycle mode technique, where the sample containing the transgene protein contaminant was passed through transgene impurity capture purification chromatography column multiple times. The load sample comprising LV-FVIII viral vector and FVIII protein impurity present in histidine buffer (i.e. Load) was spiked with 10 mM $CaCl_2$) (+CaCl2), incubated for 10 min, and passed through an VIIISelect affinity chromatography column. The prepared load sample was run through the column at 6 min Residence Time (RT) and the flow-through of the column called "FT_Pass 1" was collected and analyzed for impurity activity or concentration. Then, the "FT_Pass 1" was adjusted to 10 mM $CaCl_2$) concentration, incubated for 10 min and loaded again into the same column without the column being cleaned or regenerated. The flow through of the second pass is called "FT_Pass 2." Similarly, the FT_Pass 2 load sample was passed a third time through the column after adjustment of $CaCl_2$) concentration and incubation time in a manner similar to previous passes. The third pass flow through was collected as "FT_Pass 3." The load, FT_Pass 1, FT_Pass 2 and FT_Pass 3 samples were used to determine the content of impurity activity. As shown in FIG. 5, the total activity amount present in the sample to be purified by the transgene impurity capture chromatography was found to be 98 IU. This activity was reduced to 52 IU (FT_Pass 1), 42 IU (FT_Pass 2) and 10 IU (FT_Pass 3), after the multiple cycles. The overall reduction in amount of contaminating FVIII protein activity was found to be 90% after three cycles.

Example 5: Reduction of Contaminating Transgene Protein During Purification Using Tris Buffer System without Excipients The purification of vector was investigated for further removal of contaminating transgene protein using a second chromatography purification step in an improved downstream workflow scheme (e.g., as shown in FIG. 1B, FIG. 6A and FIG. 6B). In the improved scheme, the vector product is subjected to a chromatography media specifically designed for removal of contaminating transgene protein impurity. The step of removal of contaminating transgene protein impurity may be the second chromatography purification step (as shown in FIG. 6A), or it may be the first chromatography step (as shown in FIG. 6B), in an improved downstream workflow scheme of the invention.

FIG. 7 shows the impact of the concentration of salt in the loading sample on the effectiveness of purification of a second chromatography purification, wherein the second chromatography purification comprises the use of VIIISelect resin. In this experiment, a first chromatography purification using an anion exchange (AEX) column was performed, and the vector product was eluted from the AEX column with a buffer containing 400 mM NaCl. The AEX eluate (i.e., load sample for the second chromatography purification comprising VIIISelect resin) was then adjusted to have a salt concentration of either 400 mM NaCl (Exp5), or 100 mM NaCl (Exp6). In Exp5, the adjusted load sample contained 400 mM NaCl, 2.5 mM $CaCl_2$), and 2.0 mM $MgCl_2$ in Tris-HCl buffer, pH 7.2. In Exp6, the load sample contained 100 mM NaCl, 2.5 mM $CaCl_2$), and 2.0 mM $MgCl_2$ in Tris-HCl buffer, pH 7.2.

Figure 7A:
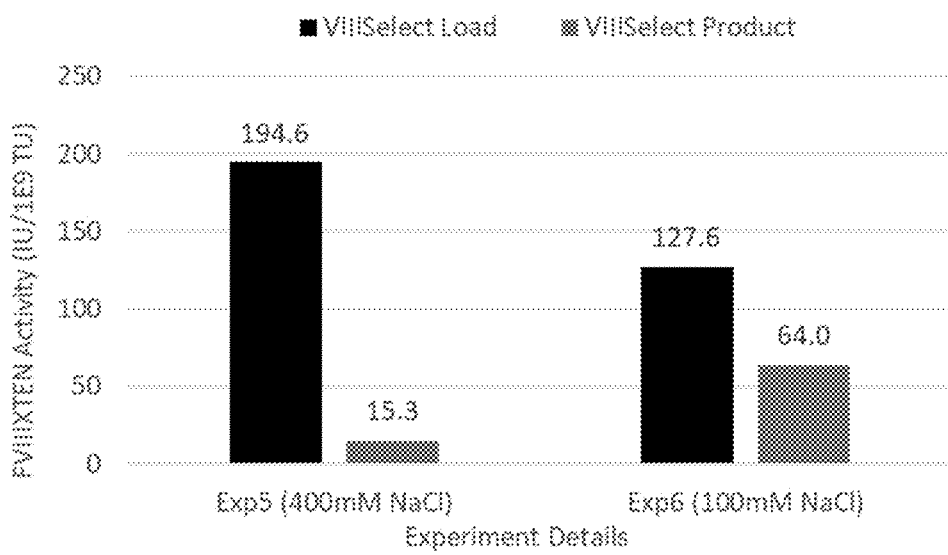
FIGS. 7A-7B are plots showing the impact of salt concentration on the effectiveness of purification using an improved downstream work flow according to one embodiment of the present disclosure.

FIG. 7A shows the level of FVIIIXTEN as a function of total functional lentiviral vector recovered, detected before (black bars; "VIIISelect Load"), and after (grey bars; "VIISelect Product") the VIIISelect purification step. Adjustment of the VIIISelect load sample was performed according to Exp5 and Exp6 described above. As shown in FIG. 7A, when the VIIISelect purification step was performed using a load sample containing 400 mM NaCl (Exp5), the VIIISelect purification step resulted in a decrease of FVIIIXTEN activity from 194.6 IU/1E9 transducing units (TU), to 15.3 IU/1E9 TU, representing a 92% reduction of FVIIIXTEN contaminating transgene protein. In comparison, when the VIIISelect purification step was performed using a load sample containing 100 mM NaCl (Exp5), the VIIISelect purification step resulted in a decrease of FVIIIXTEN activity from 127.6 IU/1E9 TU, to 64 IU/1E9 TU, representing a 50% reduction of FVIIIXTEN contaminating transgene protein. Using Tris buffered load samples, close to 2-fold improvement in the removal of contaminating FVIIIXTEN was achieved when load samples were adjusted to 400 mM NaCl (Exp5) as compared to 100 mM NaCl (Exp6).

Figure 7B:

FIG. 7B shows the results of adjusting load samples to 400 mM NaCl (Exp5) or 100 mM NaCl (Exp6) on FVIIIX-TEN level measured as a function of total lentiviral particle number (IU/1E6 ng P24). As shown in FIG. 7B, when the VIIISelect purification step was performed using a load sample containing 400 mM NaCl (Exp5), the VIIISelect purification step resulted in a decrease of FVIIIXTEN activity from 167.9 IU/1E6 ng P24 to 16.3 IU/1E6 ng P24, representing a 90% reduction of FVIIIXTEN contaminating transgene protein. In comparison, when the VIIISelect purification step was performed using a load sample containing 100 mM NaCl (Exp5), the VIIISelect purification step resulted in a decrease of FVIIIXTEN activity from 125.6 IU/1E6 ng P24 to 75.8 IU/1E6 ng P24, representing a 40% reduction of FVIIIXTEN contaminating transgene protein.

Figure 8:
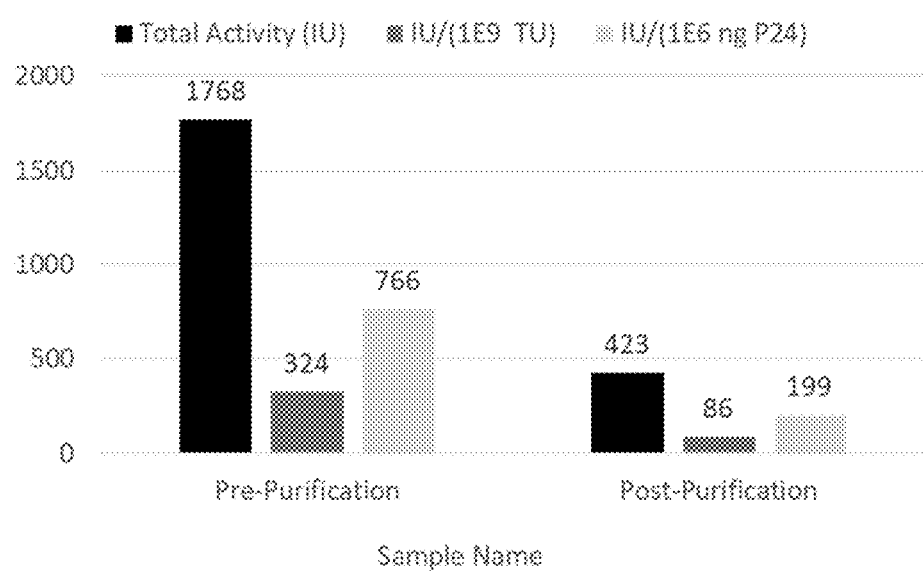
FIG. 8 is a plot showing the total FVIIIXTEN activity detected (black bars), FVIIIXTEN activity detected as a function of total functional vector recovery (dark grey bars), and FVIIIXTEN activity detected as a function of total P24 capsid recovery (light grey bars)

Example 6: Reduction of Contaminating Transgene Protein During Purification Using Phosphate Buffer System with Excipients The purification efficiency of a second chromatography purification step using VIIISelect resin for reduction of FVIIIXTEN contaminating transgene protein was investigated using a phosphate buffer system containing excipients. In this experiment, the load sample was adjusted to contain 400 mM NaCl and 1 mM $CaCl_2$), as well as 10 mM sodium phosphate, sucrose (3% w/v) and poloxamer (0.05% w/v). As shown in FIG. 8, the total activity of FVIIIXTEN detected decreased from 1768 IU pre-purification, to 423 IU post-purification, representing a 76% reduction of FVIIIX-TEN contaminating transgene protein in a single pass, when the sample was allowed to incubate for 10 min residence time in the VIIISelect column. With regards to functional vector recovery of a 400 mM NaCl phosphate buffered load, the FVIIIXTEN activity detected was reduced from 324 IU/1E9 TU pre-purification, to 86 IU/1E9 TU post-purification, representing a 73% reduction in impurity level; FVIIIXTEN activity detected as a function of total lentiviral particle number was reduced from 766 IU/1E6 ng P24 pre-purification, to 199 IU/1E6 ng P24 post-purification, representing a 74% reduction in impurity level.

Example 2, exp2 (see, FIG. 3A and FIG. 3B), using the same phosphate buffered load sample containing 100 mM NaCl (no adjustment of NaCl concentration was performed), the two-column process only resulted in 51% reduction of FVIIIXTEN activity. In comparison, in this experiment, where the phosphate buffered load sample was adjusted to 400 mM NaCl, over 70% reduction in FVIIIXTEN activity was observed, representing a significant enhancement of the reduction in the level of FVIIIXTEN contaminating transgene protein.

Example 7: Reduction of Contaminating Transgene Protein During Purification Using Tris and Phosphate Buffers at Salt Concentration from 200 mM to 600 mM The purification of vector was investigated for removal of contaminating transgene protein using a chromatography purification step in an improved downstream workflow scheme (e.g., as shown in FIG. 1B, FIG. 6A and FIG. 6B). In the improved scheme, the vector product is subjected to a chromatography media specifically designed for removal of contaminating transgene protein impurity present in either Tris or Phosphate buffer containing a range of salt concentration. The removal step of the contaminating transgene protein impurity may be the second chromatography purification step (as shown in FIG. 6A), or it may be the first chromatography step (as shown in FIG. 6B), in an improved downstream workflow scheme of the invention.

Figure 9:
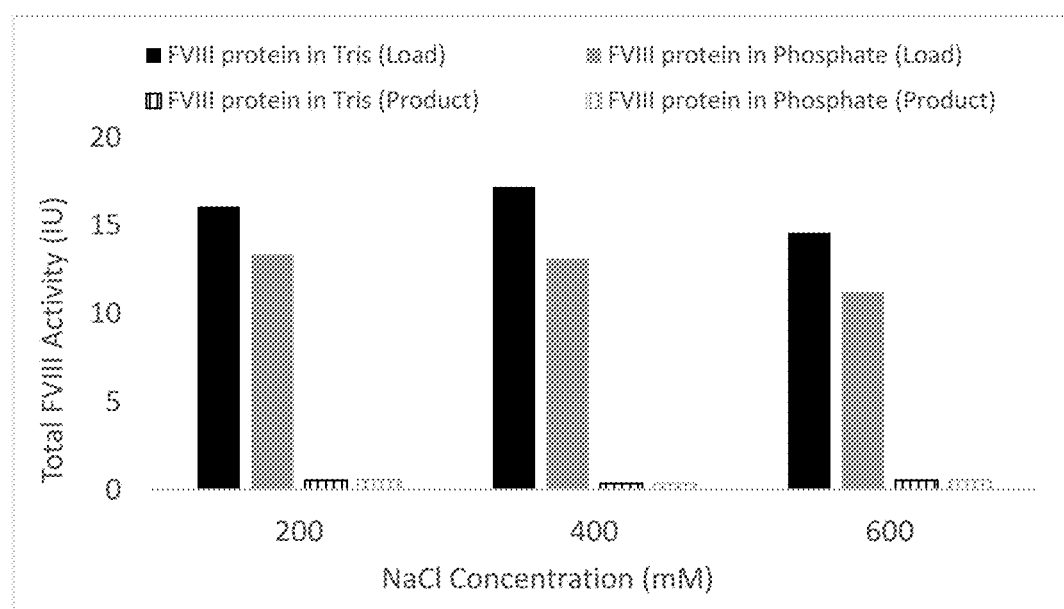
FIG. 9 is a plot showing the impact of various salt concentrations (200, 400 or 600 mM NaCl) on the removal of contaminating FVIII transgene protein during purification of FVIII-encoding viral vectors in a two-step purification process using AEX followed by VIIISelect with TRIS or Phosphate buffers. Total contaminant FVIII transgene activity (IU) was measured in the loading sample (solid black bar for TRIS buffer; solid grey bar for Phosphate loading buffer) following AEX elution and prior to VIIISelect purification and in the flow-through product fraction following VIIISelect purification (lined back bar for TRIS buffer; lined grey bar for Phosphate buffer).

FIG. 9 shows the impact of the concentration of salt in the loading sample on the effectiveness of purification of a second chromatography purification step, wherein the second chromatography purification step comprises the use of VIIISelect resin. In this experiment, a first chromatography purification step using an anion exchange (AEX) column was performed, and the vector product was eluted from the AEX column with an elution buffer comprising either Tris or Phosphate and a total salt concentration of from 200 mM to 600 mM. The AEX eluate (i.e., load sample for the second chromatography purification comprising VIIISelect resin) did not require adjustment if the AEX pool salt concentration was <600 mM but did require adjustment if the AEX pool salt concentration was >600 mM NaCl. The adjusted load sample contained either a range of 200 to 600 mM NaCl, 2.0 mM MgCl2 in Tris-HCl buffer, pH 7.2+0.3; or a range of 200 to 600 mM NaCl, 2.0 mM MgCl2 in Phosphate buffer, pH 7.2+0.3. The adjusted load sample was then applied to second chromatography resin to bind protein impurity and allow the enveloped vector to pass through it as purified vector product.

As shown in FIG. 9, the amount of FVIII protein activity dropped from the activity values above 10 IU to below 1 IU demonstrating at least a 10-fold reduction in contaminating transgene activity, while reducing the protein impurity activity values in vector product sample below the limit of quantitation (<LoQ) of an activity assay. Thus, removal of transgene protein impurities from the sample was achieved by >90% irrespective of whether Tris buffer (compare solid black to lined black bars) or Phosphate buffer (compare solid grey to lined grey bars) was used as a loading buffer in the VIIISelect chromatography step. Furthermore, removal of contaminating transgene product was consistently achieved irrespective of buffer species and salt concentrations. Accordingly, these experiments demonstrate the effectiveness of the improved purification process for removing transgene contaminant without significant loss of functional enveloped viral vector, and demonstrate the general suitability of a variety of buffer species and salt concentrations in the improved purification process.

What is claimed:

1. A method of producing a lentiviral vector (LVV) drug product comprising purifying a LVV from a host cell, the LVV comprising a factor VIII (FVIII) transgene, the method comprising:
   (i) contacting a composition comprising the LVV and a FVIII transgene protein contaminant with a first chromatography matrix, wherein the first chromatography matrix is an affinity chromatography column comprising an affinity ligand that specifically binds to the FVIII transgene protein contaminant; and
   (ii) recovering the LVV in the flow-through of the chromatography matrix,
   thereby separating the LVV from the FVIII protein contaminant.

2. The method of claim 1, further comprising
   (iii) contacting the composition comprising the LVV and the FVIII transgene protein contaminant with a second chromatography matrix capable of selectively binding the LVV, wherein the second chromatography matrix is an anionic exchange (AEX) chromatography matrix or membrane, and
   (iv) eluting the LVV from the second chromatography matrix,
   wherein steps (iii) and (iv) are performed prior to step (i).

3. The method of claim 2, wherein step (iv) is performed by eluting the LVV from the second chromatography matrix with an elution buffer comprising Tris-HCl buffer or phosphate buffer at a pH of about 7.0 to about 7.5.

4. The method of claim 2, further comprising the step of (vi) combining the LVV separated from the FVIII transgene protein contaminant with one or more pharmaceutical excipients to produce a pharmaceutical composition comprising the LVV, wherein step (vi) is performed after step (iv).

5. The method of claim 2, wherein step (vi) is performed by ultrafiltration/diafiltration (UF/DF) of the LVV separated from the FVIII transgene protein contaminant with a formulation buffer, and wherein the UF/DF step comprises tangential flow filtration (TFF).

6. The method of claim 5, wherein the formulation buffer is a phosphate or histidine buffer comprising NaCl and sucrose.

7. The method of claim 1, further comprising
   (iii) contacting the LVV recovered from step (ii) with a second chromatography matrix capable of selectively binding the LVV, wherein the second chromatography matrix is an anionic exchange (AEX) chromatography matrix or membrane, and
   (iv) eluting the LVV from the second chromatography matrix.

8. The method of claim 7, further comprising the step of (v) adjusting salt of the composition comprising the LVV and the FVIII transgene protein contaminant to a target salt concentration from about 0.2M to about 0.6 mM.

9. The method of claim 8, wherein step (v) is performed prior to step (i).

10. The method of claim 8, wherein if steps (iii) and (iv) are performed prior to step (i), then step (v) is performed between steps (iv) and (i).

11. The method of claim 8, wherein the target salt is NaCl.

12. The method of claim 1, wherein step (i) and (ii) are repeated multiple times.

13. The method of claim 1, wherein step (i) is conducted in the presence of an agent that stabilizes the FVIII transgene protein contaminant, and wherein the agent is CaCl2.

14. The method of claim 1, wherein step (i) is performed by loading the first chromatography matrix with the composition comprising the LVV and the FVIII transgene protein contaminant in a loading buffer comprising Tris-HCl buffer or phosphate buffer at a pH about 7.0 to about 7.5.

* * * * *

UNITED STATES PATENT AND TRADEMARK OFFICE
CERTIFICATE OF CORRECTION

| | | |
|---|---|---|
| PATENT NO. | : 12,173,307 B2 | Page 1 of 1 |
| APPLICATION NO. | : 17/356980 | |
| DATED | : December 24, 2024 | |
| INVENTOR(S) | : Mayani et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 616 days.

Signed and Sealed this
Tenth Day of June, 2025

Coke Morgan Stewart
*Acting Director of the United States Patent and Trademark Office*